US006495520B2

(12) United States Patent
Ebner et al.

(10) Patent No.: US 6,495,520 B2
(45) Date of Patent: *Dec. 17, 2002

(54) APOPTOSIS INDUCING MOLECULE II AND METHODS OF USE

(75) Inventors: Reinhard Ebner, Gaithersburg, MD (US); Guo-Liang Yu, Berkeley, CA (US); Steven M. Ruben, Olney, MD (US); Jun Zhang, Bethesda, MD (US); Stephen Ullrich, Rockville, MD (US); Yifan Zhai, Gaithersburg, MD (US)

(73) Assignee: Human Genome Sciences, Inc., Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/252,656

(22) Filed: Feb. 19, 1999

(65) Prior Publication Data

US 2002/0081647 A1 Jun. 27, 2002

Related U.S. Application Data

(63) Continuation-in-part of application No. 09/027,287, filed on Feb. 20, 1998, which is a continuation-in-part of application No. 09/003,886, filed on Jan. 7, 1998, now abandoned, which is a continuation-in-part of application No. 08/822,953, filed on Mar. 21, 1997, now abandoned.
(60) Provisional application No. 60/013,923, filed on Mar. 22, 1996, provisional application No. 60/030,157, filed on Oct. 31, 1996, and provisional application No. 60/075,409, filed on Feb. 20, 1998.

(51) Int. Cl.[7] .................. A61K 38/18; C07K 14/475
(52) U.S. Cl. .................. 514/12; 530/300; 530/324; 530/350
(58) Field of Search .................. 530/350, 328, 530/327, 326, 324; 514/12, 13, 14, 15

(56) References Cited

FOREIGN PATENT DOCUMENTS

| EP | 0 897 114 | | 2/1999 |
|---|---|---|---|
| EP | 0 897 114 A2 | | 2/1999 |
| JP | 191204 | * | 7/1996 |
| JP | 211695 | * | 8/1996 |
| JP | 019330 | * | 1/1997 |
| WO | WO 96/36720 | | 11/1996 |
| WO | WO 97/34911 | | 9/1997 |
| WO | WO 97/41831 | | 11/1997 |
| WO | WO 98/03648 | | 1/1998 |
| WO | WO 98/25967 | | 6/1998 |
| WO | WO 98/28424 | | 7/1998 |
| WO | WO 98/28426 | | 7/1998 |
| WO | WO 98/54323 | | 12/1998 |
| WO | WO 99/02563 | | 1/1999 |
| WO | WO 99/11662 | | 3/1999 |
| WO | WO 99/42584 A1 | | 8/1999 |

OTHER PUBLICATIONS

Bowie et al. Deciphering the message in protein sequences: tolerance to amino acid substitutions. Science, (Mar. 16, 1990) 247 (4948) 1306–10.*
Ngo et al., in The Protein Folding Problem and Tertiary Structure Prediction, Merz and Le Grand (Eds), Aug. 1994, Springer Verlag, pp. 433 and 492–495.*
Aggarwal, B.B, and Natarajan, K., "Tumor necrosis factors: Developments during the last decade," *Eur. Cytokine Netw.* 7:93–124 (Apr.–Jun. 1996).
Gruss, H.–J., "Molecular, structural, and biological characteristics of the tumor necrosis factor ligand superfamily," *Int. J. Clin. Lab. Res.* 26:143–159 (Jan. 1996).
Harrop, J.A., "Herpesvirus Entry Mediator Ligand (HVEM–L), a Novel Ligand for HVEM/TR2, Stimulates Proliferation of T Cells and Inhibits HT29 Cell Growth," *J. Biol. Chem.* 273:27548–27556 (Oct. 1998).
Mauri, D.N. et al., "LIGHT, a New Member of the TNF Superfamily, and Lymphotoxin α Are Ligands for Herpesvirus Entry Mediator," *Immunity* 8:21–30 (Jan. 1998).
Tan, K.B., "Characterization of a novel TNF–like ligand and recently described TNF ligand and TNF receptor superfamily genes and their constitutive and inducible expression in hematopoietic and non–hematopoietic cells," *Gene* 204:35–46 (Dec. 1997).
Anderson, D. et al, "A homologue of the TNF receptor and its ligand enhance T–cell growth and dendritic–cell function," *Nature* 390:175–179 (Nov. 1997).
Barton, G.J., *Protein Structure Prediction, A Practical Approach*, IRL Press, Oxford, UK, pp. 31–63 (1996).
Brunner, T. et al.,"Cell–autonomous Fas (CD95)/Fas–ligand interaction mediates activation–induced apoptosis in T–cell hybridomas," *Nature* 373:441–444 (Feb. 1995).
Chen, C.–M. et al., "Direct Interaction of Hepatitis C Virus Core Protein with the Cellular Lymphotoxin–β Receptor Modulates the Signal Pathway of the Lymphotoxin–β Receptor," *J. Virol.* 71:9417–9426 (Dec. 1997).
Font, J. et al., "Elevated Soluble CD27 Levels in Serum of Patients with Systemic Lupus Erythematosus," *Clin. Immunol. Immunopathol.* 81:239–243 (Dec. 1996).

(List continued on next page.)

Primary Examiner—David S. Romeo
(74) Attorney, Agent, or Firm—Sterne, Kessler, Goldstein & Fox P.L.L.C.

(57) ABSTRACT

The present invention relates to a novel member of the TNF-Ligand superfamily. More specifically, isolated nucleic acid molecules are provided encoding a human Apoptosis Inducing Molecule II (AIM II). AIM II polypeptides are also provided, as are vectors, host cells and recombinant methods for producing the same. The invention further relates to screening methods for identifying agonists and antagonists of AIM II activity. Also provided are therapeutic methods for treating lymphadenopathy, aberrant bone development, autoimmune and other immune system diseases, graft versus host disease, rheumatoid arthritis, osteoarthritis and to inhibit neoplasia, such as tumor cell growth.

8 Claims, 38 Drawing Sheets

OTHER PUBLICATIONS

George, D.G. et al., "Current Methods in Sequence Comparison and Analysis," *Macromolecular Sequencing and Synthesis, Selected Methods and Applications*, D.H. Sclesinger (ed.), Liss Inc. Pbl. New York, NY pp 127–149 (1988).

Gruss, H.J. and Dower, S.K., "The TNF ligand superfamily and its relevance for human diseases," *Cytokines and Molecular Therapy* 1(2):75–105 (Jun. 1995).

Gruss, H.J. and Dower, S.K., "Tumor Necrosis Factor Ligand Superfamily: Involvement in the Pathology of Malignant Lymphomas," *Blood* 85(12):3378–3404 (Jun. 1995).

Gruss, H.J. and Herman, F., "CD30 Ligand, a Member of the TNF Ligand Superfamily, with Growth and Activation Control for CD30+ Lymphoid and Lymphoma Cells," *Leukemia and Lymphoma* 20:397–409 (Feb. 1996).

Gruss, H.J., et al., "Structural and biological features of the TNF receptor and TNF ligand superfamilies: Interactive signals in the pathobiology of Hodgkins disease," *Annals of Oncology* 7(Supp. 4):S19–S26 (1996).

Ju, S.–T. et al., "Fas(CD95)/FasL interactions required for programmed cell death after T–cell activation," *Nature* 373:444 (Feb. 1995).

Kallio, P. et al., "Soluble CD27 in thyroid disorders," *J. Lab Clin. Med.* 132:478–482 (Dec. 1998).

Kersten. M.J. et al., "Elevation of Cerebrospinal Fluid Soluble CD27 Levels in Patients With Meningeal Localization of Lymphoid Malignancies," *Blood* 87:1985–1989 (Mar. 1996).

Kwon, B.S. et al., "A Newly Identified Member of the Tumor Necrosis Factor Receptor Superfamily with a Wide Tissue Distribution and Involvement in Lymphocyte Activation," *J. Biol. Chem.* 272:14272–14276 (May 1997).

Lundwall, A., "Characterization of the gene for prostate–specific anitgen, a human glandular kallikrein," *Biochem. Biophys. Res. Commun.*, 161(3):1151–1159 (Jun. 1989).

Nagumo, H. et al., "CD27/CD70 Interaction Augments IgE Secretion by Promoting the Differentiation of Memory B Cells into Plasma Cells," *J. Immun.* 161:6492–6502 (Dec. 1998).

Pandanilam, B. et al., "Expression of CD27 and ischemia/reperfusion–induced expression of its ligand Siva in rat kidneys," *Kidney Int.* 54:1967–1975 (Dec. 1998).

Ranheim, E.A. et al., "Expression of CD27 and its Ligand, CD70, on Chronic Lymphocytic Leukemia B Cells," *Blood* 85:3556–3565 (Jun. 1995).

Rennert, P.D. et al., "Selective disruption of lymphotoxin ligands reveals a novel set of mucosal lymph nodes and unique effects on lymph node cellular organization," *Int. Immunol.* 9:1627–1639 (Nov. 1997).

Sigurdsson, T. et al., "Peridontal Regenerative Potential of Space–Providing Expanded Polytetrafluoroethylene Membranes and Recombinant Human Bone Morphogenetic Proteins," *J. Periodontol.* 66:511–521 (Jun. 1995).

Suda, T. et al., "Molecular Cloning and Expression of the Fas Ligand, a Novel Member of the Tumor Necrosis Factor Family," *Cell* 75:1169–1178 (Dec. 1993).

Swaak, A.J.G. et al., "Serum Levels of Soluble Forms of T–Cell Activation Antigens CD27 and CD25 in Systemic Lupus Erythematosus in Relation with Lymphocytes Count and Disease Course," *Clin. Rheumatol.* 14:293–300 (May 1995).

Takahashi, T., et al. "Generalized Lymphoproliferative Disease in Mice, Caused by a Point Mutation in the Fas Ligand," *Cell* 76:969–976 (Mar. 1994).

Takahashi, T., et al., "Human Fas ligand: gene structure, chromosomal location and species specificity," *International Immunology* 6(10):1567–1574 (Oct. 1994).

Takeda, Y. et al., Rapid acceleration of neutrophil apoptosis by tumor necrosis factor α, *International Immunology* 5(6):691–694 (Jun. 1993).

Tanaka, M. et al., "Expression of the functional soluble form of human Fas ligand in activated lymphocytes," *EMBO J.* 14(6):1129–1135 (Mar. 1995).

NCBI Entrez, GenBank Report, Accession No. M27274, submitted by Lundwall, A., (Nov. 1989).

NCBI Entrez. GenBank Report, Accession No. T74524, submitted by Hillier et al. (Mar. 1995).

NCBI Entrez, GenBank Report, Accession No. H73550, submitted by Hillier et al. (Oct. 1995).

NCBI Entrez, GenBank Report, Accession No. N77915, submitted by Hillier et al. (Mar. 1996).

NCBI Entrez, GenBank Report, Accession No. AA491814, from NCI–CGAP (Aug. 1997).

NCBI Entrez, GenBank Report, Accession No. AA570740, from NCI–CGAP (Sep. 1997).

NCBI Entrez, GenBank Report, Accession No. AA747757, from NCI–CGAP (Feb. 1998).

NCBI Entrez, GenBank Report, Accession No. AA568204, from NCI–CGAP (Mar. 1999).

Harrop, J., et al., "HVEM–L, A Novel Ligand for HVEM/TR2, Stimulates NF–κB Dependent Transcription and T Cell Proliferation," *J. Int. Cytokine Res.* 18:A–39 (1998).

\* cited by examiner

```
          10                 30                    50
GAGGTTGAAGGACCCAGGCGTGTCAGCCCTGCTCCAGAGACCTTGGGCATGGAGGAGAGT
---------+---------+---------+---------+---------+---------+
                                                  M  E  E  S
          70                 90                   110
GTCGTACGGCCCTCAGTGTTTGTGGTGGATGGACAGACCGACATCCCATTCACGAGGCTG
---------+---------+---------+---------+---------+---------+
 V  V  R  P  S  V  F  V  V  D  G  Q  T  D  I  P  F  T  R  L
          130                150                  170
GGACGAAGCCACCGGAGACAGTCGTGCAGTGTGGCCCGGGTGGGTCTGGGTCTCTTGCTG
---------+---------+---------+---------+---------+---------+
 G  R  S  H  R  R  Q  S  C  S  V  A  R  V  G  L  G  L  L  L
          190                210                  230
TTGCTGATGGGGGCTGGGCTGGCCGTCCAAGGCTGGTTCCTCCTGCAGCTGCACTGGCGT
---------+---------+---------+---------+---------+---------+
 L  L  M  G  A  G  L  A  V  Q  G  W  F  L  L  Q  L  H  W  R
          250                270                  290
CTAGGAGAGATGGTCACCCGCCTGCCTGACGGACCTGCAGGCTCCTGGGAGCAGCTGATA
---------+---------+---------+---------+---------+---------+
 L  G  E  M  V  T  R  L  P  D  G  P  A  G  S  W  E  Q  L  I
          310                330                  350
CAAGAGCGAAGGTCTCACGAGGTCAACCCAGCAGCGCATCTCACAGGGGCCAACTCCAGC
---------+---------+---------+---------+---------+---------+
 Q  E  R  R  S  H  E  V  N  P  A  A  H  L  T  G  A  N  S  S
          370                390                  410
TTGACCGGCAGCGGGGGGCCGCTGTTATGGGAGACTCAGCTGGGCCTGGCCTTCCTGAGG
---------+---------+---------+---------+---------+---------+
 L  T  G  S  G  G  P  L  L  W  E  T  Q  L  G  L  A  F  L  R
          430                450                  470
GGCCTCAGCTACCACGATGGGGCCCTTGTGGTCACCAAAGCTGGCTACTACTACATCTAC
---------+---------+---------+---------+---------+---------+
 G  L  S  Y  H  D  G  A  L  V  V  T  K  A  G  Y  Y  Y  I  Y
          490                510                  530
TCCAAGGTGCAGCTGGGCGGTGTGGGCTGCCCGCTGGGCCTGGCCAGCACCATCACCCAC
---------+---------+---------+---------+---------+---------+
 S  K  V  Q  L  G  G  V  G  C  P  L  G  L  A  S  T  I  T  H
          550                570                  590
GGCCTCTACAAGCGCACACCCCGCTACCCCGAGGAGCTGGAGCTGTTGGTCAGCCAGCAG
---------+---------+---------+---------+---------+---------+
 G  L  Y  K  R  T  P  R  Y  P  E  E  L  E  L  L  V  S  Q  Q
          610                630                  650
TCACCCTGCGGACGGGCCACCAGCAGCTCCCGGGTCTGGTGGGACAGCAGCTTCCTGGGT
```

GGTGTGGTACACCTGGAGGCTGGGGAGGAGGTGGTCGTCCGTGTGCTGGATGAACGCCTG
---------+---------+---------+---------+---------+---------+
  G  V  V  H  L  E  A  G  E   V  V  V  R  V  L  D   E  R  L
        730                750                770

GTTCGACTGCGTGATGGTACCCGGTCTTACTTCGGGGCTTTCATGGTGTGAAGGAAGGAG
---------+---------+---------+---------+---------+---------+
  V  R  L  R  D  G  T  R  S   Y  F  G  A  F  M  V   *
        790                810                830

CGTGGTGCATTGGACATGGGTCTGACACGTGGAGAACTCAGAGGGTGCCTCAGGGGAAAG
---------+---------+---------+---------+---------+---------+
        850                870                890

AAAACTCACGAAGCAGAGGCTGGGCGTGGTGGCTCTCGCCTGTAATCCCAGCACTTTGGG
---------+---------+---------+---------+---------+---------+
        910                930                950

AGGCCAAGGCAGGCGGATCACCTGAGGTCAGGAGTTCGAGACCAGCCTGGCTAACATGGC
---------+---------+---------+---------+---------+---------+
        970                990                1010

AAAACCCCATCTCTACTAAAAATACAAAAATTAGCCGGACGTGGTGGTGCCTGCCTGTAA
---------+---------+---------+---------+---------+---------+
       1030               1050               1070

TCCAGCTACTCAGGAGGCTGAGGCAGGATAATTTTGCTTAAACCCGGGAGGCGGAGGTTG
---------+---------+---------+---------+---------+---------+
       1090               1110               1130

CAGTGAGCCGAGATCACACCACTGCACTCCAACCTGGGAAACGCAGTGAGACTGTGCCTC
---------+---------+---------+---------+---------+---------+
       1150

AAAAAAAAAAAAAAAAAAAAAAAAAAAA
---------+---------+---------
```

FIG.1B

```
                10                     30
ATTCCCCGGGCCCGGGTGGGTCTGGGTCTCTTGCTGTTGCTGATG
---------+---------+---------+---------+-----
 I  P  R  A  R  V  G  L  G  L  L  L  L  L  M
    50                  70                  90

GGGGCCGGGCTGGCCGTCCAAGGCTGGTTCCTCCTGCAGCTGCAC
----+---------+---------+---------+---------+
 G  A  G  L  A  V  Q  G  W  F  L  L  Q  L  H
                 110                    130

TGGCGTCTAGGAGAGATGGTCACCCGCCTGCCTGACGGACCTGCA
---------+---------+---------+---------+-----
 W  R  L  G  E  M  V  T  R  L  P  D  G  P  A
             150                    170

GGCTCCTGGGAGCAGCTGATACAAGAGCGAAGGTCTCACGAGGTC
----+---------+---------+---------+---------+
 G  S  W  E  Q  L  I  Q  E  R  R  S  H  E  V
          190                    210

AACCCAGCAGCGCATCTCACAGGGGCCAACTCCAGCTTGACCGGC
---------+---------+---------+---------+-----
 N  P  A  A  H  L  T  G  A  N  S  S  L  T  G
    230                  250                270

AGCGGGGGGCCGCTGTTATGGGAGACTCAGCTGGGCCTGGCCTTC
----+---------+---------+---------+---------+
 S  G  G  P  L  L  W  E  T  Q  L  G  L  A  F
                 290                    310

CTGAGGGGCCTCAGCTACCACGATGGGGCCCTTGTGGTCACCAAA
---------+---------+---------+---------+-----
 L  R  G  L  S  Y  H  D  G  A  L  V  V  T  K
          330                    350

GCTGGCTACTACTACATCTACTCCAAGGTGCAGCTGGGCGGTGTG
----+---------+---------+---------+---------+
 A  G  Y  Y  Y  I  Y  S  K  V  Q  L  G  G  V
             370                    390

GGCTGCCCGCTGGGCCTGGCCAGCACCATCACCCACGGCCTCTAC
---------+---------+---------+---------+-----
 G  C  P  L  G  L  A  S  T  I  T  H  G  L  Y
    410                  430                450

AAGCGCACACCCCGCTACCCCGAGGAGCTGGAGCTGTTGGTCAGC
----+---------+---------+---------+---------+
 K  R  T  P  R  Y  P  E  E  L  E  L  L  V  S
                 470                    490
```

FIG.1C

```
CAGCAGTCACCCTGCGGACGGGCCACCAGCAGCTCCCGGGTCTGG
---------+---------+---------+---------+-----
 Q  Q  S  P  C  G  R  A  T  S  S  S  R  V  W
            510              530

TGGGACAGCAGCTTCCTGGGTGGTGTGGTACACCTGGAGGCTGGG
----+---------+---------+---------+---------+
 W  D  S  S  F  L  G  G  V  V  H  L  E  A  G
        550              570

GAGGAGGTGGTCGTCCGTGTGCTGGATGAACGCCTGGTTCGACTG
---------+---------+---------+---------+-----
 E  E  V  V  V  R  V  L  D  E  R  L  V  R  L
    590              610              630

CGTGATGGTACCCGGTCTTACTTCGGGGCTTTCATGGTGTGAAGG
----+---------+---------+---------+---------+
 R  D  G  T  R  S  Y  F  G  A  F  M  V  *
              650              670

AAGGAGCGTGGTGCATTGGACATGGGTCTGACACGTGGAGAACTC
---------+---------+---------+---------+-----
         690              710

AGAGGGTGCCTCAGGGGAAAGAAAACTCACGAAGCAGAGGCTGGG
----+---------+---------+---------+---------+
         730              750

CGTGGTGGCTCTCGCCTGTAATCCCAGCACTTTGGGAGGCCAAGG
---------+---------+---------+---------+-----
    770              790              810

CAGGCGGATCACCTGAGGTCAGGAGTTCGAGACCAGCCTGGCTAA
----+---------+---------+---------+---------+
              830              850

CATGGCAAAACCCCATCTCTACTAAAAATACAAAAATTAGCCGGA
---------+---------+---------+---------+-----
         870              890

CGTGGTGGTGCCTGCCTGTAATCCAGCTACTCAGGAGGCTGAGGC
----+---------+---------+---------+---------+
    910              930

AGGATAATTTTGCTTAAACCCGGGAGGCGGAGGTTGCAGTGAGCC
---------+---------+---------+---------+-----
    950              970              990

GAGATCACACCACTGCACTCCAACCTGGGAAACGCAGTGAGACTG
----+---------+---------+---------+---------+
              1010

TGCCTCAAAAAAAACAAAAAAAAAAAA
---------+---------+--------
```

```
    QTARQHPSMELAKSTLKPAAHLIGDPSS-- Majority
             190        200        210
 77 A G S W E Q L I Q E R R S H E V N P A A H L T G A N S S L T Aim-2.aa
181 S C S N C K K S L E C T K L C L P Q I E N V K G T E D S G T huTNFalpha.prot
 46 Q T A R Q H P K M H L A H S T L K P A A H L I G D P S K - - huTNFbeta.prot
 46 Q T A R Q H P K M H L A H S T L K P A A H L I G D P S K - - huLymphotoxin.prot
128 E K Q I G H P S P P P E K K E L R K V A H L T G K S N S - - huFasLigand.prot

- Q N - P L L - - - - - - - - - - - - - - - - - - - - W E Majority
             220        230        240
107 G S G G P L L - - - - - - - - - - - - - - - - - - - - W E Aim-2.aa
211 T V L L P L V I F F G L C L L S L L F I G L M Y R Y Q R W K huTNFalpha.prot
 74 - Q N - S L L - - - - - - - - - - - - - - - - - - - - W R huTNFbeta.prot
 74 - Q N - S L L - - - - - - - - - - - - - - - - - - - - W R huLymphotoxin.prot
156 - R S M P L E - - - - - - - - - - - - - - - - - - - - W E huFasLigand.prot A N L G R A F - - - - - - - - - - - - - - - - L Q D G Majority
             250        260        270
116 T Q L G L A F - - - - - - - - - - - - - - - - L R - G Aim-2.aa
241 S K L Y S I V C G K S T P E K E G E L E G T T T K P L A P N huTNFalpha.prot
 81 A N T D R A F - - - - - - - - - - - - - - - - L Q D G huTNFbeta.prot
 81 A N T D R A F - - - - - - - - - - - - - - - - L Q D G huLymphotoxin.prot
164 D T Y G I V L - - - - - - - - - - - - - - - - L - S G huFasLigand.prot
```

```
            D Q L S V H V D G I P L L V L S E S T - V F F - - - - - Majority
                              |                   |
                             370                 380                390

213  E E V V V R V L D E R L V R L R D G T R S Y F - - - - -  Aim-2.aa
357  A T L Y A V V E N V P P L R W K E F V R - - - - - - - -  huTNFalpha.prot
179  D Q L S T H T D G I P H L V L S P S T - V F F - - - - -  huTNFbeta.prot
179  D Q L S T H T D G I P H L V L S P S T - V F F - - - - -  huLymphotoxin.prot
255  D H L Y V N V S E L S L V N F E E S Q - T F F - - - - -  huFasLigand.prot

- - - - - - - - - - - G A F A - L - - - - - - - - Majority
                              |                   |
                             400                 410                420

236  - - - - - - - - - - - - - - - - - - - - - - - - - - - -  Aim-2.aa
387  R L E L Q N G R C L R E A Q Y S M L A T W R R R T P R R E A  huTNFalpha.prot
201  - - - - - - - - - - - - G A F M V - - - - - - - - - - -  huTNFbeta.prot
201  - - - - - - - - - - - - G A F A - L - - - - - - - - - -  huLymphotoxin.prot
277  - - - - - - - - - - - - G L Y K - L - - - - - - - - - -  huFasLigand.prot
```

FIG.2F

```
                              430            440           450
                    |---------|----|---------|----|---------|----  Majority 241                                                                Aim-2.aa
417  T L E L L G R V L R D M D L L G C L E D I E E A L C G P A A   huTNFalpha.prot
205                                                                huTNFbeta.prot
205                                                                huLymphotoxin.prot
281                                                                huFasLigand.prot

|---------|----|---------|----                 Majority

241                                                                Aim-2.aa
447  L P P A P S L L R                                             huTNFalpha.prot
205                                                                huTNFbeta.prot
205                                                                huLymphotoxin.prot
281                                                                huFasLigand.prot
```

DECORATION 'DECORATION #1': SHADE (WITH SOLID BRIGHT COLBALT) RESIDUES THAT MATCH Aim-2.aa E

| CELL LINES | LTγ EXPRESSION[1] | LTβR EXPRESSION[1] | TR2 EXPRESSION[1] | GROWTH INHIBITION BY LTγ[2] |
|---|---|---|---|---|
| MDA-MB-231 | − | ++ | ++ | ++ |
| MCF-7 | − | ++ | ++ | ++ |
| HT-29 | − | +++ | ++ | ++++ |
| MC-3 | − | ++ | − | − |
| U93T | − | − | + | − |
| MCF-10A | ++ | + | ± | − |
| PBMC[3] | + | − | + | − |
| T-CELLS | + | − | ++ | − |
| TIL 1200 | + | − | + | − |
| Jurkat | − | − | + | − |

1. EXPRESSION OF LTγ WAS DETERMINED BY RT-PCR ASSAY; EXPRESSION OF LTβR AND TR2 WAS DETERMINED BY FACS ANALYSIS;
2. CYTOTOXICITY WAS CARRIED OUT WITH 50ng/ml OF LTγ IN THE PRESENCE OF 10 μ/ml OF IFNγ. +: 30% INHIBITION, ++:50% INHIBITION, +++;80% INHIBITION, −: LESS THAN 10% INHIBITION.
3. LTγ WAS FOUND ONLY IN ACTIVATED PBMC NOT IN RESTING PBMC.

FIG.8L

```
                                    -35       OPERATOR 1
1  AAGCTTAAAAAACTGCAAAAAATAGT TTGACT TGTGAGCGGATAACAAT

-10                  OPERATOR 2
50 TAAGAT GTACCCA ATTGTGAGCGGATAACAAT TTCACACATTAA

S/D
94 AGAGGAG AAATTA CATATG
```

FIG.11

```
1   M G L S T V P D L L L P L V L L E L L V G I Y P S G V I G L   huTNFalpha.prot
1   M - - T P P E R L F L P R V - - - - - - - - - - - - - - - -   huTNFbeta.prot
1   M - - T P P E R L F L P R V - - - - - - - - - - - - - - - -   huLymphotoxin.prot
1   M - - Q Q P F N Y P Y P Q I Y W V D S S A S S P W A P P G T   huFasLigand.prot
1   - - - I P R A - - - - - - - - - - - - - - - - - - - - - - -   huAIM-2.prot
            └─────┘
                      10                  20                30

31  V P H L G D R E K R D S V C P Q G K Y I H P Q N N S I C C T   huTNFalpha.prot
13  - - - - - - - - - - - - - - - C G T T L H - - - - - - - - -   huTNFbeta.prot
13  - - - - - - - - - - - - - - - C G T T L H - - - - - - - - -   huLymphotoxin.prot
29  V L P - - - - - - - - - - - C P T S V P R R P G Q R R - - -   huFasLigand.prot
5   - - - - - - - - - - - - - - - - - - - - - - - - - - - - - -   huAIM-2.prot
                      40                  50                60

61  K C H K G T Y L Y N D C P G P G Q D T D C R E C E S G S F T   huTNFalpha.prot
19  - - - - - - - - - - - - - - - - - - - - - - - - - - - - - -   huTNFbeta.prot
19  - - - - - - - - - - - - - - - - - - - - - - - - - - - - - -   huLymphotoxin.prot
45  - - - - - - - - - - P P P P P P P L P P P P P P P P P P P P   huFasLigand.prot
5   - - - - - - - - - - - - - - - - - - - - - - - - - - - - - -   huAIM-2.prot
                      70                  80                90
```

```
                100              110              120
                 |                |                |
 91  ASENHLRHCLSCSKC RKE MGQVEISSCTVD  huTNFalpha.prot
 19  ---LLL------------------LGLLL VL LPGAQ        huTNFbeta.prot
 19  ---LLL------------------LGLLL VL LPGAQ        huLymphotoxin.prot
 63  LPPLPLPPLKKRGNHSTG L C LLV MFF MVLV           huFasLigand.prot
  -  ------------------RVGLGLLLL MGAGL             huAIM-2.prot 130              140              150
                 |                |                |
121  RDTVCGGCRKNQYRHYWSENL F QCFNCSLCL             huTNFalpha.prot
 34  GLPGVG---------------L-----------              huTNFbeta.prot
 34  GLPGVG---------------L-----------              huLymphotoxin.prot
 93  ALVGLG---------------LG M F Q LF --            huFasLigand.prot
 20  AVQ ------------------ C W F - LL --           huAIM-2.prot 160              170              180
                 |                |                |
151  NGTVH L SCQEKQNTVCTCHAGFFL RE NECV            huTNFalpha.prot
 41  ---H L QKE L A ELRESTSQ--- -TP SAA             huTNFbeta.prot
 41  ---H L QKE L A ELRESTSQ--- -TP SAA             huLymphotoxin.prot
106  -------------MHTASSL-----                      huFasLigand.prot
 28  QLHWRLGEMVT------------- RLPDGP                huAIM-2.prot
```

FIG. 14C

```
             190                 200                 210
181 S C S N C K K S L E C T K L C L P Q I E N V K G T E D S G I  huTNFalpha.prot
 46 Q T A R Q H P K M H L A H S T L K P A A H L I G D P S K - -  huTNFbeta.prot
 46 Q T A R Q H P K M H L A H S T L K P A A H L I G D P S K - -  huLymphotoxin.prot
128 E K Q I G H P S P P P E K K E L R K V A H L T G K S N S - -  huFasLigand.prot
 45 A G S W E Q L I Q E R R S H E V N P A A H L T G A N S S L T  huAIM-2.prot 220                 230                 240
211 T V L L P L V I F F G L C L L S L L F I G L M Y R Y Q R W K  huTNFalpha.prot
  4 - Q N - S L L - - - - - - - - - - - - - - - - - - - - W R  huTNFbeta.prot
 74 - Q N - S L L - - - - - - - - - - - - - - - - - - - - W R  huLymphotoxin.prot
156 - R S M P L E - - - - - - - - - - - - - - - - - - - - W E  huFasLigand.prot
 75 G S G G P L L - - - - - - - - - - - - - - - - - - - - W E  huAIM-2.prot 250                 260                 270
241 S K L Y S I V C G K S T P E K E G E L E G T T T K P L A P N  huTNFalpha.prot
 81 A N T D R A F - - - - - - - - - - - - - - - - - - - L Q D G  huTNFbeta.prot
 81 A N T D R A F - - - - - - - - - - - - - - - - - - - L Q D G  huLymphotoxin.prot
164 D T Y G I V L - - - - - - - - - - - - - - - - - - - L - S G  huFasLigand.prot
 84 T Q L G L A F - - - - - - - - - - - - - - - - - - - L R - G  huAIM-2.prot
```

```
                                280                   290                   300
271 P S F S P T P G F T P T L G F S P V P S S T F T S S S T Y T  huTNFalpha.prot
 92 F S L S N N S L L V P T S G I Y F V Y S Q V V F S G K A Y S  huTNFbeta.prot
 92 F S L S N N S L L V P T S G I Y F V Y S Q V V F S G K A Y S  huLymphotoxin.prot
174 V K Y K K G G L V I N E T G L Y F V Y S K V Y F R G Q S C N  huFasLigand.prot
 94 L S Y H D G A L V V T K A G Y Y Y I Y S K V Q L G G V G C P  huAIM-2.prot 310                   320
301 P G D C P N F A A P R R E V - - A P P Y Q G A D P I L A T    huTNFalpha.prot
122 P K A P S S P L Y L A H E V Q L F S S Q Y P F H V P L L S S  huTNFbeta.prot
122 P K A T S S P L Y L A H E V Q L F S S Q Y P F H V P L L S S  huLymphotoxin.prot
204 - - - - - N L P L S H K V Y M R N S K Y P Q D L V M M E G    huFasLigand.prot
124 L G L A S T - - - I T H G L Y K R T P R Y P E E L E L L V S  huAIM-2.prot 340                   350
328 A - L A S D P I P N P L Q K W E D S A H K P Q S L D T D D P  huTNFalpha.prot
152 Q K M V Y - - - P G L Q E P W L H S M Y H G A A F Q L T Q G  huTNFbeta.prot
152 Q K M V Y - - - P G L Q E P W L H S M Y H G A A F Q L T Q G  huLymphotoxin.prot
228 K M M S Y - - - C T T G Q M W A R S S Y L G A V F N L T S A  huFasLigand.prot
151 Q S P C G R A T S S S R V W W D S S F L G G V V H L E A G    huAIM-2.prot
```

```
                     360                 370                 380
357 A T L Y A V V E N V P P L R W K E F V R R L G L S D H E I D  huTNFalpha.prot
179 D Q L S T H T D G I P H L V L S P S T - V F F - - - - - - -  huTNFbeta.prot
179 D Q L S T H T D G I P H L V L S P S T - V F F - - - - - - -  huLymphotoxin.prot
255 D H L Y V N V S E L S L V N F E E S Q - I F F - - - - - - -  huFasLigand.prot
181 E E V V V R V L D E R L V R L R D G T R S Y F - - - - - - -  huAIM-2.prot 390                 400                 410
387 R L E L Q N G R C L R E A Q Y S M L A T W R R R T P R R E A  huTNFalpha.prot
201 - - - - - - - - - - - - - G A F A - L - - - - - - - - - - -  huTNFbeta.prot
201 - - - - - - - - - - - - - G A F A - L - - - - - - - - - - -  huLymphotoxin.prot
277 - - - - - - - - - - - - - G L Y K - L - - - - - - - - - - -  huFasLigand.prot
204 - - - - - - - - - - - - - G A F M V - - - - - - - - - - - -  huAIM-2.prot 420                 430                 440
417 T L E L L G R V L R D M D L L G C L E D I E E A L C G P A A  huTNFalpha.prot
205 - - - - - - - - - - - - - - - - - - - - - - - - - - - - - -  huTNFbeta.prot
205 - - - - - - - - - - - - - - - - - - - - - - - - - - - - - -  huLymphotoxin.prot
281 - - - - - - - - - - - - - - - - - - - - - - - - - - - - - -  huFasLigand.prot
209 - - - - - - - - - - - - - - - - - - - - - - - - - - - - - -  huAIM-2.prot
```

FIG.14F

447 L P P A P S L L R   huTNFalpha.prot
205                    huTNFbeta.prot
205                    huLymphotoxin.prot
281                    huFasLigand.prot
209                    huAIM-2.prot

US 6,495,520 B2

APOPTOSIS INDUCING MOLECULE II AND METHODS OF USE

CROSS-REFERENCE TO RELATED APPLICATIONS

The present application claims benefit to the filing date of provisional application No. 60/075,409, filed Feb. 20, 1998, and is a Continuation-in-Part of application Ser. No. 09/027,287, filed on Feb. 20, 1998, each of which is herein incorporated by reference; said Ser. No. 09/027,287 is a Continuation-in-Part of application Ser. No. 09/003,886, filed Jan. 7, 1998 now abandoned, which is herein incorporated by reference; said Ser. No. 09/003,886 is a Continuation-in-Part of application Ser. No. 08/822,953, filed Mar. 21, 1997 now abandoned, which is herein incorporated by reference; said Ser. No. 08/822,953 claims benefit to the filing date of provisional applications Nos. 60/013,923, filed Mar. 22, 1996 and 60/030,157, filed Oct. 31, 1996, each of which is incorporated herein by reference.

BACKGROUND OF THE INVENTION

1. Field of the Invention

The present invention relates to a novel member of the TNF-Ligand superfamily. More specifically, isolated nucleic acid molecules are provided encoding a human Apoptosis Inducing Molecule II (AIM II). AIM II polypeptides are also provided, as are vectors, host cells and recombinant methods for producing the same. The invention further relates to screening methods for identifying agonists and antagonists of AIM II activity. Also provided are therapeutic methods for treating lymphadenopathy, aberrant bone development, autoimmune and other immune system diseases, graft versus host disease, rheumatoid arthritis, osteoarthritis and to inhibit neoplasia, such as tumor cell growth.

2. Related Art

Human tumor necrosis factors α (TNF-α) and β (TNF-β, or lymphotoxin) are related members of a broad class of polypeptide mediators, which includes the interferons, interleukins and growth factors, collectively called cytokines (Beutler, B. and Cerami, A., Annu. Ret,. Immunol., 7:625–655 (1989)).

Tumor necrosis factor (TNF-α and TNF-β) was originally discovered as a result of its anti-tumor activity, however, now it is recognized as a pleiotropic cytokine capable of numerous biological activities including apoptosis of some transformed cell lines, mediation of cell activation and proliferation and also as playing important roles in immune regulation and inflammation.

To date, known members of the TNF-ligand superfamily include TNF-α, TNF-β (lymphotoxin-α), LT-β, OX40L, Fas ligand, CD30L, CD27L, CD40L and 4-IBBL. The ligands of the TNF ligand superfamily are acidic, TNF-like molecules with approximately 20% sequence homology in the extracellular domains (range, 12%–36%) and exist mainly as membrane-bound forms with the biologically active form being a trimeric/multimeric complex. Soluble forms of the TNF ligand superfamily have only been identified so far for TNF, LTα, and Fas ligand (for a general review, see Gruss, H. and Dower, S. K., Blood, 85(12):3378–3404 (1995)), which is hereby incorporated by reference in its entirety.

These proteins are involved in regulation of cell proliferation, activation, and differentiation, including control of cell survival or death by apoptosis or cytotoxicity (Armitage, R. J., Curr. Opin. Immunol 6:407(1994) and Smith, C. A., Cell 75:959(1994)).

Mammalian development is dependent on both the proliferation and differentiation of cells as well as programmed cell death which occurs through apoptosis (Walker, et al., Methods Achiev. Exp. Pathol. 13:18(1988). Apoptosis plays a critical role in the destruction of immune thymocytes that recognize self antigens. Failure of this normal elimination process may play a role in autoimmune diseases (Gammon et al., Immunology Today 12:193(1991)).

Itoh et al. (Cell 66:233(1991)) described a cell surface antigen, Fas/CD95 that mediates apoptosis and is involved in clonal deletion of T-cells. Fas is expressed in activated T-cells, B-cells, neutrophils and in thymus, liver, heart and lung and ovary in adult mice (Watanabe-Fukunaga et al., J. Immunolo. 148:1274(1992)) in addition to activated T-cells, B-cells, neutorophils. In experiments where a monoclonal Ab to Fas is cross-linked to Fas, apoptosis is induced (Yonehara et al., J Exp. Med. 169:1747(1989); Trauth et al., Science 245:301(1989)). In addition, there is an example where binding of a monoclonal Ab to Fas may stimulate T-cells under certain conditions (Alderson et al., J Exp. Med. 178:2231(1993)).

Fas antigen is a cell surface protein of relative MW of 45 Kd. Both human and murine genes for Fas have been cloned by Watanabe-Fukunaga et al., (J. Immunol. 148:1274(1992)) and Itoh et al. (Cell 66:233(1991)). The proteins encoded by these genes are both transmembrane proteins with structural homology to the Nerve Growth Factor/Tumor Necrosis Factor receptor superfamily, which includes two TNF receptors, the low affinity Nerve Growth Factor receptor and the $LT_\beta$ receptor CD40, CD27, CD30, and OX40.

Recently the Fas ligand has been described (Suda et al., Cell 75:1169(1993)). The amino acid sequence indicates that Fas ligand is a type II transmembrane protein belonging to the TNF family. Fas ligand is expressed in splenocytes and thymocytes. The purified Fas ligand has a MW of 40 kd.

Recently, it has been demonstrated that Fas/Fas ligand interactions are required for apoptosis following the activation of T-cells (Ju et al., Nature 373:444(1995); Brunner et al., Nature 373:441(1995)). Activation of T-cells induces both proteins on the cell surface. Subsequent interaction between the ligand and receptor results in apoptosis of the cells. This supports the possible regulatory role for apoptosis induced by Fas/Fas ligand interaction during normal immune responses.

The polypeptide of the present invention has been identified as a novel member of the TNF ligand super-family based on structural and biological similarities.

Clearly, there is a need for factors that regulate activation, and differentiation of normal and abnormal cells. There is a need, therefore, for identification and characterization of such factors that modulate activation and differentiation of cells, both normally and in disease states. In particular, there is a need to isolate and characterize additional Fas ligands that control apoptosis for the treatment of autoimmune disease, graft versus host disease, rheumatoid arthritis and lymphadenopathy.

SUMMARY OF THE INVENTION

The present invention provides isolated nucleic acid molecules comprising a polynucleotide encoding the AIM II polypeptide having the amino acid sequence shown in FIGS. 1A and B (SEQ ID NO:2) or the amino acid sequence encoded by the cDNA clone deposited in a bacterial host as ATCC Deposit Number 97689 on Aug. 22, 1996. The present invention also provides isolated nucleic acid molecules comprising a polynucleotide encoding the AIM II polypeptide having the amino acid sequence shown in FIGS. 1C and D (SEQ ID NO:39) or the amino acid sequence encoded by the cDNA clone deposited in a bacterial host as ATCC Deposit Number 97483 on Mar. 15, 1996.

The present invention also relates to recombinant vectors, which include the isolated nucleic acid molecules of the present invention, and to host cells containing the recombinant vectors, as well as to methods of making such vectors and host cells and for using them for production of AIM II polypeptides or peptides by recombinant techniques.

The invention further provides an isolated AIM II polypeptide having an amino acid sequence encoded by a polynucleotide described herein.

As used herein the term "AIM II" polypeptide includes membrane-bound proteins (comprising a cytoplasmic domain, a transmembrane domain, and an extracellular domain) as well as truncated proteins that retain the AIM II polypeptide activity. In one embodiment, soluble AIM II polypeptides comprise all or part of the extracellular domain of an AIM II protein, but lack the transmembrane region that would cause retention of the polypeptide on a cell membrane. Soluble AIM II may also include part of the transmembrane region or part of the cytoplasmic domain or other sequences, provided that the soluble AIM II protein is capable of being secreted. A heterologous signal peptide can be fused to the N-terminus of the soluble AIM II polypeptide such that the soluble AIM II polypeptide is secreted upon expression.

The invention also provides for AIM II polypeptides, particularly human AIM-II polypeptides, which may be employed to treat afflictions such as lymphadenopathy, rheumatoid arthritis, autoimmune disease, graft versus host disease, IgE-mediated allergic reactions, anaphylaxis, adult respiratory distress syndrome, Crohn's disease, allergic asthma, acute lymphoblastic leukemia (ALL), non-Hodgkin's lymphoma (NHL), and Graves' disease. These polypeptides of the invention may also be used to stimulate peripheral tolerance, destroy some transformed cell lines, mediate cell activation and proliferation and are functionally linked as primary mediators of immune regulation and inflammatory response.

The invention further provides compositions comprising an AIM II polynucleotide or an AIM II polypeptide for administration to cells in vitro, to cells ex vivo and to cells in vivo, or to a multicellular organism. In certain particularly preferred embodiments of this aspect of the invention, the compositions comprise an AIM II polynucleotide for expression of an AIM II polypeptide in a host organism for treatment of disease. Particularly preferred in this regard is expression in a human patient for treatment of a dysfunction associated with aberrant endogenous activity of an AIM II.

The present invention also provides a screening method for identifying compounds capable of enhancing or inhibiting a cellular response induced by AIM II, which involves contacting cells which express AIM II with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

In another aspect, a screening assay for AIM II agonists and antagonists is provided. The antagonists may be employed to prevent septic shock, inflammation, cerebral malaria, activation of the HIV virus, graft-host rejection, bone resorption, and cachexia (wasting or malnutrition).

In a further aspect of the invention, AIM II may be used to treat rheumatoid arthritis (RA) by inhibiting the increase in angiogenesis or increase in endothelial cell proliferation required to sustain an invading pannus in bone and cartilage as is often observed in RA.

In an additional aspect of the invention, AIM II may be used to inhibit or activate a cellular response mediated by a cellular receptor (e.g., LT-β-R, TR2, CD27, and TRANK) by either inhibiting the binding of a ligand to the receptor or by binding to the receptor and activating a receptor mediated cellular response.

An additional aspect of the invention is related to a method for treating an individual in need of an increased level of AIM II activity in the body comprising administering to such an individual a composition comprising a therapeutically effective amount of an isolated AIM II polypeptide of the invention or an agonist thereof.

A still further aspect of the invention is related to a method for treating an individual in need of a decreased level of AIM II activity in the body comprising, administering to such an individual a composition comprising a therapeutically effective amount of an AIM II antagonist.

BRIEF DESCRIPTION OF THE FIGURES

FIGS. 1A and B show the nucleotide (SEQ ID NO:1) and deduced amino acid (SEQ ID NO:2) sequences of AIM II. The protein has a deduced molecular weight of about 26.4 kDa. The predicted Transmembrane Domain of the AIM II protein is underlined.

FIGS. 1C and D show the nucleotide (SEQ ID NO:38) and deduced amino acid (SEQ ID NO:39) sequences of a partial AIM II cDNA that was also obtained.

FIGS. 2A–F show the regions of similarity between the amino acid sequences of the AIM II (SEQ ID NO:2) protein and human TNF-α (SEQ ID NO:3), human TNF-β (SEQ ID NO:4), human lymphotoxin (SEQ ID NO:5) and human Fas Ligand (SEQ ID NO:6), and also shows the Majority sequence (SEQ ID NO:56).

FIG. 11 shows the nucleotide sequence of the regulatory elements of the pHE promoter (SEQ ID NO:51). The two lac operator sequences, the Shine-Delgarno sequence (S/D), and the terminal HindIII and NdeI restriction sites (italicized) are indicated.

FIGS. 14A through 14F show an alignment of the amino acid sequence of the AIM II polypeptide shown in SEQ ID NO:39 to the amino acid sequences of human TNFα (SEQ ID NO:3), human TNFβ (SEQ ID NO:4), human lymphotoxin (SEQ ID NO:5), and human Fas Ligand (SEQ ID NO:6) by the Clustal Method with PAM250 Weight Residue Table.

DETAILED DESCRIPTION

Figure 3A:
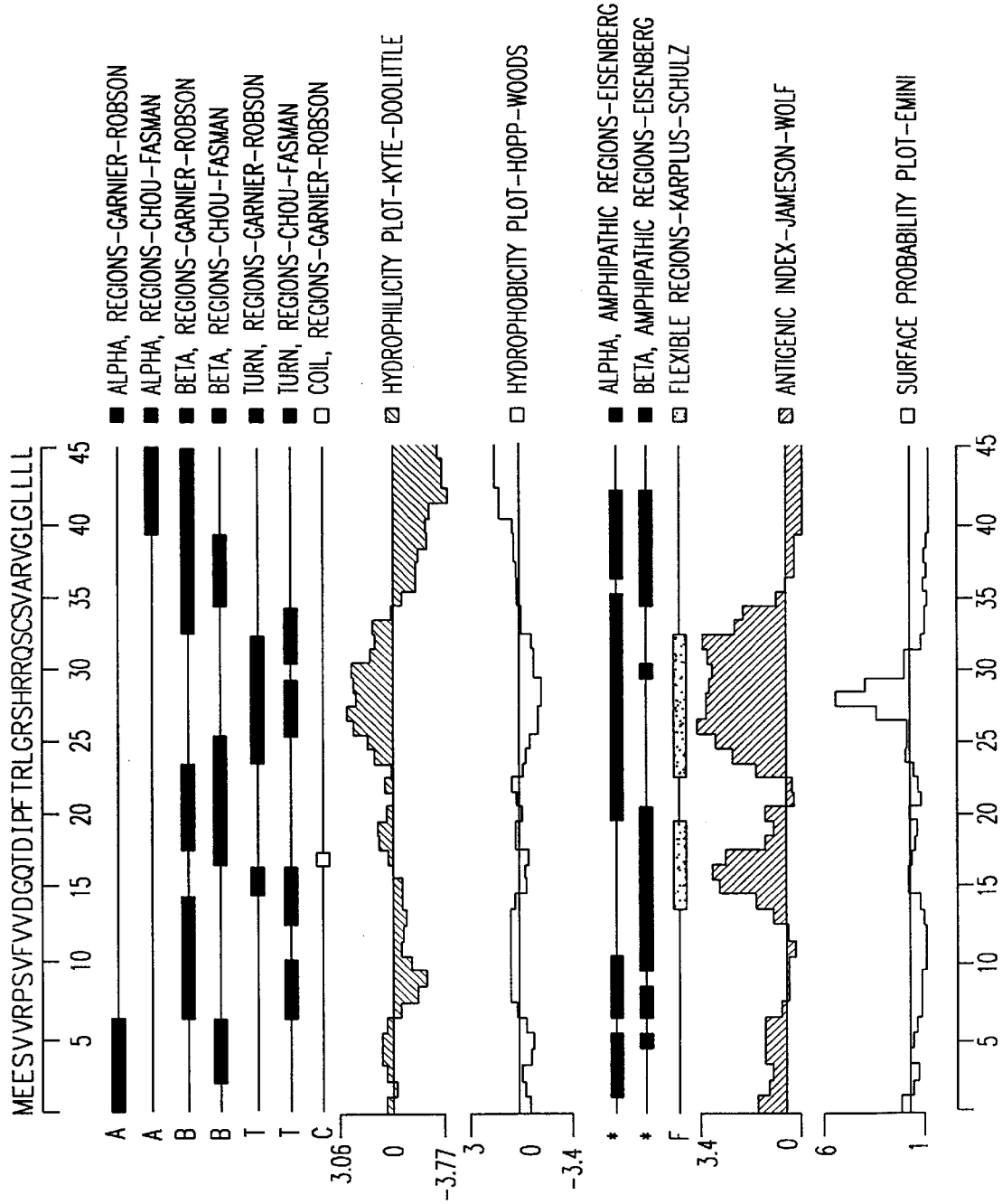
FIGS. 3A–F show an analysis of the AIM II amino acid sequence. Alpha, beta, turn and coil regions; hydrophilicity and hydrophobicity; amphipathic regions; flexible regions; antigenic index and surface probability are shown. In the "Antigenic Index-Jameson-Wolf" graph, about amino acid residues 13–20, 23–36, 69–79, 85–94, 167–178, 184–196, 221–233 in FIGS. 1A and B (SEQ ID NO:2) correspond to the shown highly antigenic regions of the AIM II protein.
Figure 3B:
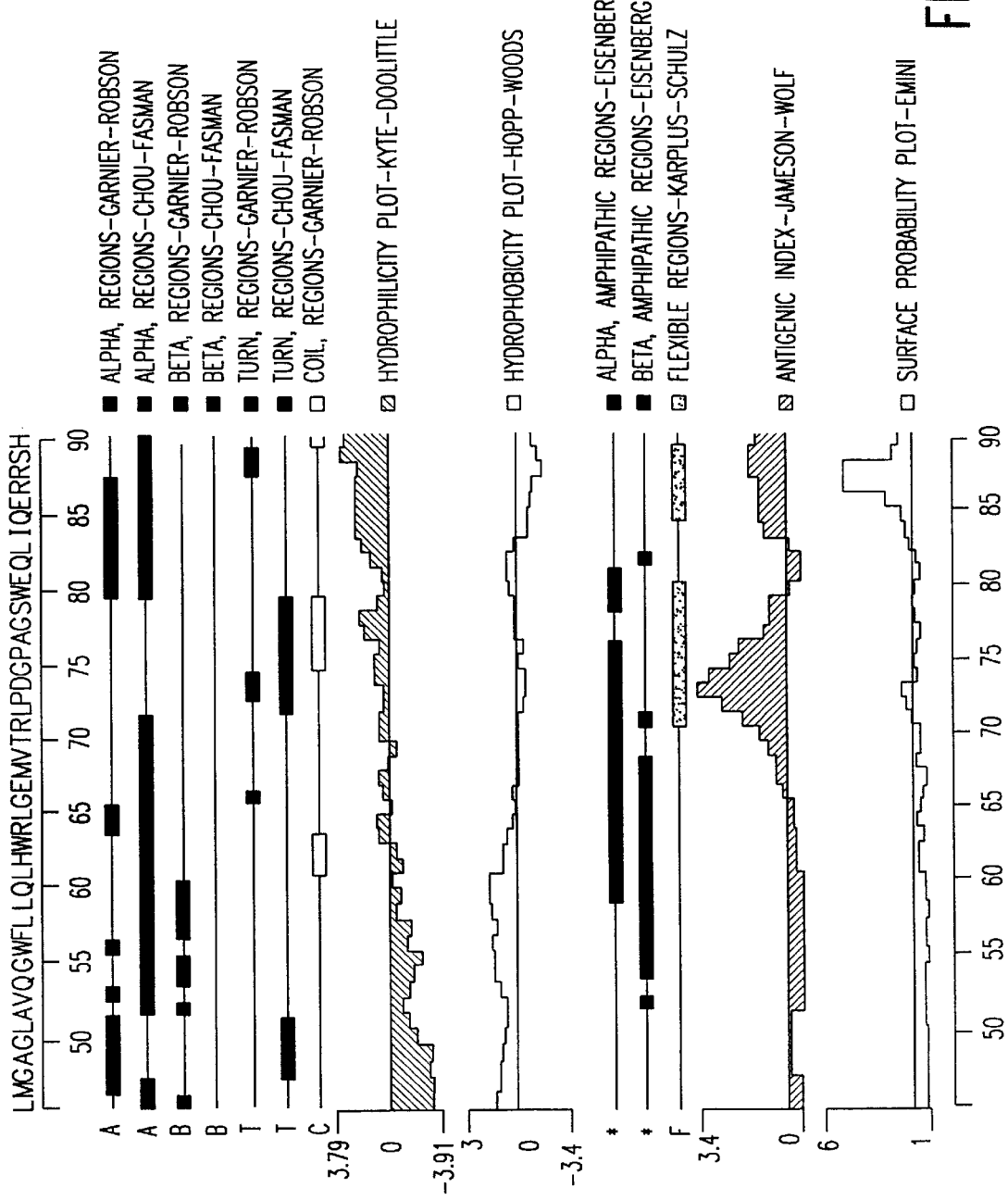
Figure 3C:
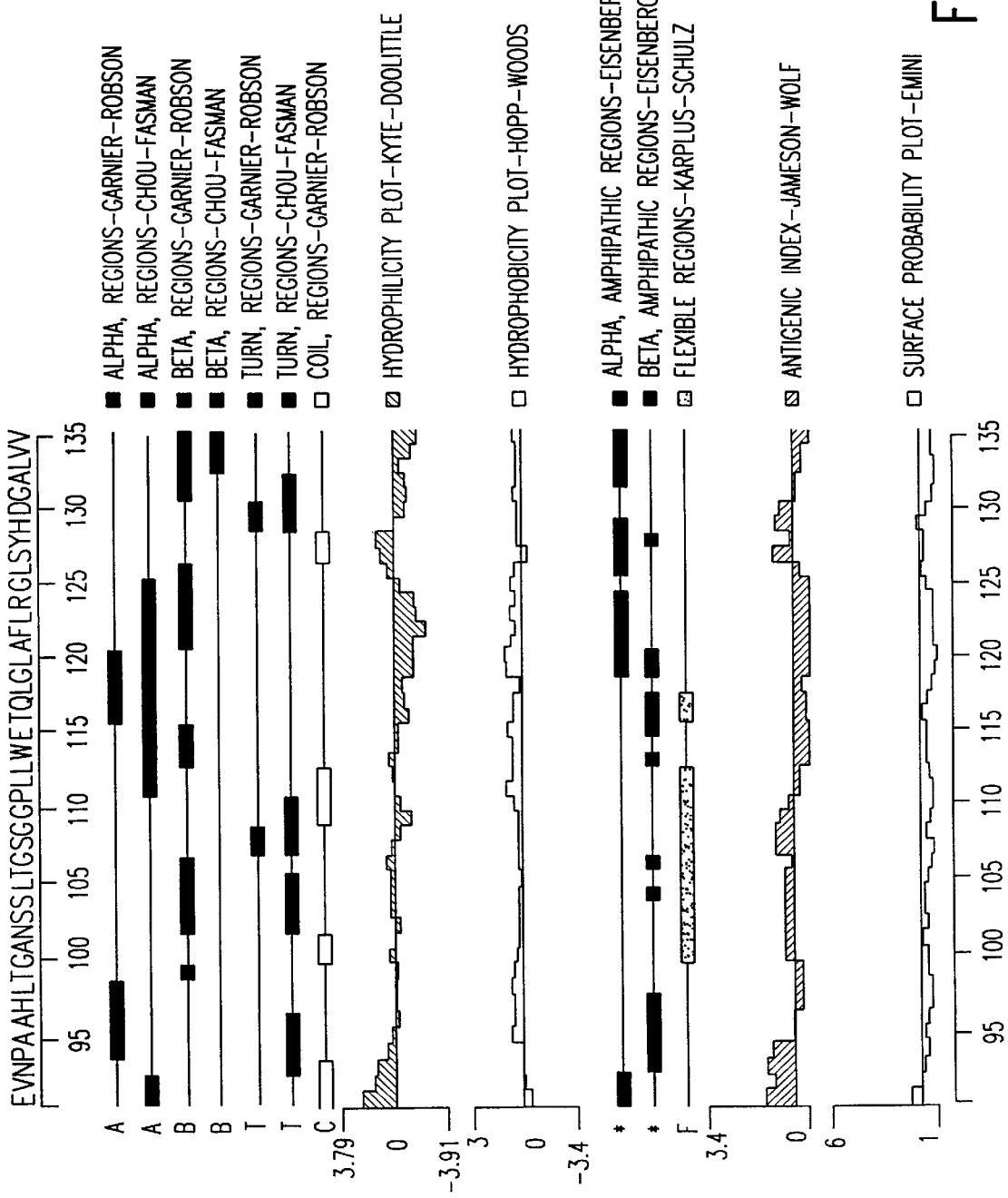
Figure 3D:
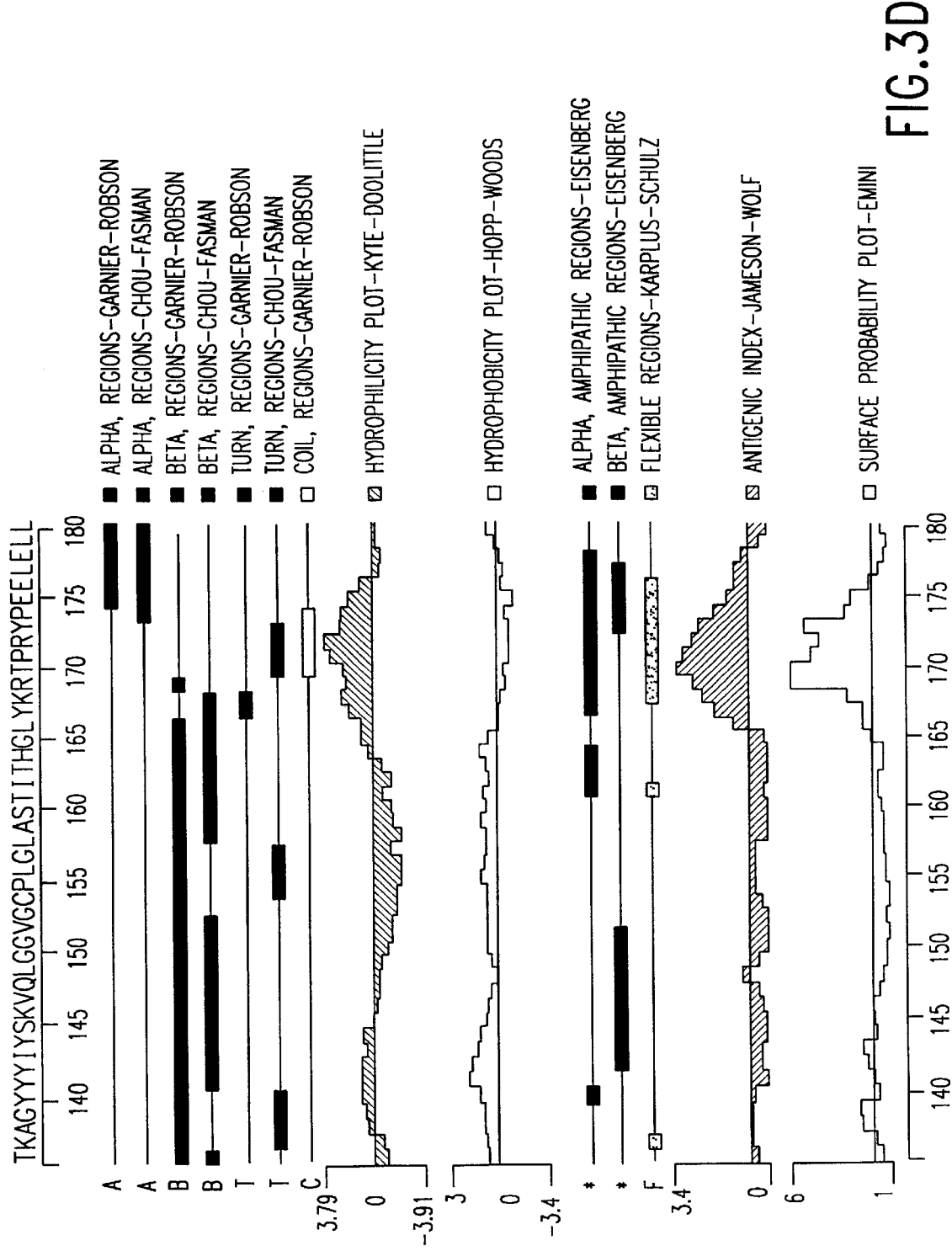
Figure 3E:
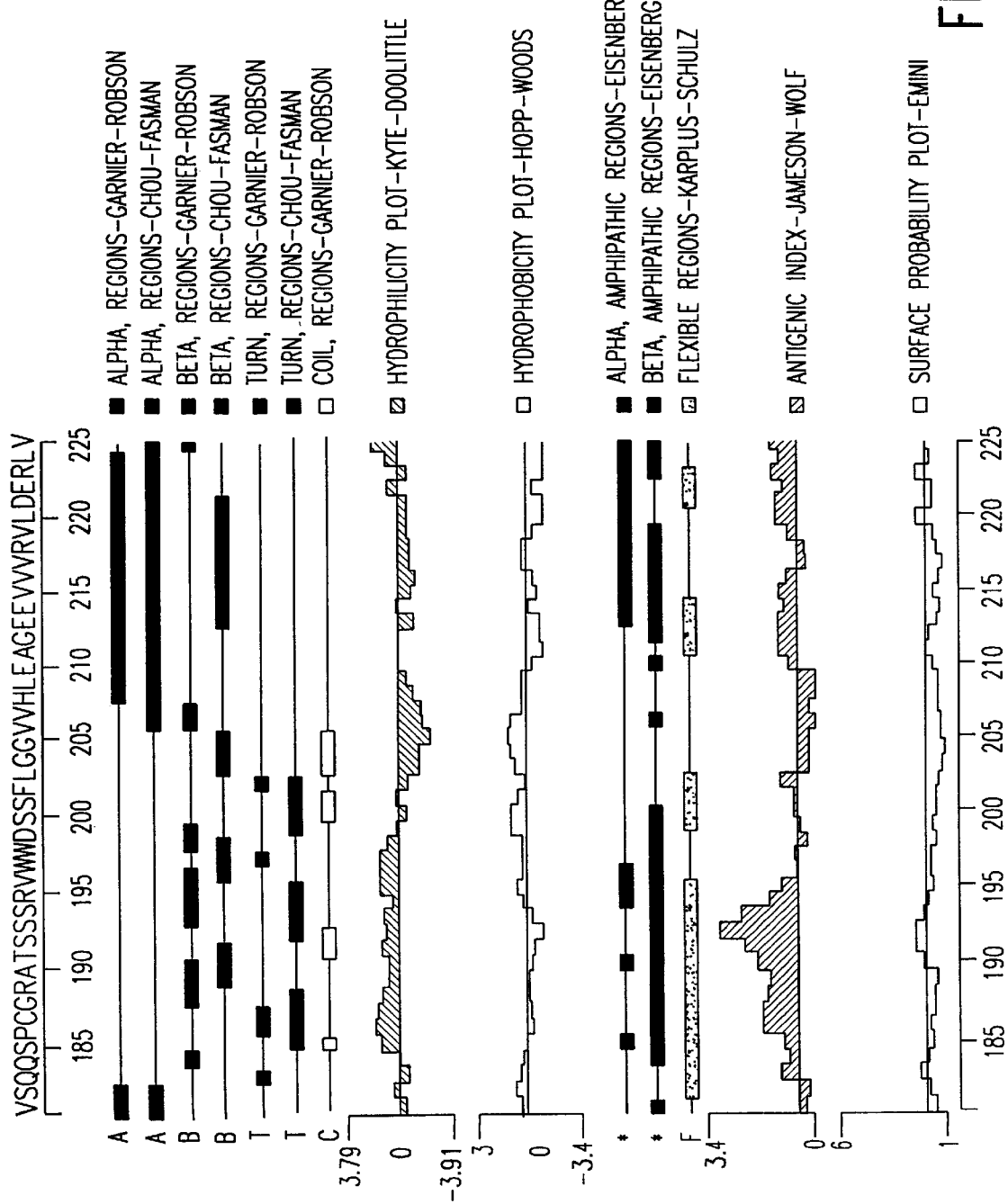
Figure 3F:
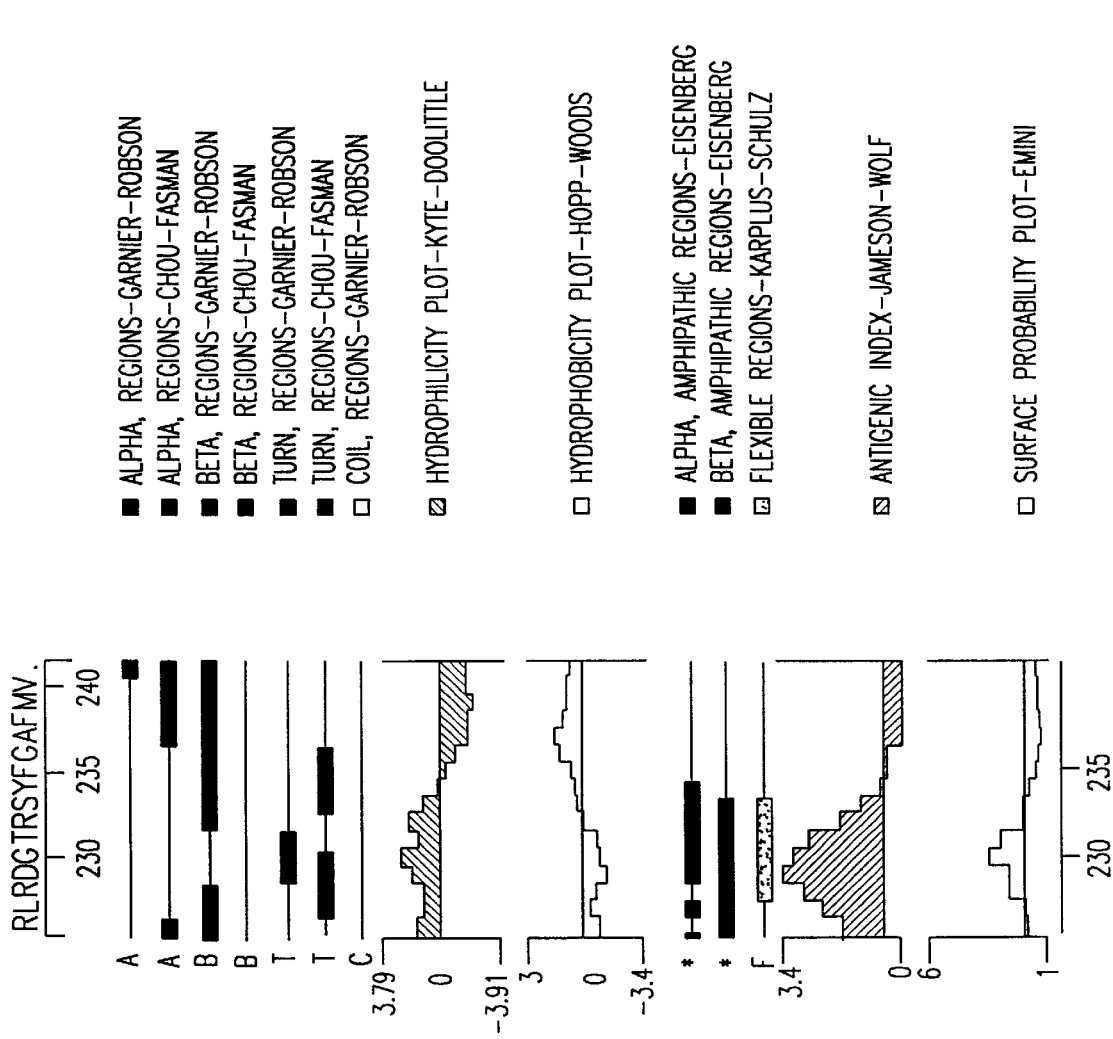

The present invention provides isolated nucleic acid molecules comprising apolynucleotide encoding an AIM II polypeptide having the amino acid sequence shown in FIGS. 1A and B (SEQ ID NO:2), which was determined by sequencing a cloned cDNA. The AIM II protein of the present invention shares sequence homology with human TNF-α (SEQ ID NO:3), human TNF-β (SEQ ID NO:4), human lymphotoxin (SEQ ID NO:5) and human Fas Ligand (SEQ ID NO:6) (FIGS. 2A through 2F). The nucleotide sequence shown in FIGS. 1A and B (SEQ ID NO:1) were obtained by sequencing the a cDNA clone, which was deposited on Aug. 22, 1996 at the American Type Culture Collection, 10801 University Blvd., Manassas, Va. 20110–2209, USA, and given accession number 97689. The deposited clone is contained in the pBluescript SK(−) plasmid (Stratagene, La Jolla, Calif.). The nucleotide sequence shown in FIGS. 1C and D was obtained by sequencing the a cDNA clone, which was deposited on Mar. 15, 1996 at the American Type Culture Collection, 10801 University Blvd., Manassas, Va. 20110–2209, USA, and given accession number 97483.

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIGS. 1A and B, a nucleic acid molecule of the present invention encoding an AIM II polypeptide may be obtained using standard cloning and screening procedures, such as those for cloning cDNAs using mRNA as starting material. Illustrative of the invention, the nucleic acid molecule described in FIGS. 1A and B (SEQ ID NO:1) was discovered in a cDNA library derived from human macrophage ox LDL (HMCCB64). The gene was also identified in cDNA libraries from activated T-cells (HT4CC72). The determined nucleotide sequence of the AIM II cDNA of FIGS. 1A and B (SEQ ID NO:1) contains an open reading frame encoding a protein of 240 amino acid residues, with an initiation codon at positions 49–51 of the nucleotide sequence in FIGS. 1A and B (SEQ ID NO:1), an extracellular domain comprising amino acid residues from about 60 to about 240 in FIGS. 1A and B (SEQ ID NO:2), a transmembrane domain comprising amino acid residues from about 37 to about 59 in FIGS. 1A and B (SEQ ID NO:2), a intracellular domain comprising amino acid residues from about 1 to about 36 in FIGS. 1A and B (SEQ ID NO:2) and a deduced molecular weight of about 26.4 kDa. The AIM II protein shown in FIGS. 1A and B (SEQ ID NO:2) is about 27% identical and about 51% similar to the amino acid sequence of human Fas Ligand (FIGS. 2A through 2F) and is about 26% identical and about 47% similar to the amino acid sequence of human TNF-α (FIGS. 2A through 2F). TNF-ligand like molecules function as dimers, given that AIM II is homologous to TNF-ligand like molecules, it is likely that it also functions as a homodimer.

As one of ordinary skill would appreciate, due to the possibilities of sequencing errors discussed above, the predicted AIM II polypeptide encoded by the deposited cDNA comprises about 240 amino acids, but may be anywhere in the range of 230–250 amino acid. It will further be appreciated that, depending on the criteria used, concerning the exact "address" of the extracelluar, intracellular and transmembrane domains of the AIM II polypeptide differ slightly. For example, the exact location of the AIM II extracellular domain in FIGS. 1A and B (SEQ ID NO:2) may vary slightly (e.g., the address may "shift" by about 1 to 5 residues) depending on the criteria used to define the domain.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) shown in FIGS. 1A and B (SEQ ID NO:1) or FIGS. 1C and D (SEQ ID NO:38); DNA molecules comprising the coding sequence for the AIM II protein shown in FIGS. 1A and B (SEQ ID NO:2) or FIGS. 1C and D (SEQ ID NO:39); and DNA molecules which comprise a sequence substantially different from those described above but which, due to the degeneracy of the genetic code, still encode the AIM II protein. Of course, the genetic code is well known in the art. Thus, it would be routine for one skilled in the art to generate such degenerate variants.

In addition, the invention provides a nucleic acid molecule having a nucleotide sequence related to a portion of SEQ ID NO:1 which has been determined from the following related cDNA clone: HT4CC72R (SEQ ID NO:20).

In another aspect, the invention provides isolated nucleic acid molecules encoding the AIM II polypeptide having an amino acid sequence encoded by the cDNA clone contained in the plasmid deposited as ATCC Deposit No. 97689 on Aug. 22, 1996 or by the cDNA clone contained in the plasmid deposited as ATCC Deposit No. 97483 on Mar. 15, 1996. Preferably, this nucleic acid molecule will encode the polypeptide encoded by the above-described deposited cDNA clone. The invention further provides an isolated nucleic acid molecule having the nucleotide sequence shown in FIGS. 1A and B (SEQ ID NO:1) or FIGS. 1C and D (SEQ ID NO:38) or the nucleotide sequence of the AIM II cDNA contained in the above-described deposited clones, or a nucleic acid molecule having a sequence complementary to one of the above sequences. Such isolated molecules, particularly DNA molecules, are useful as probes for gene mapping, by in situ hybridization with chromosomes, and for detecting expression of the AIM II gene in human tissue, for instance, by Northern blot analysis.

The present invention is further directed to fragments of the isolated nucleic acid molecules described herein. By a fragment of an isolated nucleic acid molecule having the nucleotide sequence of the deposited cDNA or the nucleotide sequence shown in FIGS. 1A and B (SEQ ID NO:1) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125 or 1150 nt in length are also useful according to the present invention as are fragments corresponding to most, if not all, of the nucleotide sequence of the deposited cDNA or as shown in FIGS. 1A and B (SEQ ID NO:1). By a fragment at least 20 nt in length, for example, is intended fragments which include 20 or more contiguous bases from the nucleotide sequence of the deposited cDNA or the nucleotide sequence as shown in FIGS. 1A and B (SEQ ID NO:1).

Preferred nucleic acid fragments of the present invention include nucleic acid molecules encoding epitope-bearing portions of the AIM II protein. In particular, such nucleic acid fragments of the present invention include nucleic acid molecules encoding: a polypeptide comprising amino acid residues from about 13 to about 20 in FIGS. 1A and B (SEQ ID NO:2); a polypeptide comprising amino acid residues from about 23 to about 36 in FIG. 1 (SEQ ID NO:2); a polypeptide comprising amino acid residues from about 69 to about 79 in FIGS. 1A and B (SEQ ID NO:2); a polypeptide comprising amino acid residues from about 85 to about 94 in FIGS. 1A and B (SEQ ID NO:2);a polypeptide comprising amino acid residues from about 167 to about 178 in FIGS. 1A and B (SEQ ID NO:2);a polypeptide comprising amino acid residues from about 184 to about 196 in FIGS. 1A and B (SEQ ID NO:2); and a polypeptide comprising amino acid residues from about 221 to about 233 in FIGS. 1A and B (SEQ ID NO:2). The inventors have determined that the above polypeptide fragments are antigenic regions of the AIM II protein. Methods for determining other such epitope-bearing portions of the AIM II protein are described in detail below.

AIM II polynucleotides may be used in accordance with the present invention for a variety of applications, particularly those that make use of the chemical and biological properties of the AIM II. Among these applications in autoimmune disease and aberrant cellular proliferation. Additional applications relate to diagnosis and to treatment of disorders of cells, tissues, and organisms.

This invention is also related to the use of the AIM II polynucleotides to detect complementary polynucleotides such as, for example, as a diagnostic reagent. Detection of a mutated form of an AIM II associated with a dysfunction will provide a diagnostic tool that can add or define a diagnosis of a disease or susceptibility to disease which results from under-expression, over-expression or altered expression of AIM II, such as, for example, autoimmune diseases. The polynucleotide encoding the AIM II may also be employed as a diagnostic marker for expression of the polypeptide of the present invention.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit 97689. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIGS. 1A and B (SEQ ID NO:1)).

Of course, a polynucleotide which hybridizes only to a poly A sequence (such as the 3' terminal poly(A) tract of the AIM II cDNA shown in FIGS. 1A and B (SEQ ID NO:1)), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode an AIM II polypeptide may include, but are not limited to those encoding the amino acid sequence of the polypeptide, by itself; the coding sequence for the polypeptide and additional sequences, such as those encoding a leader or secretory sequence, such as a pre-, or pro- or prepro- protein sequence; the coding sequence of the polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al, *Proc. Natl. Acad Sci. USA* 86:821–824(1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37:767(1984). As discussed below, other such fusion proteins include the AIM II fused to Fc at the N- or C-terminus.

Nucleic acid molecules according to the present invention further include those encoding the full-length AIM-II polypeptide lacking the N-terminal methionine.

The present invention further relates to variants of the nucleic acid molecules of the present invention, which encode portions, analogs or derivatives of the AIM II protein. Variants may occur naturally, such as a natural allelic variant. By an "allelic variant" is intended one of several alternate forms of a gene occupying a given locus on a chromosome of an organism. Genes II, Lewin, B., ed., John Wiley & Sons, New York (1985). Non-naturally occurring variants may be produced using art-known mutagenesis techniques.

Such variants include those produced by nucleotide substitutions, deletions or additions which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the AIM II protein or portions thereof. Also especially preferred in this regard are conservative substitutions.

Further embodiments of the invention include isolated nucleic acid molecules comprising apolynucleotide having anucleotide sequence at least 90% identical, and more preferably at least 95%, 96%, 97%, 98% or 99% identical to (a) a nucleotide sequence encoding the AIM II polypeptide having the complete amino acid sequence in FIGS. 1A and B (SEQ ID NO:2); (b) a nucleotide sequence encoding the AIM II polypeptide having the amino acid sequence in FIGS. 1A and B (SEQ ID NO:2), but lacking the N-terminal methionine; (c) a nucleotide sequence encoding the AIM II polypeptide having the complete amino acid sequence encoded by the cDNA clone contained in ATCC Deposit No. 97689; (d) a nucleotide sequence encoding the AIM II polypeptide extracellular domain; (e) a nucleotide sequence encoding the AIM II polypeptide transmembrane domain; (f) a nucleotide sequence encoding the AIM II polypeptide intracellular domain; (g) a nucleotide sequence encoding a soluble AIM II polypeptide having the extracellular and intracellular domains but lacking the transmembrane domain; and (h) a nucleotide sequence complementary to any of the nucleotide sequences in (a), (b), (c), (d), (e), (f) or (g) above.

By a polynucleotide having a nucleotide sequence at least, for example, 95% "identical" to a reference nucleotide sequence encoding an AIM II polypeptide is intended that the nucleotide sequence of the polynucleotide is identical to the reference sequence except that the polynucleotide sequence may include up to five point mutations per each 100 nucleotides of the reference nucleotide sequence encoding the AIM II polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIGS. 1A and B or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2: 482–489(1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the AIM II polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown in FIGS. 1A and B, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* 6:237–245(1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix= Unitary, k-tuple=4, Mismatch Penalty=1, Joining Penalty= 30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a match/ alignment of the first 10 bases at the 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

The present application is directed to nucleic acid molecules at least 90%, 95%, 96%, 97%, 98% or 99% identical to the nucleic acid sequence shown in FIGS. 1A and B (SEQ ID NO:1) or to the nucleic acid sequence of the deposited cDNA, irrespective of whether they encode a polypeptide having AIM II activity. This is because even where a particular nucleic acid molecule does not encode a polypeptide having AIM II activity, one of skill in the art would still know how to use the nucleic acid molecule, for instance, as a hybridization probe or a polymerase chain reaction (PCR) primer. Uses of the nucleic acid molecules of the present invention that do not encode a polypeptide having AIM II activity include, inter alia, (1) isolating the AIM II gene or allelic variants thereof in a cDNA library; (2) in situ hybridization (e.g., "FISH") to metaphase chromosomal spreads to provide precise chromosomal location of the AIM II gene, as described in Verma et al., *Human Chromosomes: A Manual of Basic Techniques*, Pergamon Press, New York (1988); and (3) Northern Blot analysis for detecting AIM II mRNA expression in specific tissues.

Preferred, however, are nucleic acid molecules having sequences at least 90%, 95%, 96%, 97%, 98% or 99% identical to the nucleic acid sequence shown in FIGS. 1A and B (SEQ ID NO:1) or to the nucleic acid sequence of the deposited cDNA which do, in fact, encode a polypeptide having AIM II protein activity. By "a polypeptide having AIM II activity" is intended polypeptides exhibiting activity similar, but not necessarily identical, to an activity of the AIM II protein of the invention, as measured in a particular biological assay. For example, AIM II protein cytotoxic activity can be measured using propidium iodide staining to demonstrate apoptosis as described by Zarres et al., *Cell* 70: 31–46(1992). Alternatively, AIM II induced apoptosis can also be measured using TUNEL staining as described by Gavierli et al., *J Cell. Biol.* 119: 493–501(1992).

Briefly, the propidium iodide staining is performed as follows. Cells either from tissue or culture are fixed in formaldehyde, cut into frozen sections and stained with propidium iodide. The cell nuclei are visualized by propidium iodide using confocal fluorescent microscopy. Cell death is indicated by pyknotic nuclei (chromosome clumping, shrinking and/or fragmentation of nuclei).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIGS. 1A and B (SEQ ID NO:1) will encode a polypeptide "having AIM II protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having AIM II protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310(1990), wherein the authors indicate that proteins are surprisingly tolerant of amino acid substitutions.

AIM II "Knock-Outs" and Homologous Recombination

Endogenous gene expression can also be reduced by inactivating or "knocking out" the gene and/or its promoter using targeted homologous recombination. (e.g., see Smithies et al., *Nature* 317:230–234(1985); Thomas & Capecchi, *Cell* 51:503–512(1987); Thompson et al., *Cell* 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (see, e.g., Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art. The contents of each of the documents recited in this paragraph is herein incorporated by reference in its entirety.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally. Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, e.g., Anderson et al. U.S. Pat. No. 5,399,349; and Mulligan & Wilson, U.S. Pat. No. 5,460,959, each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Vectors and Host Cells

The present invention also relates to vectors which include the isolated DNA molecules of the present invention, host cells which are genetically engineered with the recombinant vectors, and the production of AIM II polypeptides or fragments thereof by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the E. coli lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art.

In addition to the use of expression vectors in the practice of the present invention, the present invention further includes novel expression vectors comprising operator and promoter elements operatively linked to nucleotide sequences encoding a protein of interest. One example of such a vector is pHE4-5 which is described in detail below.

Figure 10:
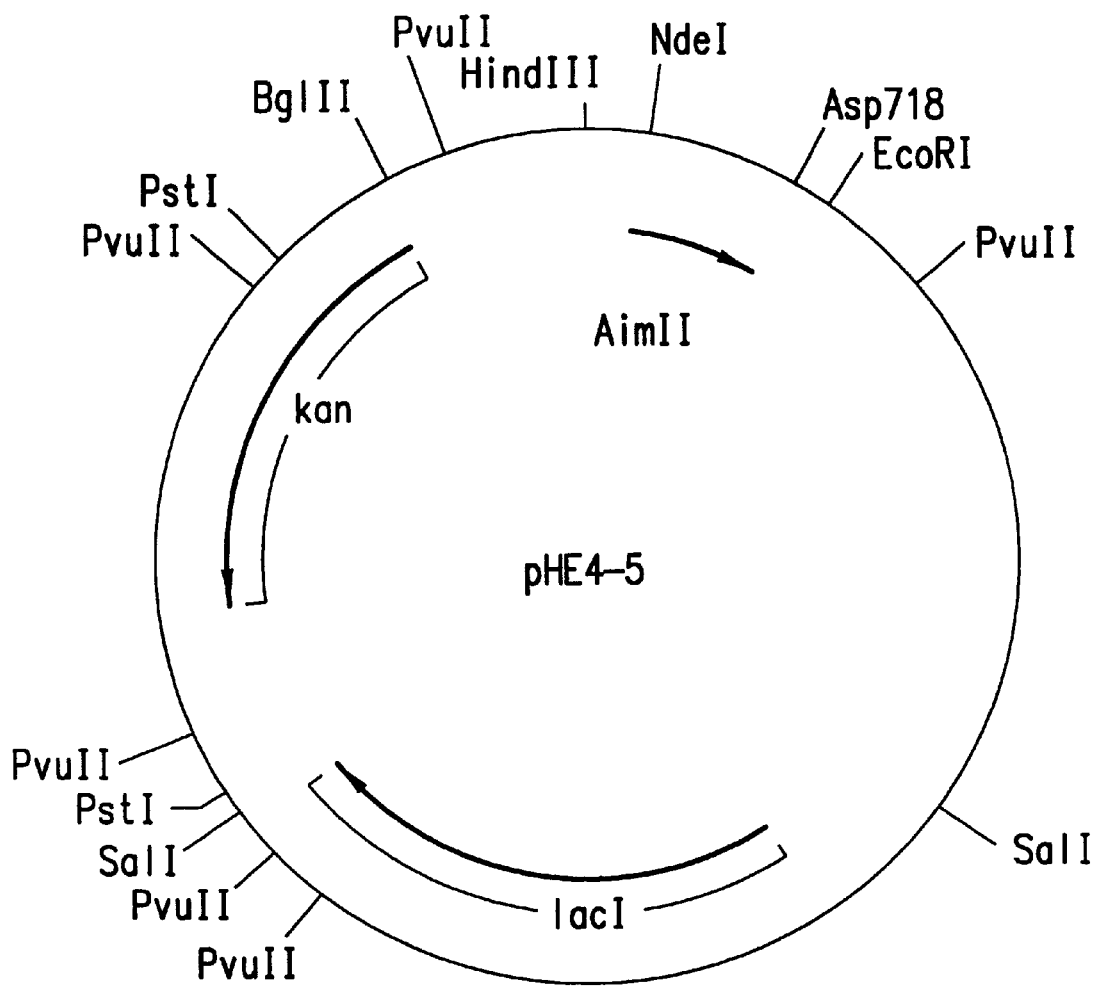
FIG. 10 shows a schematic representation of the pHE4-5 expression vector (SEQ ID NO:50) and the subcloned AIM II cDNA coding sequence. The locations of the kanamycin resistance marker gene, the AIM II coding sequence, the oriC sequence, and the lacIq coding sequence are indicated.

As summarized in FIGS. 10 and 11, components of the pHE4-5 vector (SEQ ID NO:50) include: 1) a neomycin-phosphotransferase gene as a selection marker, 2) an E. coli origin of replication, 3) a T5 phage promoter sequence, 4) two lac operator sequences, 5) a Shine-Delgarno sequence, 6) the lactose operon repressor gene (lacIq). The origin of replication (oriC) is derived from pUC19 (LTI, Gaithersburg, Md.). The promoter sequence and operator sequences were made synthetically. Synthetic production of nucleic acid sequences is well known in the art. Clontech 95/96 Catalog, pages 215–216, Clontech, 1020 East Meadow Circle, Palo Alto, Calif. 94303. A nucleotide sequence encoding AIM II (SEQ ID NO:1), is operatively linked to the promoter and operator by inserting the nucleotide sequence between the NdeI and Asp718 sites of the pHE4-5 vector.

As noted above, the pHE4-5 vector contains a lacIq gene. LacIq is an allele of the lacI gene which confers tight regulation of the lac operator. Amann, E. et al., *Gene* 69:301–315(1988); Stark, M., *Gene* 51:255–267(1987). The lacIq gene encodes a repressor protein which binds to lac operator sequences and blocks transcription of down-stream (i.e., 3') sequences. However, the lacIq gene product dissociates from the lac operator in the presence of either lactose or certain lactose analogs, e.g., isopropyl B-D-thiogalactopyranoside (IPTG). AIM II thus is not produced in appreciable quantities in uninduced host cells containing the pHE4-5 vector. Induction of these host cells by the addition of an agent such as IPTG, however, results in the expression of the AIM II coding sequence.

The promoter/operator sequences of the pHE4-5 vector (SEQ ID NO:51) comprise a T5 phage promoter and two lac operator sequences. One operator is located 5' to the transcriptional start site and the other is located 3' to the same site. These operators, when present in combination with the lacIq gene product, confer tight repression of down-stream sequences in the absence of a lac operon inducer, e.g., IPTG. Expression of operatively linked sequences located downstream from the lac operators may be induced by the addition of a lac operon inducer, such as IPTG. Binding of a lac inducer to the lacIq proteins results in their release from the lac operator sequences and the initiation of transcription of operatively linked sequences. Lac operon regulation of gene expression is reviewed in Devlin, T., Textbook of Biochemistry with Clinical Correlations, 4th Edition (1997), pages 802–807.

The pHE4 series of vectors contain all of the components of the pHE4-5 vector except for the AIM II coding sequence. Features of the pHE4 vectors include optimized synthetic T5 phage promoter, lac operator, and Shine-Delgarno sequences. Further, these sequences are also optimally spaced so that expression of an inserted gene may be tightly regulated and high level of expression occurs upon induction.

Among known bacterial promoters suitable for use in the production of proteins of the present invention include the E. coli lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter.

The pHE4-5 vector also contains a Shine-Delgarno sequence 5' to the AUG initiation codon. Shine-Delgarno sequences are short sequences generally located about 10 nucleotides up-stream (i.e., 5') from the AUG initiation codon. These sequences essentially direct prokaryotic ribosomes to the AUG initiation codon.

Thus, the present invention is also directed to expression vector useful for the production of the proteins of the present invention. This aspect of the invention is exemplified by the pHE4-5 vector (SEQ ID NO:50).

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5-receptor has been fused with Fc portions for the purpose of high-throughput screening assays to identify antagonists of hIL-5. See, D. Bennett et al., *Journal of Molecular Recognition*, Vol. 8:52–58(1995) and K. Johanson et al., *The Journal of Biological Chemistry*, Vol. 270, No. 16:9459–9471(1995).

The AIM II protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., AIM II coding sequence), and/or to include genetic material (e.g., heterologous polynucleotide sequences) that is operably associated with AIM II polynucleotides of the invention, and which activates, alters, and/or amplifies endogenous AIM II polynucleotides. For example, techniques known in the art may be used to operably associate heterologous control regions (e.g., promoter and/or enhancer) and endogenous AIM II polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., *Proc. Natl. Acad. Sci. USA* 86:8932–8935(1989); and Zijlstra et al., *Nature* 342:435–438(1989), the disclosures of each of which are incorporated by reference in their entireties).

Transgenic Non-Human Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., *Appl. Microbiol. Biotechnol.* 40:691–698(1994); Carver et al., *Biotechnology* (NY) 11:1263–1270(1993); Wright et al., *Biotechnology* (NY) 9:830–834(1991); and Hoppe et al., U.S. Pat. No. 4,873,191 (1989)); retrovirus mediated gene transfer into germ lines (Van der Putten et al., *Proc. Natl. Acad Sci., USA* 82:6148–6152(1985)), blastocysts or embryos; gene targeting in embryonic stem cells (Thompson et al., *Cell* 56:313–321(1989)); electroporation of cells or embryos (Lo, *Mol Cell. Biol.* 3:1803–1814(1983)); introduction of the polynucleotides of the invention using a gene gun (see, e.g., Ulmer et al., *Science* 259:1745(1993); introducing nucleic acid constructs into embryonic pleuripotent stem cells and transferring the stem cells back into the blastocyst; and sperm-mediated gene transfer (Lavitrano et al., *Cell* 57:717–723(1989); etc. For a review of such techniques, see Gordon, "Transgenic Animals," *Intl. Rev. Cytol.* 115:171–229(1989), which is incorporated by reference herein in its entirety. Further, the contents of each of the documents recited in this paragraph is herein incorporated by reference in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., *Nature* 380:64–66(1996); Wilmut et al., *Nature* 385:810–813 (1997)), each of which is herein incorporated by reference in its entirety).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., *Proc.*

*Natl. Acad. Sci. USA* 89:6232–6236(1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., *Science* 265:103–106(1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic and "knock-out" animals of the invention have uses which include, but are not limited to, animal model systems useful in elaborating the biological function of AIM II polypeptides, studying conditions and/or disorders associated with aberrant AIM II expression, and in screening for compounds effective in ameliorating such conditions and/or disorders.

AIM II Polypeptides and Fragments

The invention further provides an isolated AIM II polypeptide having the amino acid sequence encoded by the deposited cDNA, or the amino acid sequence in FIGS. 1A and B (SEQ ID NO:2), or a peptide or polypeptide comprising a portion of the above polypeptides.

It will be recognized in the art that some amino acid sequences of the AIM II polypeptide can be varied without significant effect of the structure or function of the protein. If such differences in sequence are contemplated, it should be remembered that there will be critical areas on the protein which determine activity.

Thus, the invention further includes variations of the AIM II polypeptide which show substantial AIM II polypeptide activity or which include regions of AIM II protein such as the protein portions discussed below. Such mutants include deletions, insertions, inversions, repeats, and type substitutions. As indicated above, guidance concerning which amino acid changes are likely to be phenotypically silent can be found in Bowie, J. U., et al., "Deciphering the Message in Protein Sequences: Tolerance to Amino Acid Substitutions," *Science* 247:1306–1310(1990).

Thus, the fragment, derivative or analog of the polypeptide of FIGS. 1A and B (SEQ ID NO:2), or that encoded by the deposited cDNA, may be (i) one in which one or more of the amino acid residues (e.g., 3, 5, 8, 10, 15 or 20) are substituted with a conserved or non-conserved amino acid residue (preferably a conserved amino acid residue) and such substituted amino acid residue may or may not be one encoded by the genetic code, or (ii) one in which one or more of the amino acid residues includes a substituent group (e.g., 3, 5, 8, 10, 15 or 20), or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the AIM II protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845(1987); Cleland et al. *Crit. Rev. Therapeutic Drug Carrier Systems* 10:307–377(1993)).

The replacement of amino acids can also change the selectivity of binding to cell surface receptors. Ostade et al., *Nature* 361:266–268(1993) describes certain mutations resulting in selective binding of TNF-α to only one of the two known types of TNF receptors. Thus, the AIM II receptor of the present invention may include one or more (e.g., 3, 5, 8, 10, 15 or 20) amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |

TABLE 1-continued

Conservative Amino Acid Substitutions.

| | |
|---|---|
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above. Generally speaking, the number of substitutions for any given AIM-II polypeptide will not be more than 50, 40, 30, 25, 20, 15, 10, 5 or 3.

Amino acids in the AIM II protein of the present invention that are essential for function can be identified by methods known in the art, such as site-directed mutagenesis or alanine-scanning mutagenesis (Cunningham and Wells, *Science* 244:1081–1085(1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J Mol. Biol.* 224:899–904(1992) and de Vos et al. *Science* 255:306–312 (1992)).

Amino and Carboxy Terminal Deletions

Also included in the present invention are amino terminal deletion mutants. Such mutants include those comprising the amino acid sequence shown in SEQ ID NO:2 having a deletion of at least first N-terminal amino acid but not more than the first 114 N-terminal amino acid residues of SEQ ID NO:2. Alternatively, the deletion will include at least the first 35 N-terminal amino acid residues but not more than the first 114 N-terminal amino acid residues of SEQ ID NO:2. Alternatively, the deletion will include at least the first 59 N-terminal amino acid residues but not more than the first 114 N-terminal amino acid residues of SEQ ID NO:2. Alternatively, the deletion will include at least the first 67 N-terminal amino acid residues but not more than the first 114 N-terminal amino acid residues of SEQ ID NO:2. Alternatively, the deletion will include at least the first 68 N-terminal amino acid residues but not more than the first 114 N-terminal amino acid residues of SEQ ID NO:2. Alternatively, the deletion will include at least the first 73 N-terminal amino acid residues but not more than the first 114 N-terminal amino acid residues of SEQ ID NO:2. Alternatively, the deletion will include at least the first 82 N-terminal amino acid residues but not more than the first 114 N-terminal amino acid residues of SEQ ID NO:2. Alternatively, the deletion will include at least the first 100 N-terminal amino acid residues but not more than the first 114 N-terminal amino acid residues of SEQ ID NO:2.

In addition to the ranges of N-terminal deletion mutants described above, the present invention is also directed to all combinations of the above described ranges. For example, the deletions of at least the first 59 N-terminal amino acid residues but not more than the first 67 N-terminal amino acid residues of SEQ ID NO:2; deletions of at least the first 59 N-terminal amino acid residues but not more than the first 68 N-terminal amino acid residues of SEQ ID NO:2; deletions of at least the first 59 N-terminal amino acid residues but not more than the first 73 N-terminal amino acid residues of SEQ ID NO:2; deletions of at least the first 59 N-terminal amino acid residues but not more than the first 82 N-terminal amino acid residues of SEQ ID NO:2; deletions of at least the first 59 N-terminal amino acid residues but not more than the first 100 N-terminal amino acid residues of SEQ ID NO:2; deletions of at least the first 67 N-terminal amino acid residues but not more than the first 73 N-terminal amino acid residues of SEQ ID NO:2; deletions of at least the first 67 N-terminal amino acid residues but not more than the first 82 N-terminal amino acid residues of SEQ ID NO:2; deletions of at least the first 67 N-terminal amino acid residues but not more than the first 100 N-terminal amino acid residues of SEQ ID NO:2; deletions of at least the first 68 N-terminal amino acid residues but not more than the first 73 N-terminal amino acid residues of SEQ ID NO:2; deletions of at least the first 68 N-terminal amino acid residues but not more than the first 82 N-terminal amino acid residues of SEQ ID NO:2; deletions of at least the first 68 N-terminal amino acid residues but not more than the first 100 N-terminal amino acid residues of SEQ ID NO:2; deletions of at least the first 73 N-terminal amino acid residues but not more than the first 82 N-terminal amino acid residues of SEQ ID NO:2; deletions of at least the first 73 N-terminal amino acid residues but not more than the first 100 N-terminal amino acid residues of SEQ ID NO:2; deletions of at least the first 82 N-terminal amino acid residues but not more than the first 100 N-terminal amino acid residues of SEQ ID NO:2; etc. etc. etc. . . .

Preferred AIM II polypeptides are shown below (numbering starts with the first amino acid in the protein (Met):

| | |
|---|---|
| Gln(residue 60) to Val(residue 240) | Arg(88) to Val(240) |
| Leu(61) to Val(240) | Ser(89) to Val(240) |
| His(62) to Val(240) | His(90) to Val(240) |
| Trp(63) to Val(240) | Glu(91) to Val(240) |
| Arg(64) to Val(240) | Val(92) to Val(240) |
| Leu(65) to Val(240) | Asn(93) to Val(240) |
| Gly(66) to Val(240) | Pro(94) to Val(240) |
| Glu(67) to Val(240) | Ala(95) to Val(240) |
| Met(68) to Val(240) | Ala(96) to Val(240) |
| Val(69) to Val(240) | His(97) to Val(240) |
| Thr(70) to Val(240) | Leu(98) to Val(240) |
| Arg(71) to Val(240) | Thr(99) to Val(240) |
| Leu(72) to Val(240) | Gly(100) to Val(240) |
| Pro(73) to Val(240) | Ala(101) to Val(240) |
| Asp(74) to Val(240) | Asn(102) to Val(240) |
| Gly(75) to Val(240) | Ser(103) to Val(240) |
| Pro(76) to Val(240) | Ser(104) to Val(240) |
| Ala(77) to Val(240) | Leu(105) to Val(240) |
| Gly(78) to Val(240) | Thr(106) to Val(240) |
| Ser(79) to Val(240) | Gly(107) to Val(240) |
| Trp(80) to Val(240) | Ser(108) to Val(240) |
| Glu(81) to Val(240) | Gly(109) to Val(240) |
| Gln(82) to Val(240) | Gly(110) to Val(240) |
| Leu(83) to Val(240) | Pro(111) to Val(240) |
| Ile(84) to Val(240) | Leu(112) to Val(240) |
| Gln(85) to Val(240) | Leu(113) to Val(240) |
| Glu(86) to Val(240) | Trp(114) to Val(240) |
| Arg(87) to Val(240) | |

Particularly preferred embodiments include the AIM II N-terminal deletions Gln-60 to Val-240 (AIM II (aa 60–240)), Met-68 to Val-240 (AIM II (aa 68–240)), Val-69 to Val-240(AIM II (aa 69–240)), Asp-74 to Val-240 (AIM II (aa 74–240)), Leu-83 to Val-240(AIM II (aa 83–240)), and Ala-101 to Val-240 (AIM II (aa 101–240)).

Even if deletion of one or more amino acids from the N-terminus of a protein results in modification or loss of one or more biological functions of the protein, other biological activities may still be retained. Thus, the ability of shortened AIM II muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that an AIM II mutein with a large number of deleted N-terminal amino acid residues may retain some biological or immunogenic activities. In fact, peptides composed of as few as six AIM II amino acid residues may often evoke an immune response.

Accordingly, the present invention further provides polypeptides having one or more residues deleted from the amino terminus of the AIM II amino acid sequence shown in FIGS. 1A and B (i.e., SEQ ID NO:2) up to the phenylalanine residue at position number 235, and polynucleotides encoding such polypeptides. In particular, the present invention provides polypeptides comprising the amino acid sequence of residues n-314 of FIGS. 1A and B (SEQ ID NO:2), where n is an integer in the range of 2 to 235, and 236 is the position of the first residue from the N-terminus of the complete AIM II polypeptide believed to be required for at least immunogenic activity of the AIM II polypeptide.

More in particular, the invention provides polynucleotides encoding polypeptides comprising, or alternatively consisting of, the amino acid sequence of residues of E-2 to V-240; E-3 to V-240; S-4 to V-240; V-5 to V-240; V-6 to V-240; R-7 to V-240; P-8 to V-240; S-9 to V-240; V-10 to V-240; F-11 to V-240; V-12 to V-240; V-13 to V-240; D-14 to V-240; G-15 to V-240; Q-16 to V-240; T-17 to V-240; D-18 to V-240; I-19 to V-240; P-20 to V-240; F-21 to V-240; T-22 to V-240; R-23 to V-240; L-24 to V-240; G-25 to V-240; R-26 to V-240; S-27 to V-240; H-28 to V-240; R-29 to V-240; R-30 to V-240; Q-31 to V-240; S-32 to V-240; C-33 to V-240; S-34 to V-240; V-35 to V-240; A-36 to V-240; R-37 to V-240; V-38 to V-240; G-39 to V-240; L-40 to V-240; G-41 to V-240; L-42 to V-240; L-43 to V-240; L-44 to V-240; L-45 to V-240; L-46 to V-240; M-47 to V-240; G-48 to V-240; A-49 to V-240; G-50 to V-240; L-51 to V-240; A-52 to V-240; V-53 to V-240; Q-54 to V-240; G-55 to V-240; W-56 to V-240; F-57 to V-240; L-58 to V-240; L-59 to V-240; Q-60 to V-240; L-61 to V-240; H-62 to V-240; W-63 to V-240; R-64 to V-240; L-65 to V-240; G-66 to V-240; E-67 to V-240; M-68 to V-240; V-69 to V-240; T-70 to V-240; R-71 to V-240; L-72 to V-240; P-73 to V-240; D-74 to V-240; G-75 to V-240; P-76 to V-240; A-77 to V-240; G-78 to V-240; S-79 to V-240; W-80 to V-240; E-81 to V-240; Q-82 to V-240; L-83 to V-240; I-84 to V-240; Q-85 to V-240; E-86 to V-240; R-87 to V-240; R-88 to V-240; S-89 to V-240; H-90 to V-240; E-91 to V-240; V-92 to V-240; N-93 to V-240; P-94 to V-240; A-95 to V-240; A-96 to V-240; H-97 to V-240; L-98 to V-240; T-99 to V-240; G-900 to V-240; A-9 to V-240; N-102 to V-240; S-103 to V-240; S-104 to V-240; L-105 to V-240; T-106 to V-240; G-107 to V-240; S-108 to V-240; G-109 to V-240; G-110 to V-240; P-111 to V-240; L-112 to V-240; L-113 to V-240; W-114 to V-240; E-115 to V-240; T-116 to V-240; Q-117 to V-240; L-118 to V-240; G-119 to V-240; L-120 to V-240; A-121 to V-240; F-122 to V-240; L-123 to V-240; R-124 to V-240; G-125 to V-240; L-126 to V-240; S-127 to V-240; Y-128 to V-240; H-129 to V-240; D-130 to V-240; G-131 to V-240; A-132 to V-240; L-133 to V-240; V-134 to V-240; V-135 to V-240; T-136 to V-240; K-137 to V-240; A-138 to V-240; G-139 to V-240; Y-140 to V-240; Y-141 to V-240; Y-142 to V-240; I-143 to V-240; Y-144 to V-240; S-145 to V-240; K-146 to V-240; V-147 to V-240; Q-148 to V-240; L-149 to V-240; G-150 to V-240; G-151 to V-240; V-152 to V-240; G-153 to V-240; C-154 to V-240; P-155 to V-240; L-156 to V-240; G-157 to V-240; L-158 to V-240; A-159 to V-240; S-160 to V-240; T-161 to V-240; I-162 to V-240; T-163 to V-240; H-164 to V-240; G-165 to V-240; L-166 to V-240; Y-167 to V-240; K-168 to V-240; R-169 to V-240; T-170 to V-240; P-171 to V-240; R-172 to V-240; Y-173 to V-240; P-174 to V-240; E-175 to V-240; E-176 to V-240; L-177 to V-240; E-178 to V-240; L-179 to V-240; L-180 to V-240; V-181 to V-240; S-182 to V-240; Q-183 to V-240; Q-184 to V-240; S-185 to V-240; P-186 to V-240; C-187 to V-240; G-188 to V-240; R-189 to V-240; A-190 to V-240; T-191 to V-240; S-192 to V-240; S-193 to V-240; S-194 to V-240; R-195 to V-240; V-196 to V-240; W-197 to V-240; W-198 to V-240; D-199 to V-240; S-200 to V-240; S-201 to V-240; F-202 to V-240; L-203 to V-240; G-204 to V-240; G-205 to V-240; V-206 to V-240; V-207 to V-240; H-208 to V-240; L-209 to V-240; E-210 to V-240; A-211 to V-240; G-212 to V-240; E-213 to V-240; E-214 to V-240; V-215 to V-240; V-216 to V-240; V-217 to V-240; R-218 to V-240; V-219 to V-240; L-220 to V-240; D-221 to V-240; E-222 to V-240; R-223 to V-240; L-224 to V-240; V-225 to V-240; R-226 to V-240; L-227 to V-240; R-228 to V-240; D-229 to V-240; G-230 to V-240; T-231 to V-240; R-232 to V-240; S-233 to V-240; Y-234 to V-240; and F-235 to V-240 of the AIM II sequence shown in SEQ ID NO:2 (which is identical to the sequence shown as FIG. 1A–B, with the exception that the amino acid residues in SEQ ID NO:2 are numbered consecutively from 1 through 240 from the N-terminus to the C-terminus). Polynucleotides encoding these polypeptides are also encompassed by the invention.

As mentioned above, even if deletion of one or more amino acids from the C-terminus of a protein results in modification or loss of one or more biological functions of the protein, other biological activities may still be retained. Thus, the ability of the shortened AIM II mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that an AIM II mutein with a large number of deleted C-terminal amino acid residues may retain some biological or immunogenic activities. In fact, peptides composed of as few as six AIM II amino acid residues may often evoke an immune response.

Accordingly, the present invention further provides polypeptides having one or more residues deleted from the carboxy terminus of the amino acid sequence of the AIM II polypeptide shown in FIGS. 1A and B (SEQ ID NO:2), up to the valine residue at position number 6, and polynucleotides encoding such polypeptides. In particular, the present invention provides polypeptides comprising the amino acid sequence of residues 1-m of FIGS. 1A and B (i.e., SEQ ID NO:2), where m is an integer in the range of 6 to 239, and 6 is the position of the first residue from the C-terminus of the complete AIM II polypeptide believed to be required for at least immunogenic activity of the AIM II polypeptide.

More in particular, the invention provides polynucleotides encoding polypeptides comprising, or alternatively consisting of, the amino acid sequence of residues M-1 to M-239; M-1 to F-238; M-1 to A-237; M-1 to G-236; M-1 to F-235; M-1 to Y-234; M-1 to S-233; M-1 to R-232; M-1 to T-231; M-1 to G-230; M-1 to D-229; M-1 to R-228; M-1 to L-227; M-1 to R-226; M-1 to V-225; M-1 to L-224; M-1 to R-223; M-1 to E-222; M-1 to D-221; M-1 to L-220; M-1 to V-219; M-1 to R-218; M-1 to V-217; M-1 to V-216; M-1 to V-215; M-1 to E-214; M-1 to E-213; M-1 to G-212; M-1 to A-211; M-1 to E-210; M-1 to L-209; M-1 to H-208; M-1 to V-207; M-1 to V-206; M-1 to G-205; M-1 to G-204; M-1 to L-203; M-1 to F-202; M-1 to S-201; M-1 to S-200; M-1 to D-199; M-1 to W-198; M-1 to W-197; M-1 to V-196; M-1 to R-195; M-1 to S-194; M-1 to S-193; M-1 to S-192; M-1 to T-191; M-1 to A-190; M-1 to R-189; M-1 to G-188; M-1 to C-187; M-1 to P-186; M-1 to S-185; M-1 to Q-184; M-1 to Q-183; M-1 to S-182; M-1 to V-181; M-1 to L-180; M-1 to L-179; M-1 to E-178; M-1 to L-177; M-1 to E-176; M-1 to E-175; M-1 to P-174; M-1 to Y-173; M-1 to R-172; M-1 to P-171; M-1 to T-170; M-1 to R-169; M-1 to K-168; M-1 to Y-167; M-1 to L-166; M-1 to G-165; M-1 to H-164; M-1 to T-163; M-1 to I-162; M-1 to T-161; M-1 to S-160; M-1 to A-159; M-1 to L-158; M-1 to G-157; M-1 to L-156; M-1 to P-155; M-1 to C-154; M-1 to G-153; M-1 to V-152; M-1 to G-151; M-1 to G-150; M-1 to L-149; M-1 to Q-148; M-1 to V-147; M-1 to K-146; M-1 to S-145; M-1 to Y-144; M-1 to I-143; M-1 to Y-142; M-1 to Y-141; M-1 to Y-140; M-1 to G-139; M-1 to A-138; M-1 to K-137; M-1 to T-136; M-1 to V-135; M-1 to V-134; M-1 to L-133; M-1 to A-132; M-1 to G-131; M-1 to D-130; M-1 to H-129; M-1 to Y-128; M-1 to S-127; M-1 to L-126; M-1 to G-125; M-1 to R-124; M-1 to L-123; M-1 to F-122; M-1 to A-121; M-1 to L-120; M-1 to G-119; M-1 to L-118; M-1 to Q-117; M-1 to T-116; M-1 to E-115; M-1 to W-114; M-1 to L-113; M-1 to L-112; M-1 to P-111; M-1 to G-110; M-1 to G-109; M-1 to S-108; M-1 to G-107; M-1 to T-106; M-1 to L-105; M-1 to S-104; M-1 to S-103; M-1 to N-102; M-1 to A-101; M-1 to G-100; M-1 to T-99; M-1 to L-98; M-1 to H-97; M-1 to A-96; M-1 to A-95; M-1 to P-94; M-1 to N-93; M-1 to V-92; M-1 to E-91; M-1 to H-90; M-1 to S-89; M-1 to R-88; M-1 to R-87; M-1 to E-86; M-1 to Q-85; M-1 to I-84; M-1 to L-83; M-1 to Q-82M-1 to E-81; M-1 to W-80; M-1 to S-79; M-1 to G-78; M-1 to A-77; M-1 to P-76; M-1 to G-75; M-1 to D-74; M-1 to P-73; M-1 to L-72; M-1 to R-71; M-1 to T-70; M-1 to V-69; M-1 to M-68; M-1 to E-67; M-1 to G-66; M-1 to L-65; M-1 to R-64; M-1 to W-63; M-1 to H-62; M-1 to L-61; M-1 to Q-60; M-1 to L-59; M-1 to L-58; M-1 to F-57; M-1 to W-56; M-1 to G-55; M-1 to Q-54; M-1 to V-53; M-1 to A-52; M-1 to L-51; M-1 to G-50; M-1 to A-49; M-1 to G-48; M-1 to M-47; M-1 to L-46; M-1 to L-45; M-1 to L-44; M-1 to L-43; M-1 to L-42; M-1 to G-41; M-1 to L-40; M-1 to G-39; M-1 to V-38; M-1 to R-37; M-1 to A-36; M-1 to V-35; M-1 to S-34; M-1 to C-33; M-1 to S-32; M-1 to Q-31; M-1 to R-30; M-1 to R-29; M-1 to H-28; M-1 to S-27; M-1 to R-26; M-1 to G-25; M-1 to L-24; M-1 to R-23; M-1 to T-22; M-1 to F-21; M-1 to P-20; M-1 to 1–19; M-1 to D-18; M-1 to T-17; M-1 to Q-16; M-1 to G-15; M-1 to D-14M-1 to V-13; M-1 to V-12; M-1 to F-i1; M-1 to V-10; M-1 to S-9; M-1 to P-8; M-1 to R-7; M-1 to V-6 of the sequence of the AIM II sequence shown in FIGS. 1A and B (which is identical to the sequence shown as SEQ ID NO:2, with the exception that the amino acid residues in SEQ ID NO:2 are numbered consecutively from 1 through 240 from the N-terminus to the C-terminus). Polynucleotides encoding these polypeptides also are provided.

The invention also provides polypeptides having one or more amino acids deleted from both the amino and the carboxyl termini of an AIM II polypeptide, which may be described generally as having residues n-m of FIGS. 1A and B (i.e., SEQ ID NO:2), where n and m are integers as described above.

The natural processed form of AIM II that was affinity purified on an LT-β receptor column from conditioned media of MCA-38 cells transformed with full length AIM II cDNA is Leu-83 to Val-240 in SEQ ID NO:2. (See Example 10). However, it appears that AIM II is processed differently in COS cells, producing an AIM II that is cleaved between Glu-67 and Met-68 to yield a polypeptide having amino acids 68–240 in SEQ ID NO:2. In addition, COS cells also cleave the AIM II between Met-68 and Val-69, resulting a polypeptide having amino acids 69–240 in SEQ ID NO:2.

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host. For example, a recombinantly produced version of the AIM II polypeptide can be substantially purified by the one-step method described in Smith and Johnson, *Gene* 67:31–40 (1988).

The polypeptides of the present invention include the polypeptide encoded by the deposited cDNA, the polypeptide of FIGS. 1A and B (SEQ ID NO:2), the polypeptide of FIGS. 1A and B (SEQ ID NO:2) lacking the N-terminal methionine, the extracellular domain, the transmembrane domain, the intracellular domain, soluble polypeptides comprising all or part of the extracellular and intracellular domains but lacking the transmembrane domain, as well as polypeptides which are at least 80% identical, more preferably at least 90% or 95% identical, still more preferably at least 96%, 97%, 98% or 99% identical to the polypeptide encoded by the deposited cDNA, to the polypeptide of FIGS. 1A and B (SEQ ID NO:2), and also include portions of such polypeptides with at least 30 amino acids and more preferably at least 50 amino acids.

By a polypeptide having an amino acid sequence at least, for example, 95% "identical" to a reference amino acid sequence of an AIM II polypeptide is intended that the amino acid sequence of the polypeptide is identical to the reference sequence except that the polypeptide sequence may include up to five amino acid alterations per each 100 amino acids of the reference amino acid of the AIM II polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIGS. 1A and B (SEQ ID NO:2) or to the amino acid sequence encoded by deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequences shown in Table 1 or to the amino acid sequence encoded by deposited DNA clone can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* 6:237–245(1990)). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues of the query (reference) sequence that extend past the N- or C-termini of the subject sequence are considered for the purposes of manually adjusting the percent identity score. That is, only residues which are not matched/aligned with the N- or C-termini of the query sequence are counted when manually adjusting the percent identity score.

For example, a 90 amino acid residue subject sequence is aligned with a 100 residue query sequence to determine percent identity. The deletion occurs at the N-terminus of the subject sequence and therefore, the FASTDB alignment does not show a match/alignment of the first 10 residues at the N-terminus. The 10 unpaired residues represent 10% of the sequence (number of residues at the N-and C- termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

As used herein the term "AIM II" polypeptide includes membrane-bound proteins (comprising a cytoplasmic domain, a transmembrane domain, and an extracellular domain) as well as truncated proteins that retain the AIM II polypeptide activity. In one embodiment, soluble AIM II polypeptides comprise all or part of the extracellular domain of an AIM II protein, but lack the transmembrane region that would cause retention of the polypeptide on a cell membrane. Soluble AIM II may also include part of the transmembrane region or part of the cytoplasmic domain or other sequences, provided that the soluble AIM II protein is capable of being secreted. A heterologous signal peptide can be fused to the N-terminus of the soluble AIM II polypeptide such that the soluble AIM II polypeptide is secreted upon expression.

The polypeptide of the present invention could be used as a molecular weight marker on SDS-PAGE gels or on molecular sieve gel filtration columns using methods well known to those of skill in the art.

In another aspect, the invention provides peptides and polypeptides comprising epitope-bearing portions of the polypeptides of the present invention. These epitopes are immunogenic or antigenic epitopes of the polypeptides of the present invention. An "immunogenic epitope" is defined as a part of a protein that elicits an antibody response in vivo when the whole polypeptide of the present invention, or fragment thereof, is the immunogen. On the other hand, a region of a polypeptide to which an antibody can bind is defined as an "antigenic determinant" or "antigenic epitope." The number of in vivo immunogenic epitopes of a protein generally is less than the number of antigenic epitopes. See, e.g., Geysen, et al., *Proc. Natl. Acad. Sci. USA* 81:3998–4002(1983). However, antibodies can be made to any antigenic epitope, regardless of whether it is an immunogenic epitope, by using methods such as phage display. See, e.g., Petersen G. et al., *Mol. Gen. Genet.* 249:425–431 (1995). Therefore, included in the present invention are both immunogenic epitopes and antigenic epitopes.

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. Science 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al. Cell 37:767–778(1984) at 777.

Antigenic epitope-bearing peptides and polypeptides of the invention preferably contain a sequence of at least seven, more preferably at least nine and most preferably between about at least about 15 to about 30 amino acids contained within the amino acid sequence of a polypeptide of the invention.

Non-limiting examples of antigenic polypeptides or peptides that can be used to generate AIM II-specific antibodies include: a polypeptide comprising amino acid residues from about 13 to about 20 in FIGS. 1A and B (SEQ ID NO:2); a polypeptide comprising amino acid residues from about 23 to about 36 in FIG. 1 (SEQ ID NO:2); a polypeptide comprising amino acid residues from about 69 to about 79 in FIGS. 1A and B (SEQ ID NO:2); a polypeptide comprising amino acid residues from about 85 to about 94 in FIGS. 1A and B (SEQ ID NO:2); a polypeptide comprising amino acid residues from about 167 to about 178 in FIGS. 1A and B (SEQ ID NO:2); a polypeptide comprising amino acid residues from about 184 to about 196 in FIGS. 1A and B (SEQ ID NO:2); and a polypeptide comprising amino acid residues from about 221 to about 233 in FIGS. 1A and B (SEQ ID NO:2). As indicated above, the inventors have determined that the above polypeptide fragments are antigenic regions of the AIM II protein.

The AIM II polypeptides of the invention may be in monomers or multimers (i.e., dimers, trimers, tetramers and higher multimers). Accordingly, the present invention relates to monomers and multimers of the AIM II polypeptides of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only AIM II polypeptides of the invention (including AIM II fragments, variants, splice variants, and fusion proteins, as described herein). These homomers may contain AIM II polypeptides having identical or different amino acid sequences. In a specific embodiment, a homomer of the invention is a multimer containing only AIM II polypeptides having an identical amino acid sequence. In another specific embodiment, a homomer of the invention is a multimer containing AIM II polypeptides having different amino acid sequences. In specific embodiments, the multimer of the invention is a homodimer (e.g., containing AIM II polypeptides having identical or different amino acid sequences) or a homotrimer (e.g., containing AIM II polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the AIM II and AIM II polypeptides of the invention. In a specific embodiment, the multimer of the invention is a heterodimer, a heterotrimer, or a heterotetramer. In additional embodiments, the homomeric multimer of the invention is at least a homodimer, at least a homotrimer, or at least a homotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the AIM II polypeptides of the invention. Such covalent associations may involve one or more amino acid residues contained in the polypeptide sequence (e.g., that recited in SEQ ID NO:2 or SEQ ID NO:39, or contained in the polypeptide encoded by the clones designated as ATCC Accession 97689 and 97483). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in an AIM II fusion protein. In one example, covalent associations are between the heterologous sequence contained in a fusion protein of the invention (see, e.g., U.S. Pat. No. 5,478,925). In a specific example, the covalent associations are between the heterologous sequence contained in an AIM II-Fc fusion protein of the invention (as described herein). In another specific example, covalent associations of fusion proteins of the invention are between heterologous polypeptide sequence from another TNF family ligand/receptor member that is capable of forming covalently associated multimers, such as for example, oseteoprotegerin (see, e.g., International Publication No. WO 98/49305, the contents of which are herein incorporated by reference in its entirety).

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporatedby reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hyrophobic or signal peptide) and which can be incorporated by membrane reconstitution techniques into liposomes (see, e.g., U.S. Pat. No. 5,478,925, which is herein incorporated by reference in its entirety).

The invention encompasses AIM II polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of AIM II which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028–1035(1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

The epitope-bearing peptides and polypeptides of the invention may be produced by any conventional means. Houghten, R. A. (1985) General method for the rapid solid-phase synthesis of large numbers of peptides: specificity of antigen-antibody interaction at the level of individual amino acids. *Proc. Natl. Acad. Sci. USA* 82:5131–5135. This "Simultaneous Multiple Peptide Synthesis (SMPS)" process is further described in U.S. Pat. No. 4,631,211 to Houghten et al. (1986).

The present invention further relates to antibodies and T-cell antigen receptors (TCR) which specifically bind the polypeptides of the present invention. The antibodies of the present invention include IgG (including IgG1, IgG2, IgG3, and IgG4), IgA (including IgA1 and IgA2), IgD, IgE, IgM, and IgY. As used herein, the term "antibody" (Ab) is meant to include whole antibodies, including single-chain whole antibodies, and antigen-binding fragments thereof. Most preferably the antibodies are human antigen binding antibody fragments of the present invention that include, but are not limited to, Fab, Fab' and F(ab')2, Fd, single-chain Fvs (scFv), single-chain antibodies, disulfide-linked Fvs (sdFv) and fragments comprising either a VL or VH domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, CH1, CH2, and CH3 domains. Also included in the invention are any combinations of variable region(s) and hinge region, CH1, CH2, and CH3 domains. The present invention further includes chimeric, humanized, and human monoclonal and polyclonal antibodies which specifically bind the polypeptides of the present invention. The present invention further includes antibodies which are anti-idiotypic to the antibodies of the present invention.

The antibodies of the present invention may be monospecific, bispecific, trispecific or of greater multi specificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, A. et al., *J. Immunol.* 147:60–69(1991); U.S. Pat. Nos. 5,573,920, 4,474,893, 5,601,819, 4,714,681, 4,925,648; Kostelny, S. A. et al., *J. Immunol.* 148:1547–1553(1992).

Antibodies of the present invention may be described or specified in terms of the epitope(s) or portion(s) of a polypeptide of the present invention which are recognized or specifically bound by the antibody. The epitope(s) or polypeptide portion(s) may be specified as described herein, e.g., by N-terminal and C-terminal positions, by size in contiguous amino acid residues, or as listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies which only bind polypeptides encoded by polynucleotides which hybridize to a polynucleotide of the present invention under stringent hybridization conditions (as described herein). Antibodies of the present invention may also be described or specified in terms of their binding affinity. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples. See, e.g., Harlow et al., *ANTIBODIES: A LABORATORY MANUAL*, (Cold Spring Harbor Laboratory Press, 2nd ed. 1988) (incorporated by reference in the entirety).

The antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

The antibodies of the present invention may be prepared by any suitable method known in the art. For example, a polypeptide of the present invention or an antigenic fragment thereof can be administered to an animal in order to induce the production of sera containing polyclonal antibodies. Monoclonal antibodies can be prepared using a wide of techniques known in the art including the use of hybridoma and recombinant technology. See, e.g., Harlow et al., *ANTIBODIES: A LABORATORY MANUAL*, (Cold Spring Harbor Laboratory Press, 2nd ed. 1988); Hammerling, et al., in: *MONOCLONAL ANTIBODIES AND T-CELL HYBRIDOMAS* 563–681(Elsevier, N.Y., 1981) (said references incorporated by reference in their entireties).

Fab and F(ab')2 fragments may be produced by proteolytic cleavage, using enzymes such as papain (to produce Fab fragments) or pepsin (to produce F(ab')2 fragments).

Alternatively, antibodies of the present invention can be produced through the application of recombinant DNA technology or through synthetic chemistry using methods known in the art. For example, the antibodies of the present invention can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman U. et al., *J. Immunol. Methods* 182:41–50(1995); Ames, R. S. et al., *J. Immunol. Methods* 184:177–186 (1995); Kettleborough, C. A. et al., *Eur. J. Immunol.* 24:952–958(1994); Persic, L. et al., *Gene* 187:9–18(1997); Burton, D. R. et al., *Advances in Immunology* 57:191–280 (1994); PCT/GB91/01134; WO 90/02809; WO 91/10737;

WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743 (said references incorporated by reference in their entireties).

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')2 fragments can also be employed using methods known in the art such as those disclosed in WO 92/22324; Mullinax, R. L. et al., *BioTechniques* 12:864–869(1992); and Sawai, H. et al., AJRI 34:26–34(1995); and Better, M. et al., *Science* 240:1041–1043(1988) (said references incorporated by reference in their entireties).

Examples of techniques which can be used to produce single-chain Fvs and antibodies include those described in U.S. Pat. Nos. 4,946,778 and 5,258,498; Huston et al. (1991) *Methods in Enzymology* 203:46–88; Shu, L. et al. (1993) *PNAS* 90:7995–7999; and Skerra, A. et al., *Science* 240:1038–1040(1988). For some uses, including in vivo use of antibodies in humans and in vitro detection assays, it may be preferable to use chimeric, humanized, or human antibodies. Methods for producing chimeric antibodies are known in the art. See e.g., Morrison, *Science* 229:1202 (1985); Oi et al., *BioTechniques* 4:214(1986); Gillies, S. D. et al. (1989) *J. Immunol. Methods* 125:191–202; and U.S. Pat. No. 5,807,715. Antibodies can be humanized using a variety of techniques including CDR-grafting (EP 0 239 400; WO 91/09967; U.S. Pat. Nos. 5,530,101; and 5,585, 089), veneering or resurfacing (EP 0 592 106; EP 0 519 596; Padlan E. A., (1991) Molecular Immunology 28(4/5): 489–498; Studnicka G. M. et al. (1994) *Protein Engineering* 7(6):805–814; Roguska M. A. et al. (1994) *PNAS* 91:969–973), and chain shuffling (U.S. Pat. No. 5,565,332). Human antibodies can be made by a variety of methods known in the art including phage display methods described above. See also, U.S. Pat. Nos. 4,444,887, 4,716,111, 5,545, 806, and 5,814,318; and WO 98/46645(said references incorporated by reference in their entireties).

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al. supra and WO 93/21232; EP 0 439 095; Naramura, M. et al., *Immunol. Lett.* 39:91–99(1994); U.S. Pat. No. 5,474, 981; Gillies, S. O. et al. (1992) *PNAS* 89:1428–1432; Fell, H. P. et al. (1991) *J. Immunol.* 146:2446–2452(said references incorporated by reference in their entireties).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi, A. et al. (1991) *PNAS* 88:10535–10539; Zheng, X. X. et al. (1995) *J. Immunol.* 154:5590–5600; and Vil, H. et al. (1992) *PNAS* 89:11337–11341(said references incorporated by reference in their entireties).

The invention further relates to antibodies which act as agonists or antagonists of the polypeptides of the present invention. For example, the present invention includes antibodies which disrupt the receptor/ligand interactions with the polypeptides of the invention either partially or fully. Included are both receptor-specific antibodies and ligand-specific antibodies. Included are receptor-specific antibodies which do not prevent ligand binding but prevent receptor activation. Receptor activation (i.e., signaling) may be determined by techniques described herein or otherwise known in the art. Also include are receptor-specific antibodies which both prevent ligand binding and receptor activation. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies which activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng, B. et al. (1998) Blood 92(6):1981–1988; Chen, Z. et al. (1998) Cancer Res. 58(16): 3668–3678; Harrop, J. A. et al. (1998) J. Immunol. 161(4): 1786–1794; Zhu, Z. et al. (1998) Cancer Res. 58(15): 3209–3214; Yoon, D. Y. et al. (1998) J. Immunol. 160(7): 3170–3179; Prat, M. et al. (1998) J. Cell. Sci. 111 (Pt2): 237–247; Pitard, V. et al. (1997) J. Immunol. Methods 205(2):177–190; Liautard, J. et al. (1997) Cytokinde 9(4): 233–241; Carlson, N. G. et al. (1997) J. Biol. Chem. 272(17):11295–11301; Taryman, R. E. et al. (1995) Neuron 14(4):755–762; Muller, Y. A. et al. (1998) Structure 6(9): 1153–1167; Bartunek, P. et al. (1996) Cytokine 8(1):14–20 (said references incorporated by reference in their entireties).

In additional embodiments, the polynucleotides of the invention encode functional attributes of AIM II. Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of AIM II.

The data representing the structural or functional attributes of AIM II set forth in FIGS. 3A–F and/or Table 2 was generated using the various modules and algorithms of the DNA*STAR set on default parameters. In a preferred embodiment, the data presented in columns VIII, IX, XIII, and XIV of Table 2 can be used to determine regions of AIM II which exhibit a high degree of potential for antigenicity. Regions of high antigenicity are determined from the data presented in columns VIII, IX, XIII, and/or IV by choosing values which represent regions of the polypeptide which are likely to be exposed on the surface of the polypeptide in an environment in which antigen recognition may occur in the process of initiation of an immune response.

Certain preferred regions in these regards are set out in FIGS. 3A–F, but may, as shown in Table 2, be represented or identified by using tabular representations of the data presented in FIGS. 3A–F. The DNA*STAR computer algorithm used to generate FIGS. 3A–F (set on the original default parameters) was used to present the data in FIGS. 3A–F in a tabular format (See Table 2). The tabular format of the data in FIG. 3A–F may be used to easily determine specific boundaries of a preferred region.

The above-mentioned preferred regions set out in FIGS. 3A–F and in Table 2 include, but are not limited to, regions of the aforementioned types identified by analysis of the amino acid sequence set out in FIGS. 1A and B. As set out in FIGS. 3A–F and in Table 2, such preferred regions include Garnier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index.

TABLE 2

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | A | — | — | — | — | — | — | 0.19 | −0.71 | — | — | — | 0.95 | 1.49 |
| Glu | 2 | A | — | — | — | — | — | — | −0.28 | −0.50 | * | — | — | 0.50 | 0.87 |
| Glu | 3 | A | — | — | B | — | — | — | 0.22 | −0.29 | * | — | — | 0.30 | 0.50 |
| Ser | 4 | A | — | — | B | — | — | — | 0.40 | −0.71 | * | — | — | 0.60 | 0.99 |
| Val | 5 | A | — | — | B | — | — | — | 0.49 | −0.90 | * | * | — | 0.60 | 0.89 |
| Val | 6 | A | — | — | B | — | — | — | 0.23 | −0.51 | — | — | — | 0.60 | 0.69 |
| Arg | 7 | — | — | B | — | — | T | — | −0.47 | 0.13 | * | * | — | 0.10 | 0.38 |
| Pro | 8 | — | — | B | — | — | T | — | −1.32 | 0.53 | * | * | — | −0.20 | 0.44 |
| Ser | 9 | — | — | B | — | — | T | — | −1.88 | 0.53 | * | — | — | −0.20 | 0.44 |
| Val | 10 | — | — | B | — | — | T | — | −1.02 | 0.53 | * | * | — | −0.20 | 0.17 |
| Phe | 11 | — | — | B | — | — | — | — | −0.51 | 0.53 | — | * | — | −0.40 | 0.18 |
| Val | 12 | — | — | B | — | — | — | — | −0.62 | 0.53 | — | * | — | −0.12 | 0.13 |
| Val | 13 | — | — | B | — | — | T | — | −0.72 | 0.54 | — | * | — | 0.36 | 0.31 |
| Asp | 14 | — | — | B | — | — | T | — | −0.42 | 0.39 | — | * | F | 1.09 | 0.52 |
| Gly | 15 | — | — | — | — | T | T | — | −0.46 | −0.40 | — | * | F | 2.52 | 1.17 |
| Gln | 16 | — | — | — | — | T | T | — | 0.03 | −0.36 | — | * | F | 2.80 | 1.11 |
| Thr | 17 | — | — | — | B | — | — | C | 0.19 | −0.57 | — | * | F | 2.22 | 1.03 |
| Asp | 18 | — | — | B | B | — | — | — | 0.73 | 0.21 | — | * | F | 0.69 | 0.90 |
| Ile | 19 | — | — | B | B | — | — | — | 0.84 | 0.27 | — | * | F | 0.41 | 0.75 |
| Pro | 20 | — | — | B | B | — | — | — | 0.38 | −0.13 | * | * | — | 0.73 | 1.02 |
| Phe | 21 | — | — | B | B | — | — | — | 0.03 | 0.07 | * | — | — | −0.30 | 0.50 |
| Thr | 22 | — | — | B | B | — | — | — | 0.46 | 0.50 | * | — | — | −0.26 | 0.71 |
| Arg | 23 | — | — | B | B | — | — | — | 0.16 | −0.19 | * | — | F | 1.13 | 0.90 |
| Leu | 24 | — | — | — | B | T | — | — | 1.01 | −0.23 | * | — | F | 2.02 | 1.39 |
| Gly | 25 | — | — | — | B | T | — | — | 1.33 | −0.51 | * | — | F | 2.66 | 1.31 |
| Arg | 26 | — | — | — | — | T | T | — | 2.14 | −1.00 | * | — | F | 3.40 | 1.31 |
| Ser | 27 | — | — | — | — | T | T | — | 2.46 | −1.00 | * | — | F | 3.06 | 3.11 |
| His | 28 | — | — | — | — | T | T | — | 2.04 | −1.29 | * | — | F | 3.03 | 5.44 |
| Arg | 29 | — | — | — | — | T | T | — | 2.19 | −1.33 | * | — | F | 3.00 | 3.72 |
| Arg | 30 | — | — | — | — | T | — | — | 2.23 | −0.76 | * | * | F | 2.77 | 1.49 |
| Gln | 31 | — | — | — | — | T | T | — | 1.27 | −0.76 | * | — | F | 2.94 | 1.47 |
| Ser | 32 | — | — | — | — | T | T | — | 0.98 | −0.61 | * | — | F | 3.10 | 0.56 |
| Cys | 33 | — | — | B | — | — | T | — | 1.12 | −0.11 | * | — | — | 1.94 | 0.29 |
| Ser | 34 | — | — | B | — | — | T | — | 0.16 | −0.11 | * | — | — | 1.63 | 0.32 |
| Val | 35 | — | — | B | B | — | — | — | −0.30 | 0.13 | * | * | — | 0.32 | 0.18 |
| Ala | 36 | — | — | B | B | — | — | — | −1.11 | 0.17 | — | * | — | 0.01 | 0.33 |
| Arg | 37 | — | — | B | B | — | — | — | −1.16 | 0.29 | * | * | — | −0.30 | 0.20 |
| Val | 38 | — | — | B | B | — | — | — | −1.30 | 0.33 | * | * | — | −0.30 | 0.27 |
| Gly | 39 | — | — | B | B | — | — | — | −1.11 | 0.37 | * | * | — | −0.30 | 0.22 |
| Leu | 40 | — | A | B | — | — | — | — | −1.77 | 0.56 | * | * | — | −0.60 | 0.09 |
| Gly | 41 | — | A | B | — | — | — | — | −1.99 | 1.24 | * | * | — | −0.60 | 0.10 |
| Leu | 42 | — | A | B | — | — | — | — | −2.91 | 1.29 | * | * | — | −0.60 | 0.09 |
| Leu | 43 | — | A | B | — | — | — | — | −2.66 | 1.54 | — | — | — | −0.60 | 0.09 |
| Leu | 44 | — | A | B | — | — | — | — | −2.66 | 1.47 | — | — | — | −0.60 | 0.09 |
| Leu | 45 | — | A | B | — | — | — | — | −2.43 | 1.47 | — | — | — | −0.60 | 0.10 |
| Leu | 46 | — | A | B | — | — | — | — | −2.43 | 1.29 | — | — | — | −0.60 | 0.13 |
| Met | 47 | A | A | — | — | — | — | — | −2.43 | 1.03 | — | — | — | −0.60 | 0.15 |
| Gly | 48 | A | — | — | — | — | T | — | −2.21 | 1.03 | — | — | — | −0.20 | 0.15 |
| Ala | 49 | A | — | — | — | — | T | — | −2.26 | 0.84 | — | — | — | −0.20 | 0.19 |
| Gly | 50 | A | — | — | — | — | T | — | −1.44 | 0.80 | — | — | — | −0.20 | 0.14 |
| Leu | 51 | A | — | — | — | — | T | — | −0.98 | 0.59 | — | — | — | −0.20 | 0.25 |
| Ala | 52 | — | A | B | — | — | — | — | −0.67 | 0.59 | — | * | — | −0.60 | 0.24 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Val | 53 | A | A | — | — | — | — | — | −1.02 | 1.00 | — | — | — | −0.60 | 0.26 |
| Gln | 54 | — | A | B | — | — | — | — | −1.24 | 1.36 | — | * | — | −0.60 | 0.27 |
| Gly | 55 | — | A | B | — | — | — | — | −1.71 | 1.36 | — | * | — | −0.60 | 0.22 |
| Trp | 56 | A | A | — | — | — | — | — | −0.90 | 1.54 | — | * | — | 0.60 | 0.24 |
| Phe | 57 | — | A | B | — | — | — | — | −1.12 | 1.30 | — | * | — | −0.60 | 0.24 |
| Leu | 58 | — | A | B | — | — | — | — | −0.30 | 1.59 | — | * | — | −0.60 | 0.20 |
| Leu | 59 | — | A | B | — | — | — | — | −0.59 | 1.66 | * | * | — | −0.60 | 0.26 |
| Gln | 60 | — | A | B | — | — | — | — | −0.13 | 1.66 | * | * | — | −0.60 | 0.32 |
| Leu | 61 | — | A | — | — | — | — | C | −0.66 | 0.87 | * | * | — | −0.40 | 0.76 |
| His | 62 | — | A | — | — | — | — | C | −0.30 | 0.87 | * | * | — | −0.40 | 0.76 |
| Trp | 63 | — | A | — | — | — | — | C | 0.51 | 0.61 | * | * | — | −0.40 | 0.43 |
| Arg | 64 | A | A | — | — | — | — | — | 0.72 | 0.21 | * | * | — | −0.30 | 0.91 |
| Leu | 65 | A | A | — | — | — | — | — | −0.13 | 0.14 | * | * | — | −0.30 | 0.66 |
| Gly | 66 | — | A | — | — | T | — | — | 0.37 | 0.29 | * | * | — | 0.10 | 0.47 |
| Glu | 67 | — | A | B | — | — | — | — | 0.51 | −0.14 | * | * | — | 0.30 | 0.34 |
| Met | 68 | — | A | B | — | — | — | — | −0.01 | −0.14 | * | * | — | 0.30 | 0.82 |
| Val | 69 | — | A | B | — | — | — | — | −0.33 | −0.14 | * | — | — | 0.64 | 0.68 |
| Thr | 70 | — | A | B | — | — | — | — | 0.48 | −0.14 | * | — | — | 0.98 | 0.61 |
| Arg | 71 | — | A | B | — | — | — | — | 0.48 | −0.14 | * | * | F | 1.62 | 1.02 |
| Leu | 72 | — | — | B | — | — | T | — | 0.27 | −0.33 | * | — | F | 2.36 | 1.37 |
| Pro | 73 | — | — | — | — | T | T | — | 0.28 | −0.54 | * | — | F | 3.40 | 1.46 |
| Asp | 74 | — | — | — | — | T | T | — | 0.79 | −0.53 | * | — | F | 2.91 | 0.75 |
| Gly | 75 | — | — | — | — | — | T | C | 0.80 | −0.10 | * | — | F | 2.07 | 0.91 |
| Pro | 76 | — | — | — | — | — | T | C | 0.40 | −0.40 | * | — | F | 1.73 | 0.78 |
| Ala | 77 | — | — | — | — | — | T | C | 1.21 | 0.09 | — | — | F | 0.79 | 0.49 |
| Gly | 78 | — | — | — | — | — | T | C | 1.42 | 0.09 | — | — | F | 0.45 | 0.86 |
| Ser | 79 | — | — | — | — | — | T | C | 0.61 | 0.06 | * | — | F | 0.45 | 0.97 |
| Trp | 80 | A | A | — | — | — | — | — | 0.07 | 0.31 | * | — | F | −0.15 | 0.79 |
| Glu | 81 | A | A | — | — | — | — | — | 0.28 | 0.50 | * | — | — | −0.60 | 0.56 |
| Gln | 82 | A | A | — | — | — | — | — | 0.87 | 0.47 | — | * | — | −0.60 | 0.72 |
| Leu | 83 | A | A | — | — | — | — | — | 1.32 | 0.09 | — | — | — | −0.15 | 1.19 |
| Ile | 84 | A | A | — | — | — | — | — | 1.73 | −0.83 | — | — | — | 0.75 | 1.35 |
| Gln | 85 | A | A | — | — | — | — | — | 1.72 | −0.83 | — | — | F | 0.90 | 1.52 |
| Glu | 86 | A | A | — | — | — | — | — | 1.69 | −0.84 | — | — | F | 0.90 | 2.48 |
| Arg | 87 | A | A | — | — | — | — | — | 1.69 | −1.03 | — | — | F | 0.90 | 4.81 |
| Arg | 88 | — | A | — | — | T | — | — | 1.64 | −1.71 | — | — | F | 1.30 | 4.81 |
| Ser | 89 | — | A | — | — | T | — | — | 2.53 | −1.47 | — | — | F | 1.30 | 2.06 |
| His | 90 | — | A | — | — | — | — | C | 2.32 | −1.07 | — | — | — | 0.95 | 1.69 |
| Glu | 91 | — | A | — | — | — | — | C | 1.73 | −0.64 | * | — | — | 0.95 | 1.34 |
| Val | 92 | — | A | — | — | — | — | C | 1.03 | −0.14 | * | — | — | 0.65 | 1.01 |
| Asn | 93 | — | — | — | — | — | T | C | 0.89 | −0.03 | — | * | — | 0.90 | 0.75 |
| Pro | 94 | A | — | — | — | — | T | — | 0.38 | −0.03 | — | * | — | 0.70 | 0.59 |
| Ala | 95 | A | — | — | — | — | T | — | 0.10 | 0.66 | — | * | — | −0.20 | 0.65 |
| Ala | 96 | A | — | — | — | — | T | — | −0.24 | 0.50 | — | * | — | −0.20 | 0.59 |
| His | 97 | A | — | — | — | — | — | — | 0.02 | 0.53 | — | * | — | −0.40 | 0.37 |
| Leu | 98 | A | — | — | — | — | — | — | 0.02 | 0.60 | — | — | — | −0.40 | 0.37 |
| Thr | 99 | — | — | B | — | — | — | — | −0.07 | 0.50 | — | — | — | −0.40 | 0.60 |
| Gly | 100 | — | — | — | — | — | — | C | 0.22 | 0.39 | — | — | F | 0.25 | 0.59 |
| Ala | 101 | — | — | — | — | — | — | C | 0.00 | 0.27 | — | — | F | 0.25 | 0.96 |
| Asn | 102 | — | — | B | — | — | T | — | −0.28 | 0.27 | — | — | F | 0.25 | 0.55 |
| Ser | 103 | — | — | B | — | — | T | — | 0.19 | 0.27 | — | — | F | 0.25 | 0.80 |
| Ser | 104 | — | — | B | — | — | T | — | 0.20 | 0.27 | — | * | F | 0.25 | 0.78 |
| Leu | 105 | — | — | B | — | — | T | — | 0.20 | 0.16 | — | — | F | 0.25 | 0.65 |
| Thr | 106 | — | — | B | — | — | — | — | 0.44 | 0.19 | — | * | F | 0.05 | 0.48 |
| Gly | 107 | — | — | — | — | T | T | — | 0.23 | 0.23 | — | — | F | 0.65 | 0.35 |
| Ser | 108 | — | — | — | — | T | T | — | −0.28 | 0.27 | — | — | F | 0.65 | 0.66 |
| Gly | 109 | — | — | — | — | T | — | C | −0.79 | 0.27 | — | — | F | 0.45 | 0.38 |
| Gly | 110 | — | — | — | — | T | — | C | −0.27 | 0.47 | — | — | F | 0.15 | 0.32 |
| Pro | 111 | — | A | — | — | — | — | C | 0.04 | 0.96 | — | — | F | −0.25 | 0.25 |
| Leu | 112 | — | A | — | — | — | — | C | 0.08 | 0.57 | — | — | F | −0.25 | 0.43 |
| Leu | 113 | — | A | B | — | — | — | — | 0.38 | 0.63 | — | * | F | −0.60 | 0.63 |
| Trp | 114 | — | A | B | — | — | — | — | −0.09 | 0.60 | — | — | — | −0.60 | 0.71 |
| Glu | 115 | — | A | B | — | — | — | — | −0.09 | 0.86 | — | * | — | −0.60 | 0.71 |
| Thr | 116 | A | A | — | — | — | — | — | −0.69 | 0.60 | — | * | F | −0.45 | 0.85 |
| Gln | 117 | A | A | — | — | — | — | — | −0.47 | 0.60 | — | * | F | −0.45 | 0.67 |
| Leu | 118 | A | A | — | — | — | — | — | −0.36 | 0.19 | — | — | — | −0.30 | 0.39 |
| Gly | 119 | A | A | — | — | — | — | — | −0.88 | 0.97 | * | * | — | −0.60 | 0.23 |
| Leu | 120 | A | A | — | — | — | — | — | −0.77 | 1.17 | * | * | — | −0.60 | 0.11 |
| Ala | 121 | — | A | B | — | — | — | — | −0.80 | 0.77 | * | — | — | −0.60 | 0.26 |
| Phe | 122 | — | A | B | — | — | — | — | −1.61 | 0.51 | * | — | — | −0.60 | 0.26 |
| Leu | 123 | — | A | B | — | — | — | — | −1.10 | 0.77 | * | — | — | −0.60 | 0.26 |
| Arg | 124 | — | A | B | — | — | — | — | −1.00 | 0.51 | * | — | — | −0.60 | 0.35 |
| Gly | 125 | — | A | B | — | — | — | — | −0.22 | 0.73 | — | — | — | −0.60 | 0.63 |
| Leu | 126 | — | — | B | — | — | — | — | 0.37 | 0.44 | * | — | — | −0.25 | 1.05 |
| Ser | 127 | — | — | — | — | — | — | C | 0.72 | −0.24 | * | — | — | 0.70 | 0.89 |
| Tyr | 128 | — | — | — | — | — | — | C | 0.94 | 0.19 | * | * | — | 0.10 | 0.89 |
| His | 129 | — | — | — | — | T | T | — | 0.02 | 0.26 | * | — | — | 0.65 | 1.09 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Asp | 130 | — | — | — | — | T | T | — | −0.49 | 0.26 | — | — | — | 0.50 | 0.67 |
| Gly | 131 | — | — | B | — | — | T | — | −0.53 | 0.51 | — | — | — | −0.20 | 0.32 |
| Ala | 132 | — | — | B | — | — | T | — | −0.54 | 0.40 | * | — | — | −0.20 | 0.17 |
| Leu | 133 | — | — | B | B | — | — | — | −0.26 | 0.39 | * | — | — | −0.30 | 0.15 |
| Val | 134 | — | — | B | B | — | — | — | −0.81 | 0.39 | * | — | — | −0.30 | 0.30 |
| Val | 135 | — | — | B | B | — | — | — | −1.16 | 0.46 | * | — | — | −0.60 | 0.30 |
| Thr | 136 | — | — | B | B | — | — | — | −1.06 | 0.39 | — | — | — | −0.30 | 0.36 |
| Lys | 137 | — | — | B | — | — | T | — | −0.71 | 0.46 | — | — | F | −0.05 | 0.77 |
| Ala | 138 | — | — | B | — | — | T | — | −0.14 | 0.57 | — | — | — | −0.05 | 1.62 |
| Gly | 139 | — | — | B | — | — | T | — | −0.18 | 0.69 | — | — | — | −0.05 | 1.76 |
| Tyr | 140 | — | — | B | — | — | T | — | 0.43 | 0.89 | * | — | — | −0.20 | 0.62 |
| Tyr | 141 | — | — | B | B | — | — | — | 0.44 | 1.64 | — | — | — | −0.60 | 0.96 |
| Tyr | 142 | — | — | B | B | — | — | — | 0.44 | 1.53 | — | * | — | −0.45 | 1.30 |
| Ile | 143 | — | — | B | B | — | — | — | 0.18 | 1.10 | — | * | — | −0.45 | 1.66 |
| Tyr | 144 | — | — | B | B | — | — | — | 0.52 | 0.99 | — | * | — | −0.60 | 0.78 |
| Ser | 145 | — | — | B | B | — | — | — | −0.04 | 0.63 | — | * | — | −0.60 | 0.87 |
| Lys | 146 | — | — | B | B | — | — | — | −0.14 | 0.56 | — | * | — | −0.45 | 1.02 |
| Val | 147 | — | — | B | B | — | — | — | −0.24 | 0.30 | — | * | — | −0.30 | 0.64 |
| Gln | 148 | — | — | B | B | — | — | — | −0.21 | −0.03 | — | * | — | 0.30 | 0.48 |
| Leu | 149 | — | — | B | B | — | — | — | −0.31 | 0.23 | — | * | — | −0.30 | 0.18 |
| Gly | 150 | — | — | B | B | — | — | — | −0.68 | 0.66 | — | * | — | −0.60 | 0.24 |
| Gly | 151 | — | — | B | B | — | — | — | −0.93 | 0.59 | — | * | — | −0.60 | 0.07 |
| Val | 152 | — | — | B | B | — | — | — | −0.89 | 0.61 | — | — | — | −0.60 | 0.14 |
| Gly | 153 | — | — | B | — | — | — | — | −1.23 | 0.61 | — | — | — | −0.40 | 0.11 |
| Cys | 154 | — | — | B | — | — | T | — | −1.23 | 0.61 | — | — | — | −0.20 | 0.11 |
| Pro | 155 | — | — | B | — | — | T | — | −1.48 | 0.87 | — | — | — | −0.20 | 0.13 |
| Leu | 156 | — | — | B | — | — | T | — | −1.43 | 0.73 | — | — | — | −0.20 | 0.13 |
| Gly | 157 | — | — | B | — | — | T | — | −0.89 | 0.69 | — | — | — | −0.20 | 0.32 |
| Leu | 158 | — | — | B | B | — | — | — | −1.43 | 0.60 | — | — | — | −0.60 | 0.32 |
| Ala | 159 | — | — | B | B | — | — | — | −1.08 | 0.86 | — | — | — | −0.60 | 0.26 |
| Ser | 160 | — | — | B | B | — | — | — | −0.90 | 0.66 | — | — | — | −0.60 | 0.37 |
| Thr | 161 | — | — | B | B | — | — | — | −0.43 | 0.73 | * | — | F | −0.45 | 0.62 |
| Ile | 162 | — | — | B | B | — | — | — | −0.90 | 0.47 | * | — | — | −0.60 | 0.60 |
| Thr | 163 | — | — | B | B | — | — | — | −0.33 | 0.66 | * | — | — | −0.60 | 0.37 |
| His | 164 | — | — | B | B | — | — | — | 0.30 | 1.03 | * | — | — | −0.60 | 0.40 |
| Gly | 165 | — | — | B | B | — | — | — | 0.71 | 0.54 | — | — | — | −0.45 | 1.15 |
| Leu | 166 | — | — | B | B | — | — | — | 0.71 | −0.14 | — | — | — | 0.75 | 1.56 |
| Tyr | 167 | — | — | — | B | T | — | — | 1.39 | −0.14 | * | — | — | 1.45 | 1.66 |
| Lys | 168 | — | — | — | B | T | — | — | 1.81 | −0.21 | * | — | F | 1.90 | 2.59 |
| Arg | 169 | — | — | B | — | — | — | — | 1.60 | −0.64 | * | — | F | 2.30 | 6.15 |
| Thr | 170 | — | — | — | — | — | T | C | 1.73 | −0.57 | * | — | F | 3.00 | 6.15 |
| Pro | 171 | — | — | — | — | — | T | C | 2.54 | −0.90 | * | — | F | 2.70 | 4.75 |
| Arg | 172 | — | — | — | — | — | T | C | 2.79 | −0.90 | * | — | F | 2.40 | 4.20 |
| Tyr | 173 | — | — | — | — | — | T | C | 1.93 | −0.90 | * | * | F | 2.10 | 5.05 |
| Pro | 174 | — | A | — | — | — | — | C | 1.82 | −0.70 | * | * | F | 1.40 | 2.69 |
| Glu | 175 | A | A | — | — | — | — | — | 1.32 | −1.13 | * | * | F | 0.90 | 2.38 |
| Glu | 176 | A | A | — | — | — | — | — | 0.72 | −0.44 | * | * | F | 0.60 | 1.25 |
| Leu | 177 | A | A | — | — | — | — | — | −0.24 | −0.51 | * | * | — | 0.60 | 0.67 |
| Glu | 178 | A | A | — | — | — | — | — | −0.30 | −0.30 | * | — | — | 0.30 | 0.29 |
| Leu | 179 | A | A | — | — | — | — | — | −0.09 | 0.09 | — | — | — | −0.30 | 0.22 |
| Leu | 180 | A | A | — | — | — | — | — | −0.09 | 0.49 | — | — | — | −0.60 | 0.47 |
| Val | 181 | A | A | — | — | — | — | — | −0.39 | 0.20 | — | * | — | −0.30 | 0.47 |
| Ser | 182 | A | A | — | — | — | — | — | 0.21 | 0.59 | — | — | F | −0.45 | 0.76 |
| Gln | 183 | — | — | — | — | T | — | — | −0.46 | 0.33 | — | — | F | 0.60 | 1.42 |
| Gln | 184 | — | — | B | — | — | — | — | 0.01 | 0.21 | — | * | F | 0.20 | 1.02 |
| Ser | 185 | — | — | — | — | — | T | C | 0.93 | 0.00 | * | * | F | 0.45 | 0.76 |
| Pro | 186 | — | — | — | — | T | T | — | 1.20 | −0.39 | — | * | F | 1.25 | 0.85 |
| Cys | 187 | — | — | — | — | T | T | — | 1.19 | −0.29 | — | * | F | 1.25 | 0.50 |
| Gly | 188 | — | — | B | — | — | T | — | 0.89 | −0.20 | — | * | F | 1.15 | 0.54 |
| Arg | 189 | — | — | B | B | — | — | — | 0.59 | −0.20 | — | * | F | 1.05 | 0.47 |
| Ala | 190 | — | — | B | B | — | — | — | 0.59 | −0.24 | * | * | F | 1.50 | 1.16 |
| Thr | 191 | — | — | — | B | — | — | C | 0.91 | −0.43 | — | * | F | 2.00 | 1.58 |
| Ser | 192 | — | — | — | — | — | T | C | 0.72 | −0.86 | — | * | F | 3.00 | 1.58 |
| Ser | 193 | — | — | B | — | — | T | — | 0.78 | −0.21 | — | * | F | 2.20 | 1.16 |
| Ser | 194 | — | — | B | — | — | T | — | 0.38 | 0.20 | * | * | F | 1.15 | 0.84 |
| Arg | 195 | — | — | B | — | — | T | — | 0.97 | 0.63 | * | * | F | 0.55 | 0.66 |
| Val | 196 | — | — | B | B | — | — | — | 0.98 | 0.24 | * | * | — | 0.00 | 0.82 |
| Trp | 197 | — | — | — | B | T | — | — | 0.98 | 0.24 | — | * | — | 0.10 | 0.82 |
| Trp | 198 | — | — | B | B | — | — | — | 0.58 | 0.24 | — | * | — | −0.30 | 0.56 |
| Asp | 199 | — | — | B | — | — | T | — | 0.07 | 1.03 | — | * | F | −0.05 | 0.66 |
| Ser | 200 | — | — | — | — | — | T | C | −0.39 | 1.07 | — | * | — | 0.15 | 0.52 |
| Ser | 201 | — | — | — | — | — | T | C | 0.12 | 0.59 | — | — | F | 0.15 | 0.49 |
| Phe | 202 | — | — | — | — | T | T | — | −0.44 | 0.10 | — | — | F | 0.65 | 0.29 |
| Leu | 203 | — | — | — | B | — | — | C | −1.01 | 0.74 | — | — | — | −0.40 | 0.16 |
| Gly | 204 | — | — | — | B | — | — | C | −1.04 | 1.00 | — | — | — | −0.40 | 0.09 |
| Gly | 205 | — | — | — | B | — | — | C | −1.56 | 1.11 | — | — | — | −0.40 | 0.14 |
| Val | 206 | — | A | B | — | — | — | — | −1.26 | 1.01 | — | * | — | 0.60 | 0.14 |

TABLE 2-continued

| Res | Position | I | II | III | IV | V | VI | VII | VIII | IX | X | XI | XII | XIII | XIV |
|-----|----------|---|----|----|----|---|----|----|------|----|---|----|----|------|-----|
| Val | 207 | — | A | B | — | — | — | — | −1.14 | 0.33 | — | — | — | −0.30 | 0.24 |
| His | 208 | A | A | — | — | — | — | — | −0.68 | 0.40 | — | — | — | −0.60 | 0.25 |
| Leu | 209 | A | A | — | — | — | — | — | −0.33 | 0.40 | — | — | — | −0.60 | 0.33 |
| Glu | 210 | A | A | — | — | — | — | — | 0.01 | −0.24 | — | * | — | 0.30 | 0.77 |
| Ala | 211 | A | A | — | — | — | — | — | 0.01 | −0.89 | — | — | F | 0.75 | 0.98 |
| Gly | 212 | A | A | — | — | — | — | — | 0.01 | −0.74 | — | * | F | 0.75 | 0.88 |
| Glu | 213 | A | A | — | B | — | — | — | −0.81 | −0.79 | * | * | F | 0.75 | 0.38 |
| Glu | 214 | A | A | — | B | — | — | — | 0.11 | −0.14 | * | * | F | 0.45 | 0.28 |
| Val | 215 | A | A | — | B | — | — | — | −0.74 | −0.64 | * | * | — | 0.60 | 0.55 |
| Val | 216 | A | A | — | B | — | — | — | −0.97 | −0.43 | * | * | — | 0.30 | 0.24 |
| Val | 217 | A | A | — | B | — | — | — | −0.62 | 0.26 | * | * | — | −0.30 | 0.11 |
| Arg | 218 | A | A | — | B | — | — | — | −0.62 | 0.26 | * | * | — | −0.30 | 0.25 |
| Val | 219 | A | A | — | B | — | — | — | −0.51 | −0.39 | * | * | — | 0.30 | 0.59 |
| Leu | 220 | A | A | — | B | — | — | — | −0.47 | −1.03 | * | — | — | 0.75 | 1.56 |
| Asp | 221 | A | A | — | B | — | — | — | −0.47 | −0.99 | * | — | F | 0.75 | 0.66 |
| Glu | 222 | A | A | — | — | — | — | — | 0.50 | −0.34 | * | — | F | 0.45 | 0.66 |
| Arg | 223 | A | A | — | — | — | — | — | −0.42 | −0.99 | * | * | — | 0.90 | 1.56 |
| Leu | 224 | A | A | — | — | — | — | — | 0.54 | −0.99 | * | * | — | 0.60 | 0.77 |
| Val | 225 | — | A | B | — | — | — | — | 1.36 | −0.99 | * | * | — | 0.94 | 0.87 |
| Arg | 226 | — | A | B | — | — | — | — | 1.01 | −0.99 | — | * | — | 1.28 | 0.74 |
| Leu | 227 | — | — | B | — | — | T | — | 0.70 | −0.56 | * | * | — | 2.02 | 0.89 |
| Arg | 228 | — | — | B | — | — | T | — | 0.70 | −0.76 | — | * | F | 2.66 | 1.73 |
| Asp | 229 | — | — | — | — | T | T | — | 1.21 | −1.40 | * | * | F | 3.40 | 1.78 |
| Gly | 230 | — | — | — | — | T | T | — | 1.82 | −1.01 | * | * | F | 3.06 | 2.81 |
| Thr | 231 | — | — | — | — | T | — | — | 1.01 | −0.94 | * | * | F | 2.52 | 2.25 |
| Arg | 232 | — | — | B | — | — | — | — | 1.48 | −0.16 | * | * | F | 1.48 | 1.17 |
| Ser | 233 | — | — | B | — | — | T | — | 0.78 | 0.27 | * | * | F | 0.74 | 1.17 |
| Tyr | 234 | — | — | B | — | — | T | — | 0.08 | 0.34 | * | — | — | 0.10 | 0.82 |
| Phe | 235 | — | — | B | — | — | T | — | −0.18 | 0.64 | — | — | — | −0.20 | 0.36 |
| Gly | 236 | — | — | B | — | — | T | — | −0.72 | 1.26 | — | — | — | −0.20 | 0.27 |
| Ala | 237 | — | A | B | — | — | — | — | −1.22 | 1.51 | — | — | — | −0.60 | 0.13 |
| Phe | 238 | — | A | B | — | — | — | — | −1.31 | 1.19 | — | — | — | −0.60 | 0.19 |
| Met | 239 | — | A | B | — | — | — | — | −1.46 | 0.83 | — | — | — | −0.60 | 0.24 |
| Val | 240 | — | A | B | — | — | — | — | −1.14 | 0.83 | — | — | — | −0.60 | 0.30 |

Among highly preferred fragments in this regard are those that comprise regions of AIM II that combine several structural features, such as several of the features set out above in Table 2.

The AIM II polypeptide of the present invention may be employed to treat lymphoproliferative disease which results in lymphadenopathy, the AIM II mediates apoptosis by stimulating clonal deletion of T-cells and may therefore, be employed to treat autoimmune disease, to stimulate peripheral tolerance and cytotoxic T-cell mediated apoptosis. The AIM II may also be employed as a research tool in elucidating the biology of autoimmune disorders including systemic lupus erythematosus (SLE), Graves' disease, immunoproliferative disease lymphadenopathy (IPL), angioimmunoproliferative lymphadenopathy (AIL), immunoblastive lymphadenopathy (IBL), rheumatoid arthritis, diabetes, and multiple sclerosis, allergies and to treat graft versus host disease.

The AIM II polypeptide of the present invention may also be employed to inhibit neoplasia, such as tumor cell growth. The AIM II polypeptide may be responsible for tumor destruction through apoptosis and cytotoxicity to certain cells. AIM II may also be employed to treat diseases which require growth promotion activity, for example, restenosis, since AIM II has proliferation effects on cells of endothelial origin. AIM II may, therefore, also be employed to regulate hematopoiesis in endothelial cell development.

This invention also provides a method for identification of molecules, such as receptor molecules, that bind AIM II. Genes encoding proteins that bind AIM II, such as receptor proteins, can be identified by numerous methods known to those of skill in the art, for example, ligand panning and FACS sorting. Such methods are described in many laboratory manuals such as, for instance, Coligan et al., *Current Protocols in Immunology*, 1(2): Chapter 5(1991).

For instance, expression cloning may be employed for this purpose. To this end polyadenyiated RNA is prepared from a cell responsive to AIM II, a cDNA library is created from this RNA, the library is divided into pools and the pools are transfected individually into cells that are not responsive to AIM II. The transfected cells then are exposed to labeled AIM II. (AIM II can be labeled by a variety of well-known techniques including standard methods of radio-iodination or inclusion of a recognition site for a site-specific protein kinase.) Following exposure, the cells are fixed and binding of AIM II is determined. These procedures conveniently are carried out on glass slides.

Pools are identified of cDNA that produced AIM II-binding cells. Sub-pools are prepared from these positives, transfected into host cells and screened as described above. Using an iterative sub-pooling and re-screening process, one or more single clones that encode the putative binding molecule, such as a receptor molecule, can be isolated.

Alternatively a labeled ligand can be photo affinity linked to a cell extract, such as a membrane or a membrane extract, prepared from cells that express a molecule that it binds, such as a receptor molecule. Cross-linked material is resolved by polyacrylamide gel electrophoresis ("PAGE") and exposed to X-ray film. The labeled complex containing the ligand-receptor can be excised, resolved into peptide fragments, and subjected to protein microsequencing. The amino acid sequence obtained from microsequencing can be used to design unique or degenerate oligonucleotide probes to screen cDNA libraries to identify genes encoding the putative receptor molecule.

Polypeptides of the invention also can be used to assess AIM II binding capacity of AIM II binding molecules, such as receptor molecules, in cells or in cell-free preparations.

A list of exemplified amino acid sequences comprising immunogenic epitopes are shown in Table 2. It is pointed out that Table 2 only lists amino acid residues comprising epitopes predicted to have the highest degree of antigenicity using the algorithm of Jameson and Wolf, *Comp. Appl. Biosci.* 4:181–186(1988) (said references incorporated by reference in their entireties). The Jameson-Wolf antigenic analysis was performed using the computer program PROTEAN, using default parameters (Version 3.11 for the Power MacIntosh, DNASTAR, Inc., 1228 South Park Street Madison, Wis.). Table 2 and portions of polypeptides not listed in Table 2 are not considered non-immunogenic. The immunogenic epitopes of Table 2 is an exemplified list, not an exhaustive list, because other immunogenic epitopes are merely not recognized as such by the particular algorithm used. Amino acid residues comprising other immunogenic epitopes may be routinely determined using algorithms similar to the Jameson-Wolf analysis or by in vivo testing for an antigenic response using methods known in the art. See, e.g., Geysen et al., supra; U.S. Pat. Nos. 4,708,781; 5,194,392; 4,433,092; and 5,480,971 (said references incorporated by reference in their entireties).

It is particularly pointed out that the amino acid sequences of Table 2 comprise immunogenic epitopes. Table 2 lists only the critical residues of immunogenic epitopes determined by the Jameson-Wolf analysis. Thus, additional flanking residues on either the N-terminal, C-terminal, or both N- and C-terminal ends may be added to the sequences of Table 2 to generate an epitope-bearing polypeptide of the present invention. Therefore, the immunogenic epitopes of Table 2 may include additional N-terminal or C-terminal amino acid residues. The additional flanking amino acid residues may be contiguous flanking N-terminal and/or C-terminal sequences from the polypeptides of the present invention, heterologous polypeptide sequences, or may include both contiguous flanking sequences from the polypeptides of the present invention and heterologous polypeptide sequences.

Polypeptides of the present invention comprising immunogenic or antigenic epitopes are at least 7 amino acids residues in length. "At least" means that a polypeptide of the present invention comprising an immunogenic or antigenic epitope may be 7 amino acid residues in length or any integer between 7 amino acids and the number of amino acid residues of the full length polypeptides of the invention. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. However, it is pointed out that each and every integer between 7 and the number of amino acid residues of the full length polypeptide are included in the present invention.

The immunogenic and antigenic epitope-bearing fragments may be specified by either the number of contiguous amino acid residues, as described above, or further specified by N-terminal and C-terminal positions of these fragments on the amino acid sequence of SEQ ID NO:2. Every combination of a N-terminal and C-terminal position that a fragment of, for example, at least 7 or at ;east 15 contiguous amino acid residues in length could occupy on the amino acid sequence of SEQ ID NO:2 is included in the invention. Again, "at least 7 contiguous amino acid residues in length" means 7 amino acid residues in length or any integer between 7 amino acids and the number of amino acid residues of the full length polypeptide of the present invention. Specifically, each and every integer between 7 and the number of amino acid residues of the full length polypeptide are included in the present invention.

Immunogenic and antigenic epitope-bearing polypeptides of the invention are useful, for example, to make antibodies which specifically bind the polypeptides of the invention, and in immunoassays to detect the polypeptides of the present invention. The antibodies are useful, for example, in affinity purification of the polypeptides of the present invention. The antibodies may also routinely be used in a variety of qualitative or quantitative immunoassays, specifically for the polypeptides of the present invention using methods known in the art. See, e.g., Harlow et al., Antibodies: A Laboratory Manual, (Cold Spring Harbor Laboratory Press; 2nd Ed. 1988).

The epitope-bearing polypeptides of the present invention may be produced by any conventional means for making polypeptides including synthetic and recombinant methods known in the art. For instance, epitope-bearing peptides may be synthesized using known methods of chemical synthesis. For instance, Houghten has described a simple method for the synthesis of large numbers of peptides, such as 10–20 mgs of 248 individual and distinct 13 residue peptides representing single amino acid variants of a segment of the HA1 polypeptide, all of which were prepared and characterized (by ELISA-type binding studies) in less than four weeks (Houghten et al., *Proc. Natl. Acad. Sci. USA* 82:5131–5135(1985)). This "Simultaneous Multiple Peptide Synthesis (SMPS)" process is further described in U.S. Pat. No. 4,631,211 to Houghten and coworkers (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously (Houghten et al., *Proc. Natl. Acad. Sci. USA* 82:5131–5135(1985) at 5134).

Epitope-bearing polypeptides of the present invention are used to induce antibodies according to methods well known in the art including, but not limited to, in vivo immunization, in vitro immunization, and phage display methods. See, e.g., Sutcliffe et al., supra; Wilson et al., supra, and Bittle et al. *J. Gen. Virol.* 66:2347–2354(1985). If in vivo immunizationis used, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine residues may be coupled to a carrier using a linker such as -maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 $\mu$g of peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and discussed above, the polypeptides of the present invention comprising an immunogenic or antigenic epitope can be fused to heterologous polypeptide sequences. For example, the polypeptides of the present invention may be fused with the constant domain of immunoglobulins (IgA, IgE, IgG, IgM), or portions thereof (CH1, CH2, CH3, any combination thereof including both entire domains and portions thereof) resulting in chimeric polypeptides. These fusion proteins facilitate purification, and show an increased half-life in vivo. This has been shown, e.g., for chimeric proteins consisting of the first two domains of the human CD4-polypeptide and various domains of the constant regions of the heavy or light chains of mammalian immunoglobulins. See, e.g., EPA0, 394,827; Traunecker et al., *Nature* 331:84–86(1988). Fusion proteins that have a disulfide-linked dimeric structure due to the IgG portion can also be more efficient in binding and neutralizing other molecules than monomeric polypeptides or fragments thereof alone. See, e.g., Fountoulakis et al., *J. Biochem*. 270:3958–3964(1995). Nucleic acids encoding the above epitopes can also be recombined with a gene of interest as an epitope tag to aid in detection and purification of the expressed polypeptide.

The present inventors have discovered that AIM II is expressed in spleen, thymus and bone marrow tissue. For a number of disorders, such as septic shock, inflammation, cerebral malaria, activation of the HIV virus, graft-host rejection, bone resorption, rheumatoid arthritis and cachexia, it is believed that significantly higher or lower levels of AIM II gene expression can be detected in certain tissues (e.g., spleen, thymus and bone marrow tissue) or bodily fluids (e.g., serum, plasma, urine, synovial fluid or spinal fluid) taken from an individual having such a disorder, relative to a "standard" AIM II gene expression level, i.e., the AIM II expression level in tissue or bodily fluids from an individual not having the disorder. Thus, the invention provides a diagnostic method useful during diagnosis of a disorder, which involves: (a) assaying AIM II gene expression level in cells or body fluid of an individual; (b) comparing the AIM II gene expression level with a standard AIM II gene expression level, whereby an increase or decrease in the assayed AIM II gene expression level compared to the standard expression level is indicative of a disorder.

Cell Sorting

The present invention also relates to methods for separating cells into subpopulations based on whether these cells bind either the AIM II polypeptides of the invention or antibodies having specificity for these polypeptides. These separation methods will generally be based on the principle that cells which either express a surface receptor which binds AIM II polypeptides or have an AIM II polypeptide on their surface can be identified using labeled AIM II polypeptides or AIM II specific antibodies. Such cells can then be separated from other cells in a population which do not bind these polypeptides or antibodies. Methods for separating cells, commonly known as "cell sorting", are known in the art and are discussed in Crane, U.S. Pat. No. 5,489,506.

Thus, in one aspect, the invention provides methods for separating cells which bind either AIM II polypeptides or antibodies having specificity for AIM II polypeptides comprising contacting a population of cells with either an AIM II polypeptide or an antibody having specificity for the AIM II polypeptide, wherein the AIM II polypeptide or antibody is labelled with a detectable label and separating cells which bind either the AIM II polypeptide or anti-AIM II polypeptide antibody from cells which do not bind these molecules. Cells which bind AIM II polypeptides are believed to include those which express the lymphotoxin-β-receptor (LT-β-R), TR2, CD27, and TRANK.

AIM II Agonists and Antagonists

The invention also provides a method of screening compounds to identify those which enhance or block the action of AIM II on cells, such as its interaction with AIM II-binding molecules such as receptor molecules. An agonist is a compound which increases the natural biological functions of AIM II or which functions in a manner similar to AIM II, while antagonists decrease or eliminate such functions.

For example, a cellular compartment, such as a membrane preparation, may be prepared from a cell that expresses a molecule that binds AIM II, such as a molecule of a signaling or regulatory pathway modulated by AIM II. The preparation is incubated with labeled AIM II in the absence or the presence of a candidate molecule which may be an AIM II agonist or antagonist. The ability of the candidate molecule to bind the binding molecule or AIM II itself is reflected in decreased binding of the labeled ligand. Molecules which bind gratuitously, i.e., without inducing the effects of AIM II when bound to the AIM II binding molecule, are most likely to be good antagonists. Molecules that bind well and elicit effects that are the same as or closely related to AIM II, are good agonists.

AIM II-like effects of potential agonists and antagonists may by measured, for instance, by determining activity of a second messenger system following interaction of the candidate molecule with a cell or appropriate cell preparation, and comparing the effect with that of AIM II or molecules that elicit the same effects as AIM II. Second messenger systems that may be useful in this regard include but are not limited to AMP guanylate cyclase, ion channel or phosphoinositide hydrolysis second messenger systems.

Another example of an assay for AIM II antagonists is a competitive assay that combines AIM II and a potential antagonist with membrane-bound AIM II receptor molecules or recombinant AIM II receptor molecules under appropriate conditions for a competitive inhibition assay. AIM II can be labeled, such as by radioactivity, such that the number of AIM II molecules bound to a receptor molecule can be determined accurately to assess the effectiveness of the potential antagonist.

Potential antagonists include small organic molecules, peptides, polypeptides and antibodies that bind to a polypeptide of the invention, and thereby inhibit or extinguish its activity. Potential antagonists also may be small organic molecules, a peptide, a polypeptide such as a closely related protein or antibody that binds the same sites on a binding molecule, such as a receptor molecule, without inducing AIM II-induced activities, thereby preventing the action of AIM II by excluding AIM II from binding. Antagonists of the invention include fragments of the AIM II polypeptide having the amino acid sequence shown in SEQ ID NO:2.

Other potential antagonists include antisense molecules. Antisense technology can be used to control gene expression through antisense DNA or RNA or through triple-helix formation. Antisense techniques are discussed, for example, in Okano, *J. Neurochem*. 56:560(1991); Oligodeoxynucleotides as Antisense Inhibitors of Gene Expression, CRC Press, Boca Raton, Fla. (1988). Triple helix formation is discussed in, for instance, Lee et al., *Nucleic Acids Research* 6:3073(1979); Cooney et al., *Science* 241:456(1988); and Dervan et al., *Science* 251:1360(1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of AIM II. The antisense RNA oligonucleotide hybridizes to the mRNA in vivo and blocks translation of the mRNA molecule into AIM II polypeptide. The oligonucleotides described above can also be delivered to cells such that the antisense RNA or DNA may be expressed in vivo to inhibit production of AIM II.

The antagonists may be employed in a composition with a pharmaceutically acceptable carrier, e.g., as hereinafter described.

The antagonists may be employed for instance to treat cachexia which is a lipid clearing defect resulting from a systemic deficiency of lipoprotein lipase, which is believed to be suppressed by AIM II. The AIM II antagonists may also be employed to treat cerebral malaria in which AIM II may play a pathogenic role.

The AIM II antagonists may also be employed to prevent graft-host rejection by preventing the stimulation of the immune system in the presence of a graft.

The AIM II antagonists may also be employed to inhibit bone resorption and, therefore, to treat and/or prevent osteoporosis.

The antagonists may also be employed as anti-inflammatory agents, and to treat endotoxic shock. This critical condition results from an exaggerated response to bacterial and other types of infection.

As noted above, antagonists and agonists of the invention include AIM II polypeptides. These polypeptides can modulate their effect by, for example, binding to cellular proteins such as receptors. Methods for identifying peptides which interact with a specific protein are know in the art. For example, Phizicky and Fields, "Protein-protein interactions: methods for detection and analysis" *Microbiol. Rev.* 59:94–123(1995), describe methods for screening peptides to identify those having binding affinity for a second polypeptide. Phizicky and Fields discuss methods such as protein affinity chromatography, affinity blotting, coimmunoprecipitation, and cross-linking. Additional molecular biological methods suitable for use with the present invention include protein probing of expression libraries, the two-hybrid system, cell panning, and phage display.

Another method for identifying AIM II polypeptides of the invention which bind to a cell surface receptor involves transfecting eukaryotic cells with DNA encoding the receptor, such that the cells expresses the receptor on their surfaces, followed by contacting the cells with a labeled (e.g., radioactive label, biotin, etc.) AIM II polypeptide. The amount of labeled AIM II polypeptide bound to the cells is measured and compared to that bound to control cells. The control cells will generally be cells which do not express the surface receptor. The detection of an increased amount of label bound to the cells which express the receptor as compared to the control cells indicates that the cells which expresses the receptor bind the AIM II polypeptide.

Further, as one skilled in the art would recognize, cells which express and retain AIM II polypeptides can be used to identify AIM II ligands. In one such an embodiment, cells which express AIM II would be contacted with potential ligands which have been detectably labeled. Further, such ligands may be polypeptides which are expressed as part of a library of sequences on the surface of a phage (e.g., a phage display library).

Once an AIM II polypeptide has been identified which binds to the cell surface receptor of interest, assays can be performed to determine whether the AIM II polypeptide induces or inhibits a receptor-mediated cellular response normally elicited by the particular receptor. Whether an AIM II polypeptide activates a receptor-mediated cellular response may be determined by measuring a cellular response known to be elicited by the receptor in the presence of the AIM II polypeptide or another ligand. Further, whether an AIM II polypeptide inhibits a receptor-mediated cellular response may be determined by measuring a cellular response known to be elicited by the receptor in the presence of both a molecule which is known to induce the cellular response and the AIM II polypeptide.

Soluble forms of the polypeptides of the present invention (e.g., an AIM polypeptide comprising amino acid 83–240 of SEQ ID NO:2), for example, may be utilized in the ligand binding and receptor activation/inhibition assay described above.

Cancer Prognosis

It is believed that certain tissues in mammals with cancer express significantly reduced levels of the AIM II protein and mRNA encoding the AIM II protein when compared to a corresponding "standard" mammal, i.e., a mammal of the same species not having the cancer. Further, it is believed that reduced levels of the AIM II protein can be detected in certain body fluids (e.g., sera, plasma, urine, and spinal fluid) from mammals with cancer when compared to sera from mammals of the same species not having the cancer. Thus, the invention provides a diagnostic method useful during tumor diagnosis, which involves assaying the expression level of the gene encoding the AIM II protein in mammalian cells or body fluid and comparing the gene expression level with a standard AIM II gene expression level, whereby an decrease in the gene expression level over the standard is indicative of certain tumors.

Where a tumor diagnosis has already been made according to conventional methods, the present invention is useful as a prognostic indicator, whereby patients exhibiting enhanced AIM II gene expression may experience a better clinical outcome relative to patients expressing the gene at a lower level.

By "assaying the expression level of the gene encoding the AIM II protein" is intended qualitatively or quantitatively measuring or estimating the level of the AIM II protein or the level of the mRNA encoding the AIM II protein in a first biological sample either directly (e.g., by determining or estimating absolute protein level or mRNA level) or relatively (e.g., by comparing to the AIM II protein level or mRNA level in a second biological sample).

Preferably, the AIM II protein level or mRNA level in the first biological sample is measured or estimated and compared to a standard AIM II protein level or mRNA level, the standard being taken from a second biological sample obtained from an individual not having the cancer. As will be appreciated in the art, once a standard AIM II protein level or mRNA level is known, it can be used repeatedly as a standard for comparison.

By "biological sample" is intended any biological sample obtained from an individual, cell line, tissue culture, or other source which contains AIM II protein or mRNA. Biological samples include mammalian body fluids (such as sera, plasma, urine, synovial fluid and spinal fluid) which contain secreted mature AIM II protein, and ovarian, prostate, heart, placenta, pancreas liver, spleen, lung, breast and umbilical tissue.

The present invention is useful for detecting cancer in mammals. In particular the invention is useful during diagnosis of the of following types of cancers in mammals: breast, ovarian, prostate, bone, liver, lung, pancreatic, and spleenic. Preferred mammals include monkeys, apes, cats, dogs, cows, pigs, horses, rabbits and humans. Particularly preferred are humans.

Total cellular RNA can be isolated from a biological sample using the single-step guanidinium-thiocyanate-phenol-chloroform method described in Chomczynski and Sacchi, Anal. Biochem. 162:156–159(1987). Levels of mRNA encoding the AIM II protein are then assayed using any appropriate method. These include Northern blot analysis (Harada et al., Cell 63:303–312(1990)), S1 nuclease mapping (Fujita et al., Cell 49:357–367(1987)), the polymerase chain reaction (PCR), reverse transcription in combination with the polymerase chain reaction (RT-PCR) (Makino et al., Technique 2:295–301(1990)), and reverse transcription in combination with the ligase chain reaction (RT-LCR).

Assaying AIM II protein levels in a biological sample can occur using antibody-based techniques. For example, AIM II protein expression in tissues can be studied with classical immunohistological methods (Jalkanen, M., et al., J. Cell. Biol. 101:976–985(1985); Jalkanen, M., et al., J. Cell. Biol. 105:3087–3096(1987)).

Other antibody-based methods useful for detecting AIM II protein gene expression include immunoassays, such as the enzyme linked immunosorbent assay (ELISA) and the radio-immunoassay (RIA).

Suitable labels are known in the art and include enzyme labels, such as, Glucose oxidase, and radioisotopes, such as iodine ($^{125}I$, $^{112}I$), carbon ($^{14}C$), sulfur ($^{35}S$), tritium ($^3H$), indium ($^{112}In$), and technetium ($^{99m}Tc$), and fluorescent labels, such as fluorescein and rhodamine, and biotin.

Therapeutics

The uses of the AIM II polypeptides, particularly human AIM II polypeptides, include but are not limited to the treatment viral hepatitis, Herpes viral infections, allergic reactions, adult respiratory distress syndrome, neoplasia, anaphylaxis, allergic asthma, allergen rhinitis, drug allergies (e.g., to penicillin, cephalosporins), primary central nervous system lymphoma (PCNSL), chronic lymphocytic leukemia (CLL), lymphadenopathy, autoimmune disease, graft versus host disease, rheumatoid arthritis, osteoarthritis, Graves' disease, acute lymphoblastic leukemia (ALL), non-Hodgkin's lymphoma (NHL), ophthalmopathy, uveoretinitis, the autoimmune phase of Type 1 diabetes, myasthenia gravis, glomerulonephritis, autoimmune hepatological disorder, autoimmune inflammatory bowel disease, and Crohn's disease. In addition, the AIM II polypeptide of the present invention may be employed to inhibit neoplasia, such as tumor cell growth. The combination of AIM II protein with immunotherapeutic agent such as IL-2 or IL-12 may result in synergistic or additive effects that would be useful for the treatment of established cancers. The AIM II polypeptide may also be useful for tumor therapy. AIM II may further be employed to treat diseases which require growth promotion activity, for example, restenosis, since AIM II has proliferative effects on cells of endothelial origin. AIM II may, therefore, also be employed to regulate hematopoiesis in endothelial cell development.

The AIM II polypeptides of the invention may also be employed to inhibit the differentiation and proliferation of T cells and B cells. AIM II induced inhibition of T and B cell activation, differentiation and/or proliferation may be employed to treat a number of immunological based diseases, several of which are referred to above. Further, depending on the particular AIM II polypeptide employed, the AIM II polypeptides of the invention may also be employed to stimulate activation, differentiation and/or proliferation of T cells and B cells.

AIM II may act as a cytokine adjuvant or costimulatory molecule. The following experiments are performed to assess the in vivo AIM II protein on the host immune system.

Tumor or non-tumor bearing mice are treated with AIM II protein at three different doses (0.1 mg/kg, 1 mg/kg and 10 mg/kg, i.p., QD, 10–14 days, N=5 per group) before or after immunization with tumor antigen or superantigen, the mice are sacrificed weekly post treatment after blood collection. The spleens or the lymph nodes are used for the following in vitro analyses well known to those skilled in the art:

FACS analyses:
    Expression of surface markers for T cells, B cells, NK cells, Monocytes, Dendritic cells, costimulatory and adhesion molecules.
Cytokine production assays
T cell proliferation or cytotoxicity assay AIM II protein and tumor antigen may result in the induction of protective immunity, which could lead to protecting mice from subsequent tumor challenge. In order to examine possibility the following experiment can be performed using syngeneic C57BL/6 mice to test the effect of AIM II on induction of tumor or Ag-specific protective immunity.

MC-38 tumor-free mice treated with AIM II protein will be challenged with MC-38 or irrelevant murine sarcoma MCA-102 using techniques well known to those skilled in the art. Three possible results could be observed:

|  | Result #1 | Result #2 | Result #3 |
| --- | --- | --- | --- |
| MC-38.WT: | tumor (−) | tumor (−) | tumor (+) |
| MCA-102: | tumor (+) | tumor (−) | tumor (+) |

Indication from #1: Evidence of tumor-specific protective immunity
Indication from #2: Evidence of non-tumor specific immunity
Indication from #3: Lack of protective immunity If generation of tumor-specific protective immunity upon AIM II treatment is demonstrated, the following depletion experiment are performed to identify which leukocyte subpopulation is responsible for the tumor rejection. The mice will be treated with various mAb which recognize either CD4+ or CD8+ T cells, NK cells, granulocyte (Grl+), or specific cytokine such as IFNγ using techniques well known to those skilled in the art. Tumor growth in these antibody-treated mice is measured.

AIM II may also be used to treat rheumatoid arthritis (RA) by inhibiting the increase in angiogenesis or the increase in endothelial cell proliferation required to sustain an invading pannus in bone and cartilage as is often observed in RA. Endothelial cell proliferation is increased in the synovia of RA patients as compared to patients with osteoarthritis (OA) or unaffected individuals. Neovascularization is needed to sustain the increased mass of the invading pannus into bone and cartilage. Inhibition of angiogenesis is associated with a significant decrease in the severity of both early and chronic arthritis in animal models.

The AIM II polypeptide is believed to possess binding activities for a number of proteins, including several human cellular receptors. These receptors include the lymphotoxin-β-receptor (LT-β-R), TR2(also referred to as the Herpes virus entry mediator (HVEM) and ATAR), CD27, and TRANK (also referred to as receptor activator of nuclear factor-kappa B (RANK)).

Each of the receptors listed immediately above is involved in various physiological processes which may be modulated by the AIM II polypeptides of the invention. More specifically, the polypeptides of the invention can be used to stimulate or block the action of ligands which bind cellular receptors having AIM II binding activity (e.g., LT-β-R, TR2, CD27, and TRANK).

LT-β, which binds to the LT-β-R, has been implicated in the development of secondary lymphoid tissues and the maintenance of organized lymphoid tissues in adults. LT-β-R may, in some instances, function in conjunction with TR2 to mediate cellular responses and has been shown to be expressed in a number of tissues in the lung including a subpopulation of T-lymphocytes. LT-β-R has also been implicated in the formation of germinal centers and thus appears to be involved in humoral immune responses. Rennert et al., *Int. Immunol.* 9:1627–1639(1997).

The AIM II polypeptides of the invention may be employed to inhibit the formation of germinal centers and LT-β-R mediated humoral responses by blocking access of cellular ligands to LT-β-R. Further, polypeptides of the invention may stimulate the formation of germinal centers and LT-β-R mediated humoral responses by activating LT-β-R.

One skilled in the art would recognize that different portions of the AIM II polypeptide may have different effects on LT-β-R. One skilled in the art would also recognize that the effect that the AIM II polypeptides of the invention would have on LT-β-R would vary with the individual peptide and the effect it has when bound to LT-β-R. Methods for screening molecules having agonistic and antagonistic activities of cellular receptor are described above.

The core protein of hepatitis C virus (HCV) has also been shown to associate with LT-β-R and enhance signaling mediated by this receptor. Chen et al., *J. Virol.* 71:9417–9426(1997). Further, the interaction of this protein with LT-β-R may contribute to the chronically activated, persistent state of HCV-infected cells. The AIM II polypeptides of the invention may be employed to block HVC stimulation of LT-β-R and the pathology associated with this virus.

TR2 is a member of the tumor necrosis factor (TNF) receptor family which is expressed in a number of human tissues and cell lines. This protein is expressed constitutively and in relatively high levels in peripheral blood T cells, B cells, and monocytes. Kwon et al., *J. Biol. Chem.* 272:14272–14276(1997). TR2 serves a number of functions in vivo, including the mediation of Herpes viral entry into cells during infection. Further, a TR2-Fc fusion protein has been demonstrated to inhibit mixed lymphocyte reaction-mediated proliferation. These data suggest that the TR2 and its ligand play a role in T cell stimulation. It has been shown along these lines that overexpression of TR2 activates NF-κB and AP-1. This activation appears to occur through a TNF receptor-associated factor (TRAF)-mediated mechanism.

The AIM II polypeptides of the invention may be employed to inhibit T cell activation, and thus T cell mediated immune responses, by blocking access to TR2 by cellular ligands which activate this receptor. Similarly, polypeptides of the invention may stimulate T cell activation by activating TR2. As noted above for LT-β-R, one skilled in the art would recognize that different portions of the AIM II polypeptide may either inhibit or stimulate TR2 mediated cellular responses.

The AIM II polypeptides of the invention may also be employed to prevent or treat Herpes viral infections.

Expression of CD27, as well as its ligand CD70, is predominantly confined to lymphocytes. Further, CD27 has been shown to interact with CD70 and to be involved in the induction of IgE synthesis in B cells. Nagumo et al., *J. Immunol.* 161:6496–6502(1998). In addition, activation of CD27 may enhance IgE synthesis. Inhibition of the interaction between CD27 and CD70 thus may inhibit IgE production and allergic responses.

The AIM II polypeptides of the invention may be used for modulating immune responses. For example, AIM II polypeptides may be used to regulate the function of B cells by inhibiting the interaction between CD27 and CD70. AIM II polypeptides may thus bind to CD27 and inhibit B cell differentiation and proliferation, as well as the secretion of proteins (e.g., IgE) by these cells. Therefore, AIM II polypeptides may be employed to suppress IgE antibody formation in the treatment of IgE-induced immediate hypersensitivity reactions, such as allergic rhinitis (also know as hay fever), bronchial asthma, allergic asthma, anaphylaxis, atopic dermatitis and gastrointestinal food allergy.

CD27 is also believed to be the receptor for a pro-apoptotic protein commonly known as Siva. Pandanilam et al., *Kidney Int.* 54:1967–1975(1998). AIM II polypeptides of the invention may be employed to inhibit the interaction between Siva and CD27 and thus prevent Siva/CD27 mediated induction of apoptosis. Diseases associated with decreased cell survival, or increased apoptosis, include AIDS; neurodegenerative disorders (such as Alzheimer's disease, Parkinson's disease, Amyotrophic lateral sclerosis, Retinitis pigmentosa, Cerebellar degeneration); myelodysplastic syndromes (such as aplastic anemia), ischemic injury (such as that caused by myocardial infarction, stroke and reperfusion injury), toxin-induced liver disease (such as that caused by alcohol), septic shock, cachexia and anorexia.

AIM II polypeptides of the invention may also be employed to enhanced activation of the Siva/CD27 apoptotic pathway and thus facilitate the induction of apoptosis. Diseases associated with increased cell survival, or the inhibition of apoptosis, include cancers (such as follicular lymphomas, carcinomas with p53 mutations, and hormone-dependent tumors), autoimmune disorders (such as systemic lupus erythematosus, immune-related glomerulonephritis, and rheumatoid arthritis) and viral infections (such as herpes viruses, pox viruses and adenoviruses), information graft v. host disease, acute graft rejection, and chronic graft rejection.

While CD27 may be membrane-bound, a soluble form of CD27 is produced in the course of the immune response. Soluble CD27(sCD27) is found in a number of body fluids and may be measured to monitor local and systemic immune activation. Further, CD27 is expressed on human malignant B cells and high levels of sCD27 are present in the sera of patients with various B-cell malignancies. Kerstenet al., *Blood*87:1985–1989(1996). These elevated levels of sCD27 have been shown to strongly correlate with tumor load.

sCD27 has also been shown to be elevated in patients with a variety lymphoid malignancies and solid tumors of the central nervous system. These afflictions include primary central nervous system lymphoma (PCNSL) and lymphoid malignancies located in the meninges (e.g., acute lymphoblastic leukemia (ALL) and non-Hodgkin's lymphoma (NHL)).

Soluble CD27 has also been found to be elevated in patients with a number of non-hyperproliferative diseases. For example, sCD27 has been shown to be elevated in patients with untreated Graves' hyperthyroidism. Kallio et al., *J. Lab. Clin Med.* 132:478–482(1998). Further, increases in sCD27 serum levels have been found in patients with systemic lupus erythematosus (SLE) and this increase has been shown to be associated with the activity of the disease. Font et al., *Clin. Immunol. Immunopathol.* 81:239–243 (1996); Swaak et al., *Clin. Rheumatol.* 14:293–300(1995). Also, B cells from most patients with chronic lymphocytic leukemia (CLL) have been shown to co-express both membrane-bound and soluble CD27, as well as CD70. Ranheim et al., *Blood* 85:3556–3565(1995).

It has been postulated that sCD27 may prevent leukemic B cells from stimulating T cells via CD70, and thus may impair the ability of B cells to function as antigen-presenting cells. Ranheim et al., *Blood* 85:3556–3565(1995). Polypeptides of the invention may be employed to inhibit interactions between sCD27 and CD70, and, thus, to enhance the ability of B cells to act as antigen-presenting cells.

AIM II polypeptides of the invention may also be employed to treat diseases and afflictions associated with increase levels of sCD27. While not wishing to be bound to a mechanistic theory, AIM II polypeptides may be useful in treatment regimens for these conditions since it binding sCD27 and prevents it from interacting with cellular ligands.

AIM II polypeptides are also believed to bind to RANK. (See Anderson et al., *Nature* 390:175–179(1997).) RANK is a protein which has been implicated in osteoclast differentiation and regulation of interactions between T cells and dendritic cells. RANK apparently mediates its cellular effects via interaction with RANKL (also referred to as osteoprotegerin ligand (OPGL), TRANCE and ODF).

Mice having a disrupted RANKL gene show severe osteoporosis, exhibit defective tooth eruption, and lack osteoclasts. These mice also exhibit defects in T and B lymphocyte differentiation. Additionally, RANKL-deficient mice lack lymph nodes but exhibit normal splenic structure and Peyer's patches. These data indicate that RANKL mediated pathways regulate lymph node organogenesis, lymphocyte development, and osteoclast differentiation and proliferation.

There are two main classes of bone cells: cells which make bone, osteoblasts, and cells which resorb bone, osteoclasts. These cells each have very precise functions and the balance between their activities is critical to the maintenance of the skeletal system. For example, in human adults, between 10 to 15% of trabecular bone surfaces are covered with osteoid (new unmineralized bone made by osteoblasts) while about 4% have active resorptive surfaces. The dynamic nature of the continuing flux of bone cell activity is illustrated by the fact that approximately 18% of total skeletal calcium is often removed and deposited over a period of one year.

The AIM polypeptides of the invention may be employed to modulate osteoclast differentiation and proliferation, as well as bone development and degradation. Polypeptides of the invention may, for example, be employed to inhibit osteoclast differentiation and proliferation and, thus, may be employed to decease the rate of bone degradation. Inhibition of osteoclast differentiation and proliferation and bone degradation may be useful in the treatment of conditions such as osteoporosis, skeletal and dental abnormalities, bone cancers, osteoarthritis, osteogenesis imperfecta, and Hurler and Marfan syndromes. Polypeptides of the invention may also be employed in processes for reshaping bone and teeth and in periodontal reconstructions where lost bone replacement or bone augmentation is required, such as in a jaw bone and supplementing alveolar bone loss resulting from periodontal disease to delay or prevent tooth loss (see, e.g., Sigurdsson et al., *J. Periodontol.* 66:511–21(1995)).

The AIM II polypeptides of the invention may further be used to regulate T and B lymphocyte differentiation and proliferation. AIM II polypeptides may thus bind to RANK and inhibit the differentiation and proliferation of T and B lymphocyte, as well as the secretion of proteins (e.g., immunoglobins) from these cells. AIM II polypeptides may therefore be employed to suppress lymphocyte-mediated immune responses, for example, to prevent graft rejection. AIM II polypeptides may also be used to inhibit osteoclast differentiation and proliferation. AIM II polypeptides may thus be employed to treat diseases such as bone cancers.

The present invention also provides AIM II polypeptides which mimic one or more of the natural ligands of RANK and stimulate RANK-mediated cellular responses. These cellular responses include the activation of T and B lymphocyte differentiation and proliferation and induction of osteoclast differentiation. AIM II polypeptides may thus be employed to treat diseases such as infections (e.g., bacterial, viral, and protozoal infections). AIM II polypeptides may also be employed to enhance immune responses (e.g., in the treatment of AIDS and AIDS related complexes) and to increase bone degradation rates.

The AIM II polypeptide may be cleaved in vivo to form a soluble form of the molecule. As noted in Example 10, a cleavage site appears to be located between amino acid residues 82 and 83 of the sequence shown in SEQ ID NO:2. Cleavage of the AIM II polypeptide at this location is believed to result in the production of a soluble form of the molecule which comprises amino acids 83–240 in SEQ ID NO:2. Soluble forms of AIM II are especially useful for the treatment of diseases where systemic administration of these peptides is preferred. Further, soluble forms of AIM II are also useful for topical administration. The complete and mature AIM II polypeptides of the invention, as well as subfragments of these polypeptides, may be employed to treat afflictions associated with receptors and other ligands to which these molecules bind.

Modes of administration

It will be appreciated that conditions, such as those discussed above, can be treated by administration of AIM II protein. Thus, the invention further provides a method of treating an individual in need of an increased level of AIM II activity comprising administering to such an individual a pharmaceutical composition comprising an effective amount of an isolated AIM II polypeptide of the invention, effective to increase the AIM II activity level in such an individual.

As a general proposition, the total pharmaceutically effective amount of AIM II polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the AIM II polypeptide is typically administered at a dose rate of about 1 µg/kg/hour to about 50 µg/kg/hour, either by 1–4 injections per day or by continuous subcutaneous infusions, for example, using amini-pump. An intravenous bag solution may also be employed.

Pharmaceutical compositions containing the AIM II of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intra-articular injection and infusion.

In the treatment of rheumatoid arthritis, particularly preferred modes of administration of AIM II polypeptides of the present invention include, intradermal, subcutaneous and intra-articular injection and infusion. Preferably, AIM II polypeptide administered intra-articularly or intra-dermally per dose will be in the range of about 0.1 to about 1.0 mg/kg of patient body weight. Particularly preferred excipients include In addition to soluble AIM II polypeptides (i.e., AIM II polypeptides missing all or part of the transmembrane domain), AIM II polypeptides containing the transmembrane region can also be used when appropriately solubilized by including detergents, such as triton X-100, with buffer.

Chromosome Assays

The nucleic acid molecules of the present invention are also valuable for chromosome identification. The sequence is specifically targeted to and can hybridize with a particular location on an individual human chromosome. The mapping of DNAs to chromosomes according to the present invention is an important first step in correlating those sequences with genes associated with disease.

In certain preferred embodiments in this regard, the cDNA herein disclosed is used to clone genomic DNA of an AIM II protein gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1

Expression and Purification of AIM II in *E. coli*

A. Expression of AIM II with an N-terminal 6-His tag

The DNA sequence encoding the AIM II protein in the deposited cDNA clone is amplified using PCR oligonucleotide primers specific to the amino terminal sequences of the AIM II protein and to vector sequences 3' to the gene. Additional nucleotides containing restriction sites to facilitate cloning are added to the 5' and 3' sequences respectively.

A 22 kDa AIM II protein fragment (lacking the N-terminus and transmembrane region) is expressed using the following primers:

The 5' oligonucleotide primer has the sequence 5' GCGG-GATCCGGAGAGATGGTCACC 3' (SEQ ID NO:7) containing the underlined BamHI restriction site, which includes nucleotides 244–258 of the AIM II protein coding sequence in FIG. 1A (SEQ ID NO:1).

The 3' primer has the sequence:
5' CGCAAGCTTCCTTCACACCATGAAAGC 3' (SEQ ID NO:8) containing the underlined Hind III restriction site followed by nucleotides complementary to nucleotides 757–774 as shown in FIG. 1B (SEQ ID NO:1).

The entire AIM II protein can be expressed using the following primers:

The 5' oligonucleotide primer has the sequence:
5' GACC GGATCC ATG GAG GAG AGT GTC GTA CGG C 3' (SEQ ID NO:9) containing the underlined BamHI restriction site, which includes nucleotides 49–70 of the AIM II protein coding sequence in FIG. 1A (SEQ ID NO:1).

The 3' primer has the sequence:
5' CGC AAGCTT CCT TCA CAC CAT GAA AGC 3' (SEQ ID NO:10) containing the underlined HindIII restriction site followed by nucleotides complementary to nucleotides 756–783 as shown in FIG. 1B (SEQ ID NO:1).

The restriction sites are convenient to restriction enzyme sites in the bacterial expression vector pQE9, which are used for bacterial expression in these examples. (Qiagen, Inc. 9259 Eton Avenue, Chatsworth, Calif., 91311). pQE9 encodes ampicillin antibiotic resistance ("Amp$^r$") and contains a bacterial origin of replication ("ori"), an IPTG inducible promoter, a ribosome binding site ("RBS"), a 6-His tag and restriction enzyme sites.

The amplified AIM II DNA and the vector pQE9 both are digested with BamHI and Hind III and the digested DNAs are then ligated together. Insertion of the AIM II protein DNA into the restricted pQE9 vector places the AIM II protein coding region downstream of and operably linked to the vector's IPTG-inducible promoter and in-frame with an initiating AUG appropriately positioned for translation of AIM II protein.

B. Expression of AIM II with a C-terminal 6-His tag

The bacterial expression vector pQE60 is used for bacterial expression in this example. (QIAGEN, Inc., 9259 Eton Avenue, Chatsworth, Calif., 91311). pQE60 encodes ampicillin antibiotic resistance ("Amp$^r$") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that an inserted DNA fragment encoding a polypeptide expresses that polypeptide with the six His residues (i.e., a "6×His tag") covalently linked to the carboxyl terminus of that polypeptide.

The DNA sequence encoding the desired portion of the AIM II protein is amplified from the deposited cDNA clone using PCR oligonucleotide primers which anneal to the amino terminal sequences of the desired portion of the AIM II protein and to sequences in the deposited construct 3' to the cDNA coding sequence. Additional nucleotides containing restriction sites to facilitate cloning in the pQE60 vector are added to the 5' and 3' sequences, respectively.

For cloning the protein, the 5' primer has the sequence:
5' GACGC CCATGG AG GAG GAG AGT GTC GTA CGG C 3' (SEQ ID NO:17) containing the underlined NcoI restriction site followed by nucleotides complementary to the amino terminal coding sequence of the AIM II sequence in FIG. 1A. One of ordinary skill in the art would appreciate, of course, that the point in the protein coding sequence where the 5' primer begins may be varied to amplify a DNA segment encoding any desired portion of the complete protein (shorter or longer). The 3' primer has the sequence:

5' GACC GGATCC CAC CAT GAA AGC CCC GAA GTA AG 3' (SEQ ID NO:18) containing the underlined BamHI restriction site followed by nucleotides complementary to the 3' end of the coding sequence immediately before the stop codon in the AIM II DNA sequence in FIG. 1B, with the coding sequence aligned with the restriction site so as to maintain its reading frame with that of the six His codons in the pQE60 vector.

The amplified AIM II DNA fragment and the vector pQE60 are digested with BamHI and NcoI and the digested DNAs are then ligated together. Insertion of the AIM II DNA into the restricted pQE60 vector places the AIM II protein coding region downstream from the IPTG-inducible promoter and in-frame with an initiating AUG and the six histidine codons.

C. Expression of AIM II Deletion Mutant with an N-terminal 6-His tag

The DNA sequence encoding the AIM II protein in the deposited cDNA clone was amplified using PCR oligonucleotide primers specific to sequences of the AIM II protein and to vector sequences 3' to the gene. Additional nucleotides containing restriction sites to facilitate cloning were added to the 5' and 3' sequences respectively.

In particular, an N-terminal deletion AIM II mutant (Met (68) to Val(240) in SEQ ID NO:2) was constructed using the following primers:

The 5' oligonucleotide primer has the sequence:
5'-GGG GGA TCC ATG GTC ACC CGC CTG CC-3' (SEQ ID NO:21) containing the underlined BamHI restriction site, and includes 17 nucleotides of the AIM II protein coding sequence in FIG. 1A (SEQ ID NO:1).

The 3' primer has the sequence:
5'-GGG AAG CTT CAC CAT GAA AGC CCC G-3' (SEQ ID NO:22) containing the underlined Hind III restriction site followed by nucleotides complementary to nucleotides 753–768 as shown in FIG. 1B (SEQ ID NO:1).

These restriction sites are convenient to restriction enzyme sites in the bacterial expression vector pQE9, which are used for bacterial expression in this example. (Qiagen, Inc. 9259 Eton Avenue, Chatsworth, Calif., 91311). pQE9 encodes ampicillin antibiotic resistance ("Amp$^r$") and contains a bacterial origin of replication ("ori"), an IPTG inducible promoter, a ribosome binding site ("RBS"), a 6-His tag and restriction enzyme sites.

The amplified AIM II (aa 68–240) DNA and the vector pQE9 both were digested with BamHI and Hind III and the digested DNAs were then ligated together. Insertion of the AIM II (aa 68–240) protein DNA into the restricted pQE9 vector places the AIM II protein coding region downstream of and operably linked to the vector's IPTG-inducible promoter and in-frame with an initiating AUG appropriately positioned for translation of AIM II deletion protein.

Transformation of the Bacteria:

The ligation mixture from the 6-His tagged expression constructs made in A, B or C, above, is transformed into competent *E coli* cells using standard procedures. Such procedures are described in Sambrook et al, Molecular Cloning: a Laboratory Manual, 2nd Ed.; Cold Spring Harbor Laboratory Press, Cold Spring Harbor, N.Y. (1989). *E. coli* strain M15/rep4, containing multiple copies of the plasmid pREP4, which expresses lac repressor and confers kanamycin resistance ("Kan$^r$"), is used in carrying out the illustrative example described herein. This strain, which is only one of many that are suitable for expressing AIM II protein, is available commercially from Qiagen.

Transformants are identified by their ability to grow on LB plates in the presence of ampicillin and kanamycin. Plasmid DNA is isolated from resistant colonies and the identity of the cloned DNA confirmed by restriction analysis.

Clones containing the desired constructs are grown overnight ("O/N") in liquid culture in LB media supplemented with both ampicillin (100 µg/ml) and kanamycin (25 µg/ml). The O/N culture is used to inoculate a large culture, at a dilution of approximately 1:100 to 1:250. The cells are grown to an optical density at600 nm ("OD600") of between 0.4 and 0.6. Isopropyl-B-D-thiogalactopyranoside ("IPTG") is then added to a final concentration of 1 mM to induce transcription from lac repressor sensitive promoters, by inactivating the lacI repressor. Cells subsequently are incubated further for 3 to 4 hours. Cells then are harvested by centrifugation and disrupted, by standard methods. Inclusion bodies are purified from the disrupted cells using routine collection techniques, and protein is solubilized from the inclusion bodies into 8M urea. The 8M urea solution containing the solubilized protein is passed over a PD-10 column in 2×phosphate-buffered saline ("PBS"), thereby removing the urea, exchanging the buffer and refolding the protein. The protein is purified by a further step of chromatography to remove endotoxin. Then, it is sterile filtered. The sterile filtered protein preparation is stored in 2×PBS at a concentration of 95 µg/ml.

D. Expression and Purification of Full Length AIM II without a 6-His tag

The bacterial expression vector pQE60 is used for bacterial expression in this example. (QIAGEN, Inc., 9259 Eton Avenue, Chatsworth, Calif., 91311). pQE60 encodes ampicillin antibiotic resistance ("Amp$^r$") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that a DNA fragment encoding a polypeptide may be inserted in such as way as to produce that polypeptide with the six His residues (i.e., a "6×His tag") covalently linked to the carboxyl terminus of that polypeptide. However, in this example, the polypeptide coding sequence is inserted such that translation of the six His codons is prevented and, therefore, the polypeptide is produced with no 6×His tag.

The DNA sequence encoding the desired portion of the AIM II protein is amplified from the deposited cDNA clone using PCR oligonucleotide primers which anneal to the amino terminal sequences of the desired portion of the AIM II protein and to sequences in the deposited construct 3' to the cDNA coding sequence. Additional nucleotides containing restriction sites to facilitate cloning in the pQE60 vector are added to the 5' and 3' sequences, respectively.

For cloning the protein, the 5' primer has the sequence 5' GACGC CCATGG AG GAG GAG AGT GTC GTA CGG C 3' (SEQ ID NO:17) containing the underlined NcoI restriction site including nucleotides of the amino terminal coding region of the AIM II sequence in FIG. 1A. One of ordinary skill in the art would appreciate, of course, that the point in the protein coding sequence where the 5' primer begins may be varied to amplify a desired portion of the complete protein (i.e., shorter or longer). The 3' primer has the sequence 5' CGC AAGCTT CCTT CAC ACC ATG AAA GC 3' (SEQ ID NO:19) containing the underlined Hind III restriction site followed by nucleotides complementary to the 3' end of the non-coding sequence in the AIM II DNA sequence in FIG. 1B (SEQ ID NO:1).

The amplified AIM II DNA fragments and the vector pQE60 are digested with NcoI and Hind III and the digested DNAs are then ligated together. Insertion of the AIM II DNA into the restricted pQE60 vector places the AIM II protein coding region including its associated stop codon downstream from the IPTG-inducible promoter and in-frame with an initiating AUG. The associated stop codon prevents translation of the six histidine codons downstream of the insertion point.

E. Construction of an N-terminal AIM II Deletion Mutant

For cloning an AIM II deletion mutant (Met(68) to Val(240) in SEQ ID NO:2), the 5' primer has the sequence 5'-GGG CCA TGG ATG GTC ACC CGC CTG CC-3' (SEQ ID NO:23) containing the underlined NcoI restriction site, and includes followed by 17 nucleotides of the AIM II protein coding sequence in FIG. 1A. The 3' primer has the sequence 5'-GGG AAG CTT CAC CAT GAA AGC CCC G-3' (SEQ ID NO:22) containing the underlined Hind III restriction site followed by nucleotides complementary to nucleotides 753 to 768 in FIG. 1B (SEQ ID NO:1).

The amplified AIM II (aa 68–240) DNA fragments and the vector pQE60 were digested with NcoI and Hind III and the digested DNAs were then ligated together. Insertion of the AIM II (aa 68–240) DNA into the restricted pQE60 vector places the AIM II (aa 68–240) protein coding region downstream from the IPTG-inducible promoter and in-frame with an initiating AUG. The HindIII digestion removes the six histidine codons downstream of the insertion point.

F. Construction of an N-terminal AIM II Deletion Mutant

For cloning an AIM II deletion mutant (Ala(101) to Val(240) in SEQ ID NO:2), the 5' primer has the sequence 5'-GGG CCA TGG GCC AAC TCC AGC TTG ACC-3' (SEQ ID NO:24) containing the underlined NcoI restriction site including nucleotides 349–366 in the AIM II protein coding sequence in FIG. 1A. One of ordinary skill in the art would appreciate, of course, that the point in the protein coding sequence where the 5' primer begins may be varied to amplify a desired portion of the complete protein (i.e., shorter or longer). The 3' primer has the sequence 5'-GGG AAG CTT CAC CAT GAA AGC CCC G-3' (SEQ ID NO:22) containing the underlined Hind III restriction site followed by nucleotides complementary nucleotides 755–768 of the AIM II DNA sequence in FIG. 1B.

The amplified AIM II (aa 101–240) DNA fragments and the vector pQE60 were digested with NcoI and Hind III and the digested DNAs are then ligated together. Insertion of the AIM II (aa 101–240) DNA into the restricted pQE60 vector places the AIM II (aa 101–240) protein coding region downstream from the IPTG-inducible promoter and in-frame with an initiating AUG. The HindIII digestion removes the six histidine codons downstream of the insertion point.

G. Purification of AIM II from E coil

A polynucleotide sequence encoding a soluble fragment of AIM II (corresponding to amino acid residues L83-V240 of SEQ ID NO:2) was cloned into the HGS E. coli expression vector pHE4. The resulted plasmid DNA (pHE4: AIMII.L83-V240) was used to transform SG13009 E. coli host cells. The bacterial transformants were grown in LB medium containing kanamycin. Upon IPTG induction, recombinant AIM II was expressed in E. coli as an insoluble protein deposited in inclusion bodies The E. coli cell paste was resuspended in a buffer containing 0.1M Tris-HCl pH7.4, 2 mM CaCl2 and was lysed by passing twice through a microfluidizer (Microfluidics, Newton, Mass.) at 6000–8000 psi. The lysed sample was mixed with NaCl to a final concentration of 0.5M and then centrifuged at 7000×g for 20 minutes. The resulting pellet was washed again with the same buffer plus 0.5M NaCl and then centrifuged at 7000×g again for 20 minutes.

The partially purified inclusion bodies were then resuspended for 2–4 hours at 20–25 $\mu$C in 2.0 M guanidine hydrochloride containing 100 mM Tris pH 7.4, 2 mM CaCl2, 5 mM Cysteine and centrifuged. The resulting pellet was then resuspended for 48–72 hours at 4 $\mu$C in 3.0–3.5 M guanidine hydrochloride containing 100 mM Tris pH 7.4, 2 mM CaCl2, with or without 5 mM Cysteine. At this time, a portion of AIM II was solublized and remained in the soluble phase after 7,000×g centrifugation.

The 3M guanidine hydrochloride extract was quickly diluted with 20–30 volumes of a buffer containing 50 mM Tris-HCl pH8, 150 mM sodium chloride. Detergents such as Tween-20, CHAPS can be added to increase the refold efficacy. Afterwards the mixture was placed at 4 $\mu$C without mixing for 2 to 7 days prior to the chromatographic purification steps described below.

Liquid Chromatographic Purification of AIM II

The diluted AIM II sample was clarified using a 0.45 $\mu$m sterile filter. The AIM II protein was then adjusted to pH6–6.8 with 0.5M MES and chromatographed over a strong cation exchange (POROS HS-50) column. The HS column was washed first with 6–10 column volume of a buffer containing 50 mM MES-NaOH pH 6.6 and 150 mM sodium chloride. The bound protein was eluted using 3 to 5 column volume of a stepwise gradient of 300 mM, 700 mM, 1500 mM sodium chloride in 50 mM MES at pH 6.6.

The HS fraction eluted with 0.7 M sodium chloride was diluted 3-fold with water.

Transformation of the Bacteria:

The ligation mixture from expression constructs made in D, E or F, above were transformed into competent E. coli cells using standard procedures such as those described in Sambrook et al, Molecular Cloning: a Laboratory Manual, 2nd Ed.; Cold Spring Harbor Laboratory Press, Cold Spring Harbor, N.Y. (1 989). E. coli strain M15/rep4, containing multiple copies of the plasmid pREP4, which expresses the lac repressor and confers kanamycin resistance ("Kan"'"), was used in carrying out the illustrative example described herein. This strain, which was only one of many that are suitable for expressing AIM II protein, was available commercially from QIAGEN, Inc., supra. Transformants were identified by their ability to grow on LB plates in the presence of ampicillin and kanamycin. Plasmid DNA was isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 $\mu$g/ml) and kanamycin (25 $\mu$g/ml). The O/N culture was used to inoculate a large culture, at a dilution of approximately 1:25 to 1:250. The cells were grown to an optical density at 600 nm ("OD600") of between 0.4 and 0.6. Isopropyl-b-D-thiogalactopyranoside ("IPTG") was then added to a final concentration of 1 mM to induce transcription from the lac repressor sensitive promoter, by inactivating the lacI repressor. Cells subsequently were incubated further for 3 to 4 hours. Cells then were harvested by centrifugation.

The cells were then stirred for 3–4 hours at 4° C. in 6M guanidine-HCl, pH8. The cell debris was removed by centrifugation, and the supernatant containing the AIM II was dialyzed against 50 mM Na-acetate buffer pH6, supplemented with 200 mM NaCl. Alternatively, the protein can be successfully refolded by dialyzing it against 500 mM NaCl, 20% glycerol, 25 mM Tris/HCl pH7.4, containing protease inhibitors. After renaturation the protein can be purified by ion exchange, hydrophobic interaction and size exclusion chromatography. Alternatively, an affinity chromatography step such as an antibody column can be used to obtain pure AIM II protein. The purified protein is stored at 4° C. or frozen at −80° C.

Example 2

Cloning and Expression of AIM II Protein in a Baculovirus Expression System

A. Construction of a Full Length AIM II Protein:

The cDNA sequence encoding the full length AIM II protein in the deposited clone is amplified using PCR oligonucleotide primers corresponding to the 5' and 3' sequences of the gene:

The 5' primer has the sequence 5' GCT CCA GGA TCC GCC ATC ATG GAG GAG AGT GTC GTA CGG C 3' (SEQ ID NO:11) containing the underlined BamHI restriction enzyme site followed by 22 bases (i.e., nucleotides 49–70) of the coding region for the AIM II protein in FIG. 1A. Inserted into an expression vector, as described below, the 5' end of the amplified fragment encoding AIM II provides an efficient signal peptide. An efficient signal for initiation of translation in eukaryotic cells, as described by Kozak, M., *J Mol. Biol*. 196:947–950(1987) is appropriately located in the vector portion of the construct.

The 3' primer has the sequence 5' GA CGC GGT ACC GTC CAA TGC ACC ACG CTC CTT CCT TC 3' (SEQ ID NO:12) containing the underlined Asp718 restriction site followed by nucleotides complementary to 770–795 nucleotides of the AIM II set out in FIG. 1A.

The amplified fragment is isolated from a 1% agarose gel using a commercially available kit ("Geneclean," BIO 101 Inc., La Jolla, Calif.). The fragment then is digested with BamHI and Asp718 and again is purified on a 1% agarose gel. This fragment is designated herein F2.

The vector pA2-GP is used to express the AIM II protein in the baculovirus expression system, using standard methods, as described in Summers et al., A Manual of Methods for Baculovirus Vectors and Insect Cell Culture Procedures, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites. The signal peptide of AcMNPV gp67, including the N-terminal methionine, is located just upstream of a BamHI site. The polyadenylation site of the simian virus 40 ("SV40") is used for efficient polyadenylation. For an easy selection of recombinant virus the beta-galactosidase gene from *E. coli* is inserted in the same orientation as the polyhedrin promoter and is followed by the polyadenylation signal of the polyhedrin gene. The polyhedrin sequences are flanked at both sides by viral sequences for cell-mediated homologous recombination with wild-type viral DNA to generate viable virus that express the cloned polynucleotide.

Many other baculovirus vectors could be used in place of pA2-GP, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., *Virology* 170: 31–39, among others.

The plasmid is digested with the restriction enzyme BamHI and Asp718 and then is dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V".

Fragment F2 and the dephosphorylated plasmid V2 are ligated together with T4 DNA ligase. *E. coli* HB101 cells are transformed with ligation mix and spread on culture plates. Bacteria are identified that contain the plasmid with the human AIM II gene by digesting DNA from individual colonies using XbaI and then analyzing the digestion product by gel electrophoresis. The sequence of the cloned fragment is confirmed by DNA sequencing. This plasmid is designated herein pBacAIM II.

B. Construction of an N-terminal AIM II Deletion Mutants:

In this illustrative example, the plasmid shuttle vector pA2 GP was used to insert the cloned DNA encoding the an N-terminal deletion of the AIM II protein into a baculovirus to express an AIM II mutant (Gln(60) to Val(240)) and AIM II mutant (Ser(79) to Val(240)) in SEQ ID NO:2, using a baculovirus leader and standard methods as described in Summers et al., A Manual of Methods for Baculovirus Vectors and Insect Cell Culture Procedures, Texas Agricultural Experimental Station Bulletin No. 1555 (1987). This expression vector contains the strong polyhedrin promoter of the *Autographa californica* nuclear polyhedrosis virus (AcMNPV) followed by the secretory signal peptide (leader) of the baculovirus gp67 protein and convenient restriction sites such as BamHI, XbaI and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate viable virus that expresses the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39.

The cDNA sequence encoding the AIM II (Gln(60)to Val(240), FIG. 1A (SEQ ID NO:2), was amplified using PCR oligonucleotide primers corresponding to the 5' and 3' sequences of the gene.

The 5' primer has the sequence:

5'-GGG GGA TCC CGCA GCT GCA CTG GCG TCT AGG-3' (SEQ ID NO:25) containing the underlined BamHI restriction enzyme site followed by 20 nucleotides (i.e., nucleotides 225–245) encoding the AIM II protein shown in FIG. 1A and B, beginning with amino acid 60 of the protein. The 3' primer has the sequence 5'-GGG TCT AGA CAC CAT GAA AGC CCC G-3' (SEQ ID NO: 26) containing the underlined XbaI restriction site followed by nucleotides complementary to nucleotides 753–768 in FIG. 1B (SEQ ID NO:1).

The amplified fragment was isolated from a 1% agarose gel using a commercially available kit ("Geneclean," BIO 101 Inc., La Jolla, Calif.). The fragment then was digested with BamHI and XbaI and again was purified on a 1% agarose gel. This fragment was designated herein "F1".

The plasmid was digested with the restriction enzymes BamHI and XbaI and optionally, can be dephosphorylated using calf intestinal phosphatase, using routine procedures known in the art. The DNA was then isolated from a 1% agarose gel using a commercially available kit ("Geneclean" BIO 101 Inc., La Jolla, Calif.). This vector DNA was designated herein "V1".

Fragment F1 and the dephosphorylated plasmid V1 were ligated together with T4 DNA ligase. E. coli HB101 or other suitable E. coli hosts such as XL-1 Blue (Stratagene Cloning Systems, La Jolla, Calif.) cells were transformed with the ligation mixture and spread on culture plates. Bacteria were identified that contain the plasmid with the human AIM II gene using the PCR method, in which one of the primers that was used to amplify the gene and the second primer was from well within the vector so that only those bacterial colonies containing the AIM II gene fragment will show amplification of the DNA. The sequence of the cloned fragment was confirmed by DNA sequencing. This plasmid was designated herein pBacAIM II (aa 60–240).

The cDNA sequence encoding the AIM II (Ser(79)to Val(240), FIG. 1A (SEQ ID NO:2), was amplified using PCR oligonucleotide primers corresponding to the 5' and 3' sequences of the gene.

The 5' primer has the sequence:
5' cgc <u>GGATCC</u> C TCCTGGGAGCAGCTGATAC 3' (SEQ ID NO:27) containing the underlined BamHI restriction enzyme site followed by nucleotides 283–301 encoding the AIM II protein shown in FIG. 1A and B, beginning with amino acid 79 of the protein. The 3' primer has the sequence:
5'-cgc <u>GGATCC TCA</u> CACCATGAAAGC 3' (SEQ ID NO:29) containing the underlined BamHI restriction site followed by nucleotides complementary to nucleotides 757–771 in FIG. 1B (SEQ ID NO:1).

The amplified fragment was isolated from a 1% agarose gel using a commercially available kit ("Geneclean," BIO 101 Inc., La Jolla, Calif.). The fragment then was digested with BamHI and again was purified on a 1% agarose gel. This fragment was designated herein "F1".

The plasmid was digested with the restriction enzymes BamHI and optionally, can be dephosphorylated using calf intestinal phosphatase, using routine procedures known in the art. The DNA was then isolated from a 1% agarose gel using a commercially available kit ("Geneclean" BIO 101 Inc., La Jolla, Calif.). This vector DNA was designated herein "V1".

Fragment F1 and the dephosphorylated plasmid V1 were ligated together with T4 DNA ligase. E. coli HB 101 or other suitable E. coli hosts such as XL-1 Blue (Stratagene Cloning Systems, La Jolla, Calif.) cells were transformed with the ligation mixture and spread on culture plates. Bacteria were identified that contain the plasmid with the mutant AIM II gene using the PCR method, in which one of the primers that was used to amplify the gene and the second primer was from well within the vector so that only those bacterial colonies containing the AIM II gene fragment will show amplification of the DNA. The sequence of the cloned fragment was confirmed by DNA sequencing. This plasmid was designated herein pBacAIM II (aa 79–240).

C. Transfection of the Baculovirus Vectors Containing AIM II Sequences:

5 µg of the plasmid either pBac AIM II or pBacAIM II (aa 60–240) was co-transfected with 1.0 µg of a commercially available linearized baculovirus DNA ("BaculoGold™ baculovirus DNA", Pharmingen, San Diego, Calif.), using the lipofection method described by Felgner et al., Proc. Natl. Acad. Sci. USA 84: 7413–7417(1987). 1 µg of BaculoGold™ virus DNA and 5 µg of the plasmid pBac AIM II or pBacAIM II (aa 60–240) was mixed in a sterile well of a microtiter plate containing 50 µl of serum-free Grace's medium (Life Technologies Inc., Gaithersburg, Md.). Afterwards 10 µl Lipofectin plus 90 µl Grace's medium were added, mixed and incubated for 15 minutes at room temperature. Then the transfection mixture was added drop-wise to Sf9 insect cells (ATCC CRL 1711) seeded in a 35 mm tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum is added. The plate was put back into an incubator and cultivation was continued at 27° C. for four days.

After four days the supernatant was collected and a plaque assay was performed, as described by Summers and Smith, cited above. An agarose gel with "Blue Gal" (Life Technologies Inc., Gaithersburg) was used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10).

Four days after serial dilution, the virus was added to the cells. After appropriate incubation, blue stained plaques are picked with the tip of an Eppendorf pipette. The agar containing the recombinant viruses was then resuspended in an Eppendorf tube containing 200 µl of Grace's medium. The agar was removed by a brief centrifugation and the supernatant containing the recombinant baculovirus is used to infect Sf9 cells seeded in 35 mm dishes. Four days later the supernatants of these culture dishes were harvested and then they were stored at 4° C. A clone containing properly inserted hESSB I, II and III was identified by DNA analysis including restriction mapping and sequencing. This was designated herein as V-AIM II or V-AIM II (aa 60–240).

Sf9 cells were grown in Grace's medium supplemented with 10% heat-inactivated FBS. The cells were infected with the recombinant baculovirus V-AIM II or V-AIM II (aa60–240) at a multiplicity of infection ("MOI") of about 2 (about 1 to about 3). Six hours later the medium was removed and was replaced with SF900 II medium minus methionine and cysteine (available from Life Technologies Inc., Gaithersburg). 42 hours later, 5 µCi of $^{35}$S-methionine and 5 µCi$^{35}$S-cysteine (available from Amersham) were added. The cells were further incubated for 16 hours and then they were harvested by centrifugation, lysed and the labeled proteins were visualized by SDS-PAGE and autoradiography.

Example 3

Cloning and Expression in Mammalian Cells

Most of the vectors used for the transient expression of the AIM II protein gene sequence in mammalian cells should carry the SV40 origin of replication. This allows the replication of the vector to high copy numbers in cells (e.g., COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular signals can also be used (e.g., human actin promoter). Suitable expression vectors for use in practicing the present invention include, for example, vectors such as pSVL and pMSG (Pharmacia, Uppsala, Sweden), pRSVcat (ATCC 37152), pSV2 dhfr (ATCC 37146) and pBC12MI (ATCC 67109). Mammalian host cells that could be used include, human HeLa, 283, H9 and Jurkart cells, mouse NIH3T3 and C127 cells, Cos 1, Cos 7 and CV1, African green monkey cells, quail QC 1–3 cells, mouse L cells and Chinese hamster ovary cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Another useful selection marker is the enzyme glutamine synthase (GS) (Murphy et al., *Biochem J*. 227:277–279(1991); Bebbington et al., *Bio/Technology* 10:169–175(1992)). Using these markers, the mammalian cells are grown in selective medium and the cells with the highest resistance are selected. These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., *Molecular and Cellular Biology*, 438–447(March, 1985)) plus a fragment of the CMV-enhancer (Boshart et al., *Cell* 41:521–530(1985)). Multiple cloning sites, e.g.,with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pAIM II HA, is made by cloning a cDNA encoding AIM II into the expression vector pcDNAI/Amp (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polyline.

A DNA fragment encoding the AIM II protein and an HA tag fused in frame to its 3' end is cloned into the polyline region of the vector so that recombinant protein expression is directed by the CMV promoter. The HA tag corresponds to an epitope derived from the influenza hemagglutinin protein described by Wilson et al., *Cell* 37: 767(1984). The fusion of the HA tag to the target protein allows easy detection of the recombinant protein with an antibody that recognizes the HA epitope.

The plasmid construction strategy is as follows. The AIM II cDNA of the deposited clone is amplified using primers that contain convenient restriction sites, much as described above regarding the construction of expression vectors for expression of AIM II in *E. coli*. To facilitate detection, purification and characterization of the expressed AIM II, one of the primers contains a hemagglutinin tag ("HA tag") as described above.

Suitable primers include the following, which are used in this example. The 5' primer, containing the underlined BamHI site, and an AUG start codon has the following sequence:

5' GAG <u>CTC GGA</u> TCC GCC ATC ATG GAG GAG AGT GTC GTA CGGC 3' (SEQ ID NO:13).

The 3' primer, containing the underlined XbaI site, a stop codon, 9 codons thereafter forming the hemagglutinin HA tag, and 33 bp of 3' coding sequence (at the 3' end) has the following sequence:

5' GAT <u>GTT CTA GAA</u> AGC GTA GTC TGG GAC GTC GTA TGG GTA CAC CAT GAA AGC CCC GAA GTA AGA CCG GGT AC 3' (SEQ ID NO:14).

The PCR amplified DNA fragment and the vector, pcDNAI/Amp, are digested with HindII and XhoI and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis and gel sizing for the presence of the AIM II-encoding fragment.

For expression of recombinant AIM II, COS cells are transfected with an expression vector, as described above, using DEAE-DEXTRAN, as described, for instance, in Sambrook et al., Molecular Cloning: a Laboratory Manual, Cold Spring Laboratory Press, Cold Spring Harbor, N.Y. (1989). Cells are incubated under conditions for expression of AIM II by the vector.

Expression of the AIM II HA fusion protein is detected by radiolabelling and immunoprecipitation, using methods described in, for example Harlow et al., Antibodies: A Laboratory Manual, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1%NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

Example 3(b)

Cloning and Expression in CHO Cells

The vector pC4 is used for the expression of AIM II protein. Plasmid pC1 is a derivative of the plasmid pSV2- dhfr [ATCC Accession No. 37146]. Both plasmids contain the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357–1370, Hamlin, J. L. and Ma, C. 1990, Biochem. et Biophys. Acta, 1097:107–143, Page, M. J. and Sydenham, M. A. 1991, *Biotechnology Vol.* 9:6468). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC4 contains for expressing the gene of interest the strong promoter of the long terminal repeat (LTR) of the Rous Sarcoma Virus (Cullen, et al., *Molecular and Cellular Biology*, March 1985:438–447) plus a fragment isolated from the enhancer of the immediate early gene of human cytomegalovirus (CMV) (Boshart et al., *Cell* 41:521–530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the AIM II in a regulated way in mammalian cells (Gossen, M., & Bujard, H. 1992, *Proc. Natl. Acad. Sci. USA* 89: 5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes BamHI and Asp718 and then dephosphorylated using calf intestinal phosphatase by procedures known in the art. The vector is then isolated from a 1% agarose gel.

The DNA sequence encoding the complete AIM II protein is amplified using PCR oligonucleotide primers corresponding to the 5' and 3' sequences of the gene. The 5' primer has the sequence:

5' GCT CCA GGA TCC GCC ATC ATG GAG GAG AGT GTC GTA CGG C3' (SEQ ID NO:15) containing the underlined BamHI restriction enzyme site followed by an efficient signal for initiation of translation in eukaryotes, as described by Kozak, M., *J. Mol. Biol.* 196:947–950 (1987), and 22 bases (i.e., nucleotides 49–70) of the coding region of the AIM II protein shown in FIG. 1A (SEQ ID NO:1). The 3' primer has the sequence:

5' GA CGC GGT ACC GTC CAA TGC ACC ACG CTC CTT CCT TC 3' (SEQ ID NO:16) containing the underlined Asp718 restriction site followed by nucleotides complementary to nucleotides 770–795 of the AIM II gene shown in FIG. 1B (SEQ ID NO:1).

The amplified fragment is digested with the endonucleases BamHI and Asp718 and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Example 3(c)

Cloning and Expression of an AIM II N-terminal Deletion in CHO Cells

The vector pC4 was used for the expression of AIM II mutant (Met(68)-Val(240) in SEQ ID NO:2) protein. The plasmid pC4 was digested with the restriction enzymes BamHI and then dephosphorylated using calf intestinal phosphatase by procedures known in the art. The vector was then isolated from a 1% agarose gel.

The DNA sequence encoding the AIM II (aa 68–240) protein was amplified using PCR oligonucleotide primers corresponding to the 5' and 3' sequences of the gene. The following 5' primer was used:

5' GAC AGT GGA TCC GCC ACC ATG GTC ACC CGC CTG CCT GAC GGA C 3' (SEQ ID NO:40) containing the underlined BamHI restriction enzyme site followed by an efficient signal for initiation of translation in eukaryotes, as described by Kozak, M., *J. Mol. Biol.* 196:947–950(1987), and nucleotides 202–226 in the coding region for the AIM II polypeptide shown in FIG. 1A (SEQ ID NO:1). The following 3' primer was used: (BamHI+stop codon (italics)) 5'-GGG GGA TCC *TGA* CAC CAT GAA AGC CCC G-3' (SEQ ID NO:28) containing the underlined BamHI restriction site followed by nucleotides complementary nt 753–768 shown in FIG. 1B (SEQ ID NO:1).

The amplified fragment was digested with the endonucleases BamHI and then purified again on a 1% agarose gel. The isolated fragment and the dephosphorylated vector were then ligated with T4 DNA ligase. *E. coli* HB101 or XL-1 Blue cells were then transformed and bacteria were identified that contain the fragment inserted into plasmid pC4 using, for instance, restriction enzyme analysis.

The vector pC4/Ckβ8 (a pC4 construct wherein the Ckβ8 signal peptide was first cloned into the pC4 vector with a BamHI site at the 3' end of Ckβ8 signal sequence) was used for the expression of AIM II mutant (Trp(80)-Val(240) in SEQ ID NO:2) protein. The plasmid pC4/Ckβ8 was digested with the restriction enzymes BamHI and then dephosphorylated using calf intestinal phosphatase by procedures known in the art. The vector was then isolated from a 1% agarose gel.

The DNA sequence encoding the AIM II (aa 80–240) protein was amplified using PCR oligonucleotide primers corresponding to the 5' and 3' sequences of the gene. The following 5' primer was used:

5' cgc GGATCC TGGGAGCAGCTGATAC 3' (SEQ ID NO:41) containing the underlined BamHI restriction enzyme site followed by nucleotides 286–301 in the coding region for the AIM II polypeptide shown in FIG. 1A (SEQ ID NO:1).

The following 3' primer was used:

5' cgc GGATCC TCA CACCATGAAAGC 3' (SEQ ID NO:29) containing the underlined BamHI restriction site followed by nucleotides complementary nt 757–771 shown in FIG. 1B (SEQ ID NO:1).

The amplified fragment was digested with the endonucleases BamHI and then purified again on a 1% agarose gel.

The isolated fragment and the dephosphorylated vector were then ligated with T4 DNA ligase. *E. coli* HB101 or XL-1 Blue cells were then transformed and bacteria were identified that contain the fragment inserted into plasmid pC4/Ckβ8 using, for instance, restriction enzyme analysis.

CHO Cell Transfection:

Chinese hamster ovary cells lacking an active DHFR gene are used for transfection. 5 μg of the expression pC4 vectors described above are cotransfected with 0.5 μg of the plasmid pSV2-neo using lipofectin (Felgner et al., supra). The plasmid pSV2 neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 μM, 20 μM). The same procedure is repeated until clones are obtained which grow at a concentration of 100–200 μM. Expression of the desired gene product is analyzed, for instance, by SDS-PAGE and Western blot or by reverse phase HPLC analysis.

Example 3(d)

Cloning and Expression of an AIM II N-terminal Deletion in CHO Cells

The vector pC4 was used for the expression of AIM II mutant (Met(68)-Val(240) in SEQ ID NO:2) protein that includes a C-terminal Fc immunoglobulin region. In this construct, the Ckμ8 signal peptide was first cloned into pC4 with a BamHI site at the 3' end of Ckμ8. The Fc fragment flanked by BamHI and XbaI sites was cloned into the vector resulting in pC4/Ckμ8/Fc. The AIM-II fragment was then cloned between the CK-μ8 leader and the Fc fragment in the BamHI site.

The plasmid pC4 was digested with the restriction enzymes BamHI and then dephosphorylated using calf intestinal phosphatase by procedures known in the art. The vector was then isolated from a 1% agarose gel.

The DNA sequence encoding the complete AIM II (aa 68–240) protein was amplified using PCR oligonucleotide primers corresponding to the 5' and 3' sequences of the gene. The following 5' primer was used: 5' GAC AGT GGA TCC GCC ACC ATG GTC ACC CGC CTG CCT GAC GGA C 3' (SEQ ID NO: 40) containing the underlined BamHI restriction enzyme site followed by an efficient signal for initiation of translation in eukaryotes, as described by Kozak, M., *J. Mol. Biol.* 196:947–950(1987), and nucleotides 202–226 in the coding region for the AIM II polypeptide shown in FIG. 1A (SEQ ID NO:1). The following 3' primer was used: (BamHI) 5'-GGG <u>GGA TCC</u> CAC CAT GAA AGC CCC G-3' (SEQ ID NO:30) containing the underlined BamHI restriction site followed by nucleotides complementary to nt 753–768 shown in FIGS. 1A and B (SEQ. ID NO:1) followed by the Fc immunoglobulin fragment having the following sequence:

5'-G<u>GGATCC</u>GGAGCCCAAATCTTCTGACAAAACTC
ACACATGCCCACCGTGCCCAGCACCTGAATTC
GAGGGTGCACCGTCAGTCTTCCTCTTCCC
CCCAAAACCCAAGGACACCCTCATGATCTCC
CGGACTCCTGAGGTCACATGCGTGGTGGTGGAC
GTAAGCCACGAAGACCCTGAGGTCAAGTTCAA
CTGGTACGTGGACGGCGTGGAGGTGCATAATGC
CAAGACAAAGCCGCGGGAGGAGCAGTACAA
CAGCACGTACCGTGTGGTCAGCGTCCTCACCGT
CCTGCACCAGGACTGGCTGAATGGCAAGGAG
TACAAGTGCAAGGTCTCCAACAAAGCCCTCCCA
ACCCCCATCGAGAAAACCATCTCCAAAGCCAA
AGGGCAGCCCCGAGAACCACAGGTGTACACC
CTGCCCCCATCCCGGGATGAGCTGACCAAGA
ACCAGGTCAGCCTGACCTGCCTGGTCAAAGGC
TTCTATCCAAGCGACATCGCCGTGGAGTGGGAG
AGCAATGGGCAGCCGGAGAACAACTACAAG
ACCACGCCTCCCGTGCTGGACTCCGACGGCTCC
TTCTTCCTCTACAGCAAGCTCACCGTGGACAAG
AGCAGGTGGCAGCAGGGGAACGTCTTCTCAT
GCTCCGTGATGCATGAGGCTCTGCACAACCACT
ACACGCAGAAGAGCCTCTCCCTGTCTCCGGGTA
AATGAGTGCGACGGCCGCGAC<u>TCTAGA</u>GGAT-3'
(SEQ ID NO:31).

The amplified fragment was digested with the endonucleases BamHI and then purified again on a 1% agarose gel. The isolated fragment and the dephosphorylated vector were then ligated with T4 DNA ligase. *E. coli* HB 101 or XL-1 Blue cells were then transformed and bacteria are identified that contain the fragment inserted into plasmid pC4 using, for instance, restriction enzyme analysis.

CHO Cell Transfection:

Chinese hamster ovary (CHO/dhfr-DG44) cells were transfected with the expression vector (pC4/spCKμ8/Fc/AIM II) using lipofectin. Recombinant clones were isolated by growing the cells in MEM alpha selective medium with 5% dialyzed fetal bovine serum (DiFBS), 1% penicillin/streptomycin (PS), 1 mg/mL geneticin (G418) and 10 nM methotrexate (MTX). High expressing clones, which were confirmed by screening recombinant clones using a BIAcore method (see, below for more details), were then individually amplified by increasing stepwise the concentration of MTX to a final concentration of 100μM. The high expressing clones were used for the production of AIM II-IgG1 fusion protein in a microcarrier CHO perfusion bioreactor.

CHO.AIM II-IgG1 cells were grown on Cytodex 1 microcarriers (Pharmacia Biotech, Upsala, Sweden) in HGS-CHO-3 medium containing 1% ultra-low IgG FBS. The cells grown in multiple microcarrier spinners were scaled up to a 10 L microcarrier perfusion bioreactor. The perfusion bioreactor was operated continuously for 27 days and during that period of time, 90 liters of microcarrier-free supernatants containing AIM II-IgG1 fusion protein were harvested. The supernatants were clarified through a filtration process using 0.2 μm sterile filters and stabilized by adding 5 mM EDTA. The clarified supernatants were loaded onto an affinity column to capture AIM II-IgG1 fusion protein.

Purification of AIM Il-IgG1 Fusion Protein

The AIM II-IgG1 fusion protein was purified from 15 L of CHO conditioned media. The conditioned media was loaded onto a Protein A HyperD (54 mL bed volume, BioSepra) affinity column at a flow rate of 30 mL/min at 10° C. on a BioCad 60 (PerSeptives Biosystems). The column was preequilibrated with 25 mM sodium acetate, pH8 and 0.1M NaCl. After loading, the column was washed with 3 column volumes each of 0.1M sodium citrate, pH5 and 0.1M NaCl and 0.1M sodium citrate, pH 2.8 and 0.1M NaCl. The peak fractions containing AIM II-IgG fusion protein were determined by SDS-PAGE analysis and pooled. The identity of the purified protein was confirmed by N-terminal sequence analysis. The final protein yield was about 9 mg/L condition media.

Example 4

AIM II Expression Constructs

Full-length Constructs:

(a) pCMVsport: The eukaryotic expression vector pCMVsport contains nucleotides encoding the AIM-II ORF from Met(1) to Val(240). The plasmid construction strategy is as follows. The AIM II cDNA of the deposited clone is amplified using primers that contain convenient restriction sites. Suitable primers include the following which are used in this example. The 5' primer, containing the underlined SalI site, an AUG start codon, nucleotides 51–69 in the coding region of the AIM II polypeptide (SEQ ID NO:1) and has the following sequence:

5'-GGG GTC GAC GCCATCATG GAG GAG AGT GTC GTA CGG-3' (SEQ ID NO:32).

The 3' primer, containing the underlined NotI site, nucleotides complementary to nucleotides 753–767 in SEQ ID NO:1 and a stop codon and has the following sequence:

5'-GGG GCG GCC GCG CCT TCA CAC CAT GAA AGC CCCG-3' (SEQ ID NO:33).

The PCR amplified DNA fragment is digested with SalI and NotI and then gel purified. The isolated fragment was then ligated into the SalI and NotI digested vector pCMV sport. The ligation mixture is transformed into *E. coli* and the transformed culture is plated on antibiotic media plates which are then incubated to allow growth of the antibiotic resistant colonies. Plasmid DNA is isolated from resistant colonies and examined by restriction analysis and gel sizing for the presence of the AIM II encoding fragment.

For expression of the recombinant AIM II, eukaryotic cells such as COS or CHO are transfected with the expression vector, as described above, using DEAE-DEXTRAN as described above in Example 3. Expression of the AIM II recombinant protein is detected by the methods described above in Example 3.

(b) pG1SamEN: The retroviral expression vector pG1SamEN encodes the AIM-II ORF from Met(1) to Val (240). The pG1 vector is described in Morgan, R. A., et al., *Nucl. Acids Res.* 20(6):1293–1299(1992) and is similar to the LN vector (Miller, A. D. and Rosman, G. J., *Biotechniques* 7:980–990(1989)), but has additional cloning sites. The plasmid construction strategy is as follows. The AIM II cDNA of the deposited clone is amplified using primers that contain convenient restriction sites. Suitable primers include the following which are used in this example. The 5' primer, containing the underlined NotI site, and an AUG start codon, nucleotides 51–69 in the coding region for the AIM II polypeptide (SEQ ID NO:1) has the following sequence:

5'-GGG GCG GCC GCG CCA TCA TOG AGG AGA GTG TCG TAC GG-3' (SEQ ID NO:34).

The 3' primer, containing the underlined SalI site, nucleotides complementary to nucleotides 753–768 in SEQ ID NO:1 and a stop codon has the following sequence:

5'-GGG GTC GAC GCC TTC A CAC CAT GAA AGC CCC G-3' (SEQ ID NO:35).

The PCR amplified DNA fragment is digested with SalI and NotI and then gel purified. The isolated fragment was then ligated into the SalI and NotI digested vector. The ligation mixture is transformed into *E. coli* and the transformed culture is plated on antibiotic media plates which are then incubated to allow growth of the antibiotic resistant colonies. Plasmid DNA is isolated from resistant colonies and examined by restriction analysis and gel sizing for the presence of the AIM II encoding fragment.

For expression of the recombinant AIM II, eukaryotic cells such as COS or CHO are transfected with the expression vector, as described above, using DEAE-DEXTRAN as described above in Example 3. Expression of the AIM II recombinant protein is detected by the methods described above in Example 3.

2. N-terminal Deletion Constructs:

(a) pG1/ckμ8: The eukaryotic expression vector encodes the AIM-II mutant (Gln(60) to Val(240) in SEQ ID NO:2) (AIM-2(aa60–240)) and was secreted under the direction of the human Ck-μ8 signal peptide. The pG1 vector is described in Morgan, R. A., et al., *Nucl. Acids Res.* 20(6):1293–1299(1992) and is similar to the LN vector (Miller, A. D. and Rosman, G. J. *Biotechniques* 7:980–990(1989)), but has additional cloning sites. The plasmid construction strategy is as follows. The AIM II cDNA of the deposited clone is amplified using primers that contain convenient restriction sites. Suitable primers include the following which are used in this example. The 5' primer, containing the underlined NotI site, nucleotides in the coding region for the AIM II polypeptide (SEQ ID NO:1) and an AUG start codon has the following sequence:

5'-GGG GCG GCC GC*G CCA TCA TGA AGG TCT CCG TGG CTG CCC TCT CCT GCC TCA TGC TTG TTA CTG CCC TTG GAT CGC AGG CAG CTG CAC TGG CGT*-3' (NotI+Kozak+CK-β8 leader (double underline)) (SEQ ID NO:36).

The 3' primer, containing the underlined SalI site, nucleotides complementary to nucleotides 753–768 in SEQ ID NO:1 and a stop codon has the following sequence:

5'-GGG GTC GAC TCA CAC CAT GAA AGC CCC G-3' (SEQ ID NO:37).

The PCR amplified DNA fragment is digested with SalI and NotI and then gel purified. The isolated fragment was then ligated into the SalI and NotI digested vector pG1. The ligation mixture is transformed into *E. coli* and the transformed culture is plated on antibiotic media plates which are then incubated to allow growth of the antibiotic resistant colonies. Plasmid DNA is isolated from resistant colonies and examined by restriction analysis and gel sizing for the presence of the AIM II encoding fragment.

For expression of the recombinant AIM II, eukaryotic cells such as COS or CHO are transfected with the expression vector, as described above, using DEAE-DEXTRAN as described above in Example 3. Expression of the AIM II recombinant protein is detected by the methods described above in Example 3.

(b) pHE4: Plasmid pHE4 is a bacterial expression vector containing a strong synthetic promoter with two lac operators. Expression from this promoter is regulated by the presence of a lac repressor, and is induced using IPTG or lactose. The plasmid also contains an efficient ribosomal binding site and a synthetic transcriptional terminator downstream of the AIM II mutant gene. The vector also contains the replication region of pUC plasmids and the kanamycin resistance gene.

The AIM-II N-terminal deletion mutants were constructed according to the following scheme. The AIM II cDNA of the deposited clone is amplified using primers that contain convenient restriction sites. Suitable primers include the following which are used in this example.

For the AIM II (Thr(70) to Val(240)) polypeptide in SEQ ID NO:2, the 5' primer, containing the underlined NdeI site, and an AUG start codon, nucleotides 256–271 in the coding region for the AIM II polypeptide (SEQ ID NO:1) has the following sequence:

5'-cgc <u>CATATG</u> A CCCGCCTGCCTGACG-3' (SEQ ID NO:42).

For the AIM II (Ser(79) to Val(240)) polypeptide in SEQ ID NO:2, the 5' primer, containing the underlined NdeI site, and an AUG start codon, nucleotides 283–310 in the coding region for the AIM II polypeptide (SEQ ID NO:1) has the following sequence:

5'-cgc <u>CATATG</u> A GC TGGGAGCAGCTGATAC-3' (SEQ ID NO:43).

For the AIM II (Ser(103) to Val(240)) polypeptide in SEQ ID NO:2, the 5' primer, containing the underlined NdeI site, and an AUG start codon, nucleotides 355–373 in the coding region for the AIM II polypeptide (SEQ ID NO:1) has the following sequence:

5'-cgc <u>CATATG</u> A GC AGCTTGACCGGCAGCG-3' (SEQ ID NO:44).

The following 3' primers can be used to construct the aforementioned N-terminal deletions:

The 3' primer, containing the underlined Asp718 site, nucleotides complementary to nucleotides 753–768 in SEQ ID NO:1 and a stop codon has the following sequence:

5'-cgc <u>GGTACC</u> TTA CACCATGAAAGCCCCG-3' (SEQ ID NO:45).

The PCR amplified DNA fragment is digested with NdeI and Asp718 and then gel purified. The isolated fragment was then ligated into the appropriately digested pHE4 vector. The ligation mixture is transformed into *E. coli* and the transformed culture is plated on antibiotic media plates which are then incubated to allow growth of the antibiotic resistant colonies. Plasmid DNA is isolated from resistant colonies and examined by restriction analysis and gel sizing for the presence of the AIM II encoding fragment.

For expression of the recombinant AIM II N-terminal deletion, bacterial cells are transfected with the expression vector, as described above in Example 1. Expression of the AIM II recombinant protein is detected by the methods described above in Example 1.

Example 5

Biological Characterization of the AIM II Polypeptide

The following set of experiments provides the biological characterization of the AIM II protein and demonstrates that AIM II has potent anti-tumor activity in vivo and in vitro.

A. AIM II is Highly Expressed in Activated Lymphocytes but not in Cancer Cells

Northern blot analyses demonstrated that the AIM II mRNA is approximately 1.9 kb in length and is expressed predominantly in spleen, brain and peripheral blood cells. AIM II is also detectable to some extent in prostate, testis, ovary, small intestine, placenta, liver, skeletal muscle and lung. AIM II message was not detected in fet al tissues, many endocrine glands and tumor lines of non-hematopoietic and myeloid origin.

RT-PCR assays were performed to investigate expression of AIM II in activated vs. resting PBMC. Fresh PBMC including mixture of T cells, B lymphocytes, NK cells, monocytes and granulocytes express the AIM II mRNA which is consistent with Northern blot analysis. No expression was found in resting PBLs as mixture of T, B and NK cells, Jurkat cells (resting or activated) or K562 cells. Increased expression of AIM II was found in activated PBLs, CD3+, CD4+T-cells, CD8+ Tumor infiltrating lymphocytes (TIL), granulocytes, and monocytes. Additional RT-PCR analyses demonstrated the presence of AIM II mRNA in LPS-activated neutrophils and PMA-stimulated U937 cells. Interestingly, expression of AIM II was not detectable in various cancer cell lines derived from breast, prostate or ovary, except in one human breast epithelial-derived, non-tumorigenic cell line MCA-1OA cells. In addition, no expression of AIM II was found from three breast cancer samples examined.

B. Constitutive Expression of AIM II Resulted in Growth Inhibition Under Serum Starvation or Treatment with IFNγ

To investigate the biological function of AIM II, the AIM II gene was stably transduced into human breast carcinoma cell line MDA-MB-231 using a retroviral vector. Expression of the AIM II gene in these cells was confirmed by Northern blot analyses. In addition, MDA-MB-231 cells expressing the drug resistance gene Neo were used as control in this study. No difference in the growth rate in vitro was observed within AIM II transfectants (MDA-MB-231/AIM II) compared with that of the parental cells or vector control transfected cells (MDA-MB-231/Neo), when these cells were cultured inmedium containing 10% FBS. However, when the serum concentration was reduced to 1%, there was 80% growth inhibition (FIG. 4A) for the MDA-MB-231/AIM II cells, but not for the parental or vector control MDA-MB-231 cells. A dose-dependent growth inhibition with a different amount of serum has also been observed.

Figure 4A:
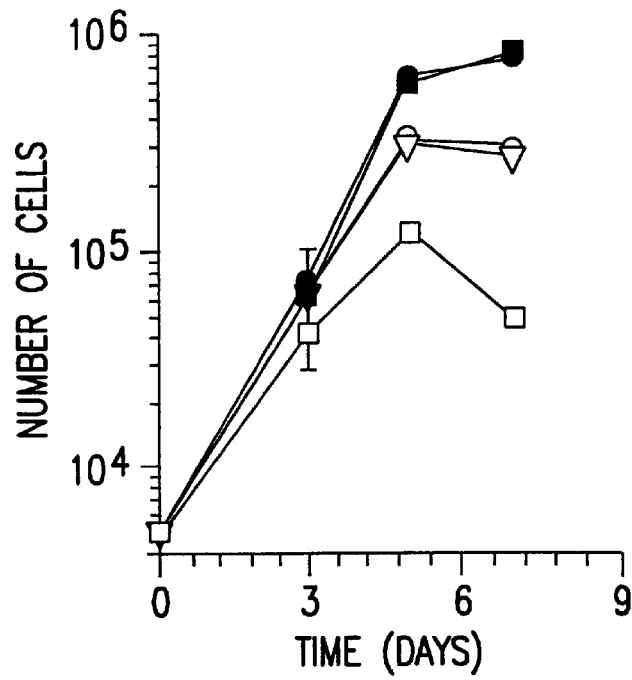
FIGS. 4A and B show the effect of AIM II on the in vitro proliferation of MDA-MB-231 human breast cancer cells. 5,000 MDA-MB-231/WT (circle), MDA-MB-231/Neo (triangle) or MDA-MB-231/AIM II (square) cells were plated in triplicate in 24-well plates with IMEM in the presence of either 10% FBS (filled circle, square or triangle) or 1% FBS (open circle, square or triangle). The number of live cells were determined by trypan blue exclusion method at day 3, day 5 or day 7. Cells were fed with fresh medium every two days during this time course.
Figure 4B:
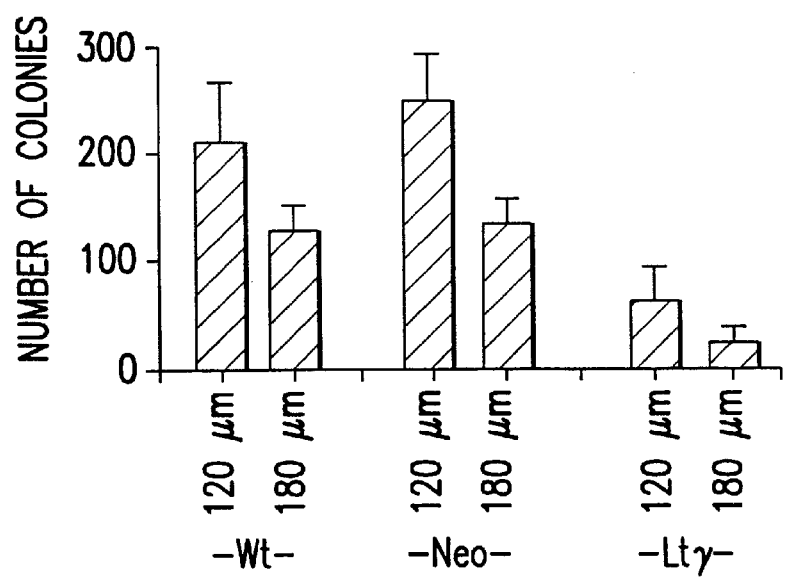
FIG. 4B shows colony formation of MDA-MB-231/WT, MDA-MB-231/Neo and MDA-MB-231/AIM II cells in 0.33% agarose.

Wild type MDA-MB-231 cells grew to a very high density with typical pile-up features in either 10% or 1% serum (FIG. 4A). Morphological changes were noticed in the MDA-MB-231/AIM II cells, with most cells floating into the medium and keeping a single layer growth pattern throughout the culture. No changes of morphology were found in the vector control MDA-MB-231 cells. Growth inhibition of AIM II expressing MDA-MB-231 cells was further examined with in soft agar colony assay. As shown in FIG. 4B, 80% reduction of colony formation was found in the MDA-MB-231/AIM II cells as compared with that of the parental or vector control cells. Treatment with 25 u/ml of IFNγ can also cause 80% growth inhibition of AIM II expressing MDA-MB-231 cells, whereas in the parental or vector control cells, there is only 20–30% inhibition. Thus, AIM II expressing cells demonstrated enhanced sensitivity towards cytotoxicity mediated by cytokine IFNγ.

C. Enhanced Apoptosis in AIM II Expressing Cells.

Figure 5A:
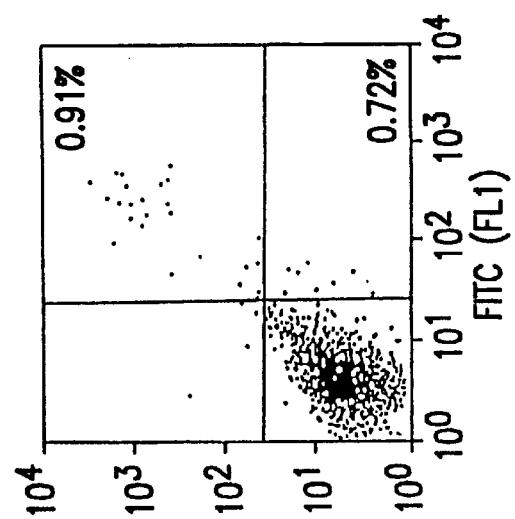
FIGS. 5A–C show increased Apoptotic cells in MDA-MB-231/AIM II (FIG. 5C) in 0.5% serum compared with that of the MDA-MB-231/WT (FIG. 5A) or MDA-MB-231/Neo (FIG. 5B) cells with Annexin-V FACS analysis as described in Example 5 Material and Methods.
Figure 5B:
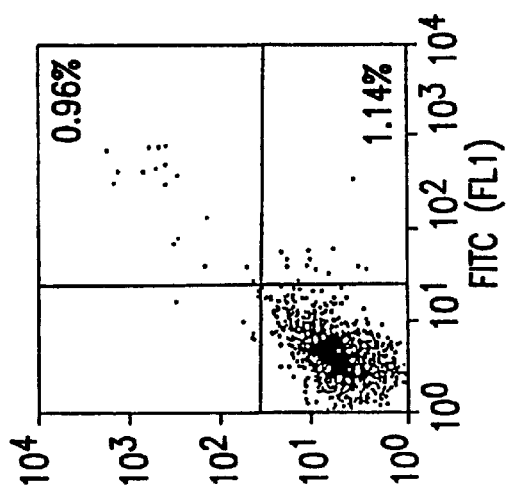
Figure 5C:
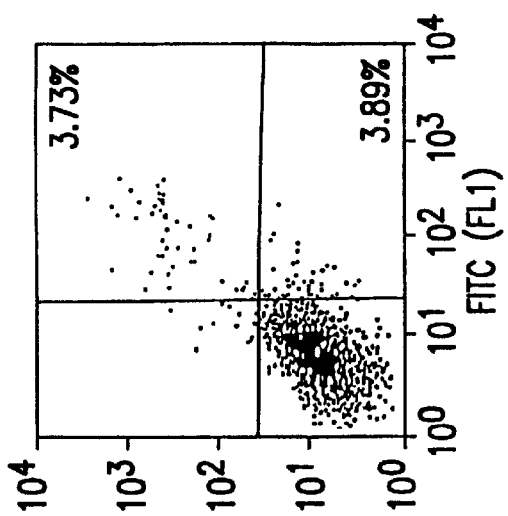

Annexin-V FACS analyses were performed to investigate underlying mechanisms of growth inhibition of AIM II expressing cells. In the presence of 10% serum, there are less than 2% apoptotic cells in all three cell lines. After 48 hours incubation in reduced serum (0.5% FBS), the apoptotic population of the MDA-MB-231 cells showed a three-fold increase, up to 8%. There is little or no increase of apoptosis in the parental or vector control MDA-MB-231 cells (FIGS. 5A–C). Induction of apoptosis was further confirmed by a DNA fragmentation assay of MDA-MB-231/WT, MDA-MB-231/Neo and MDA-MB-231/AIM II cells in 10% and 0.5% serum, with or without Paclitaxel (taxol). Fragmented DNA was only seen in the AIM II expressing MDA-MB231 cells, especially in 1% serum. When AIM II expressing cells were treated with Paclitaxel (taxol), there was much more fragmented DNA observed than seen in parental or vector control cells. Thus, the data suggest that AIM II expression can trigger apoptosis of MDA-MB-231 cells under serum starvation or with the addition of IFNγ or taxol.

D. Potent in vivo Anti-tumor Activities of AIM II.

Figure 6A:
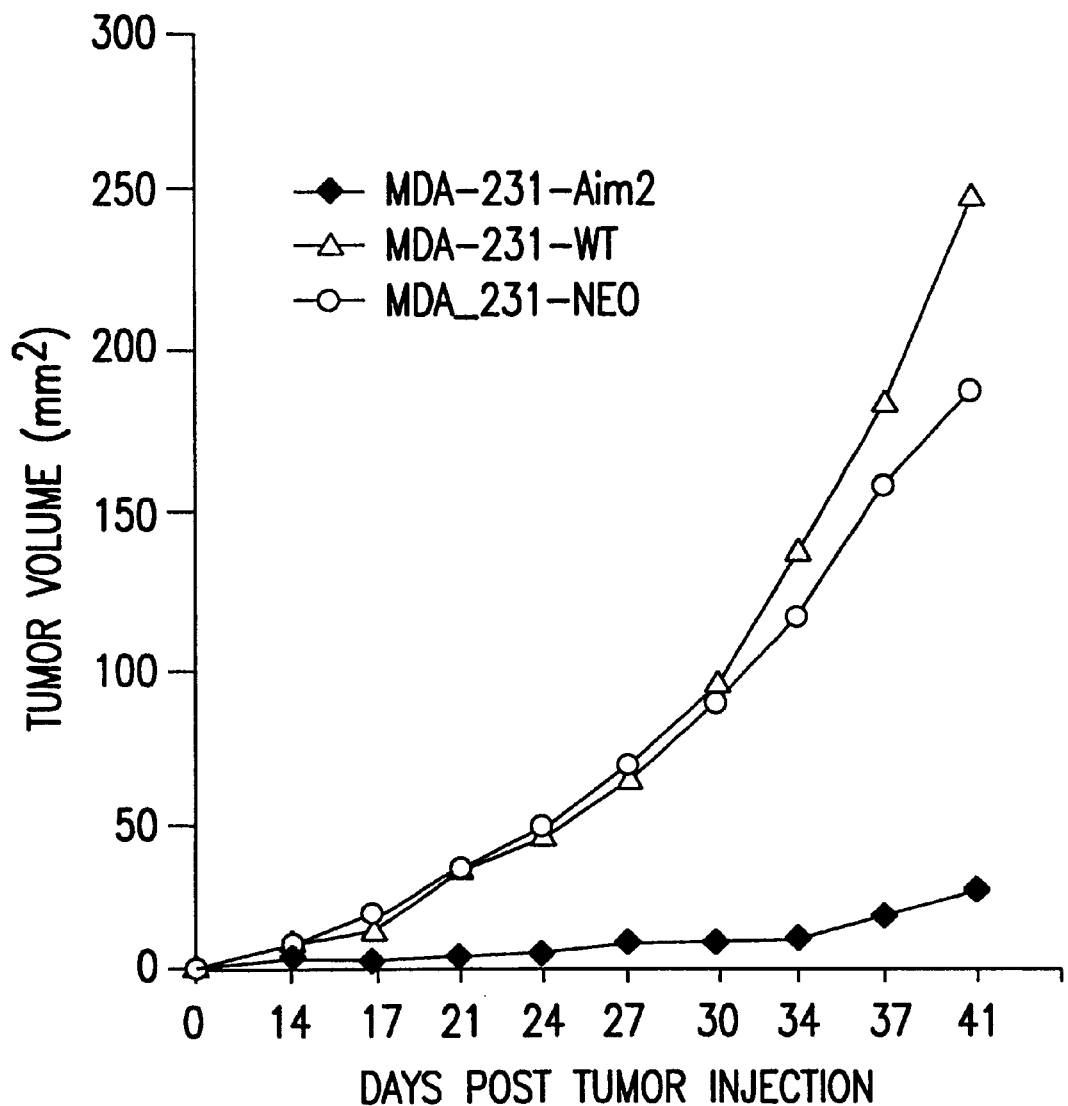
FIG. 6(A) shows an evaluation of the effects of AIM II on growth of xenograft human breast carcinoma MDA-231 in nude mice. Female athymic nude mice were injected s.c. with $10^6$ cells of parental MDA-23 1 (MDA-23 1-WT), or MDA-23 1 stably transfected with AIM II, or vector control neo (n=10). Mice were then ear tagged and randomized. Tumor growth was assessed twice weekly with a caliper in the blinded fashion. This panel represents three experiments each with ten mice per group. (B) shows the effect of AIM II transduction on inhibition of growth of MC-38 murine colon cancer in syngeneic C57BL/6 mice. Female C57BL/6 mice were injected s.c. with $10^6$ cells of parental MC-38 (MC38-WT), or MC-38 stably transfected with AIM II, or vector control neo (n=10). Mice were then ear tagged and randomized. Tumor growth was assessed twice weekly with a caliper in a coded, blinded fashion. This panel represents four experiments each with ten mice per group.

We have evaluated the effects of AIM II transduction on the tumor growth in vivo. When MDA-MB-231 cells were inoculated into the mammary fat pads, AIM II expression significantly inhibited tumor formation of MDA-MB-231 in nude mice, whereas the vector control MDA-MB-231/Neo cells showed no change in tumor growth as compared with that of the parental MDA-MB-231 cells (FIG. 6A). Similar tumor suppression in the MDA-MB-231/AIM II cells was also demonstrated in SCID mice. A histological examination of the tumors from AIM II expressing MDA-MB-231 cells or those from parental or vector control cells was performed. Parental or vector control MDA-MB-231 cells formed a large solid tumor mass filled with predominantly tumor cells with little or no cellular infiltrates. In contrast, there was extensive necrosis observed even in small residual tumors formed by the MDA-MB-231/AIM II cells in nude mice. Furthermore, in AIM II expressing tumors, there is an significant increase in number of infiltrating neutrophil cells. The average number of neutrophils (mean +S. D.) per mm$^2$ tumor size in wild type, Neo control, and AIM II transduced MDA-MB-231 tumors were 101+26, 77+16 and 226+38, respectively, based on the immunohistological staining using Gr-1 mAb (PharMingen, San Diego, Calif.).

Figure 6B:
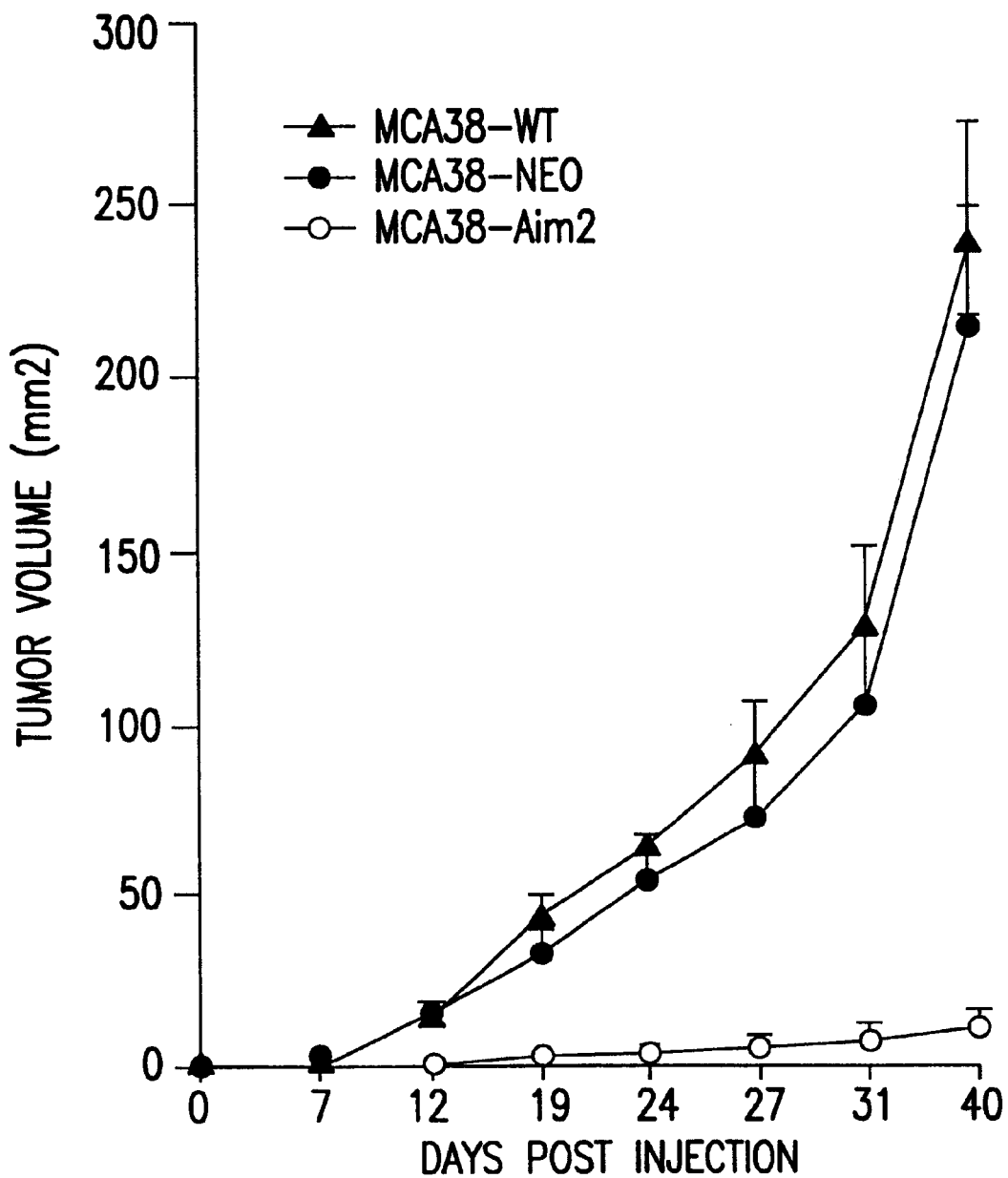

The inhibitory effect of AIM II on tumor suppression was further validated in the syngeneic murine tumor model. Local expression of AIM II in MC-38 murine colon cancer cells resulted in complete suppression of tumor formation in 8 out of 10 C57BL/6 mice (FIG. 6B). Local production of AIM II was also dramatically prolonged the survival of mice bearing MC-38 tumors. All animal experiments were repeated three times and similar results were obtained.

Injection of AIM II-expressing tumor cells did not cause gross abnormalities in the nude mice, SCID mice or C57BL/6 mice, such as weight loss or hepatic injury, during the experimental period. This indicates that locally produced AIM II exerts a potent anti-tumor effect without inducing systemic toxicity.

E. Expression and Cytotoxicity of a Soluble AIM II Protein

Figure 7A:
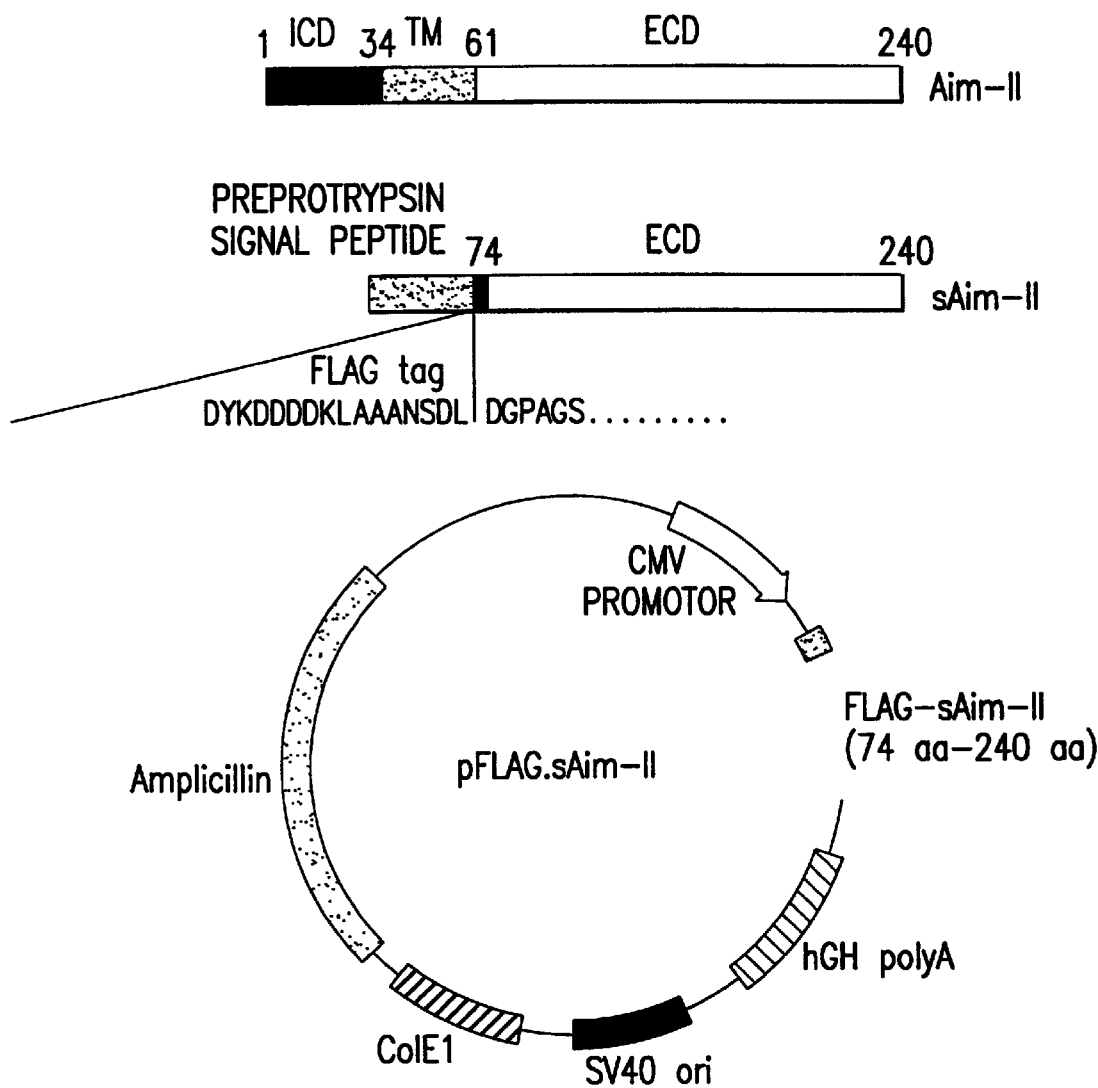
FIG. 7A–C shows the pFlag-AIM II plasmid construct (FIG. 7A), the FLAG tag (SEQ ID NO:57) fused to amino acids 74 to 79 of SEQ ID NO:2, and the polypeptide purified from the conditioned medium of pFlag-AIM II transduced 293 T cells. Cytotoxicity of a recombinant soluble form of AIM II (sAIM II) in MDA-MB-231 cells in the presence or absence of IFNγ (FIG. 7B) or with IFNγ alone (FIG. 7C). Experiments were carried out as described in Example 5 Materials and Methods.
Figure 7B:
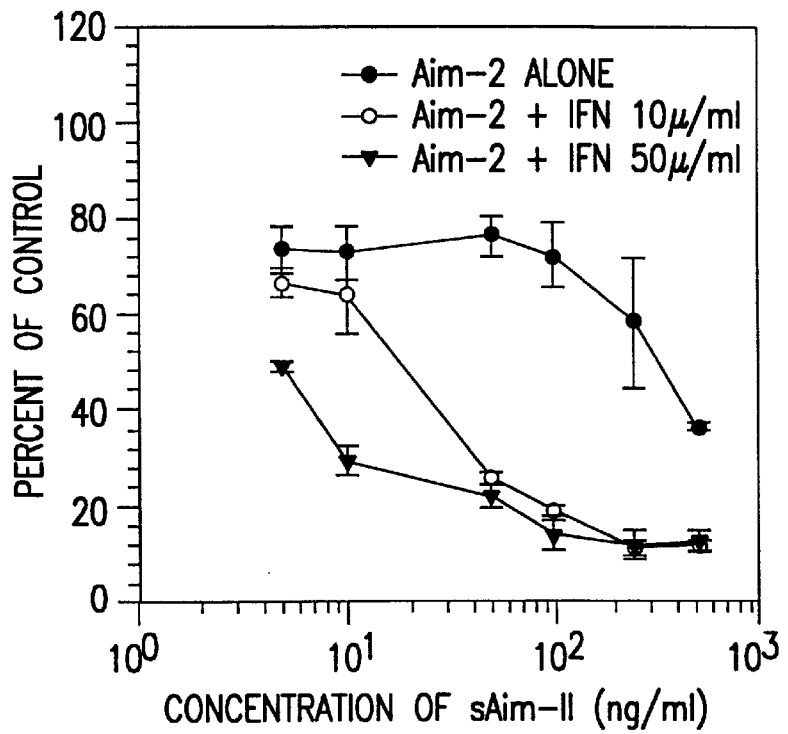
Figure 7C:
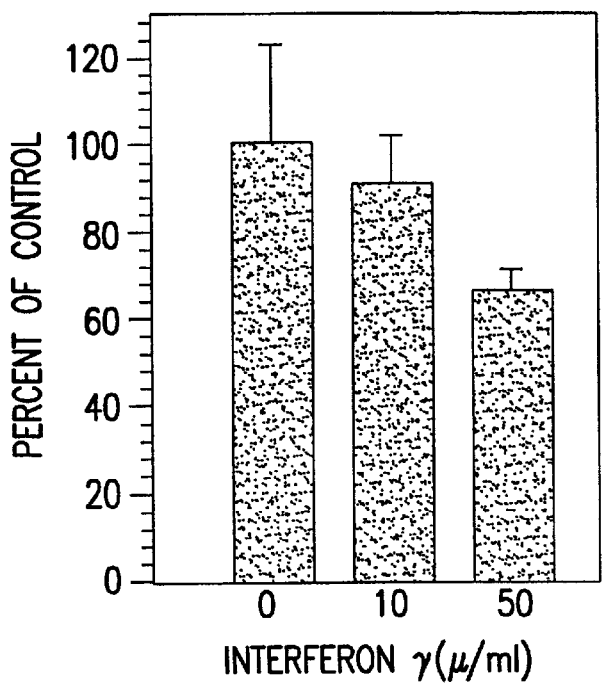

In order to study the activities of the AIM II protein, a recombinant soluble form of AIM II protein (sAIM II) was produced by transient transfecting 293T cells with a construct pFlag-AIM II. This construct encodes the extracellular domain of AIM II, but lacking the transmembrane portion of AIM II. The construct is shown in FIG. 7A. A single 20 kDa polypeptide (sAIM II) can be purified from the conditioned medium of pFlag-AIM II transduced 293T cells with anti-Flag monoclonal antibody. The proliferation of breast cancer MDA-MB-231 cells were inhibited in response to the treatment of this soluble AIM II protein, at a dose dependent manner (FIGS. 7B and 7C). Addition of IFNγ, at 10 u/ml or 50 u/ml, dramatically enhanced cytotoxicity of the soluble AIM II protein. IFNγ alone showed little activity on the MDA-MB-231 cells (FIGS. 7B and 7C). This is consistent with previous report that MDA-MB-231 cells is resistant to single cytokine such as TNF or IFNγ treatment.

A series of normal and cancer cell lines were tested for their sensitivity to the cytotoxic effects of soluble AIM II protein at sub-optimal concentration (50 ng/ml) in the presence of 10 u/ml of INFγ. As shown in FIG. 8L, cells from MDA-130, MCF-7, HT-29 are sensitive to the cytotoxic effects of AIM II, whereas cells from U93T, MC3-1, SW480, MCF-10A are resistant to AIM II mediated cell killing. Among all the cell lines tested, colon adenocarcinoma cell line HT-29 is the most sensitive, with IC$_{50}$ less than 1 ng/ml. It has been shown that HT-29 is very sensitive to TNF, Fas or lymphotoxin β receptor mediated killing in the presence of IFNγ.

F. Both LTβR and TR2 are Required for AIM II Induced Growth Inhibition of Cancer Cells.

AIM II was originally identified from an activated T-cell cDNA library but does not induce apoptosis in lymphocyte cell lines. Using the RT-PCR analyses, all lymphopoietic cells examined showed no expression of LTβR, but TR2 expression was found in all these cells, especially in activated Jurkat cells or PBLs. This is consistent with the previous reports that peripheral lymphocytes do not express the LTβR, while TR2 expression is associated with T-cell activation.

Figure 8A:
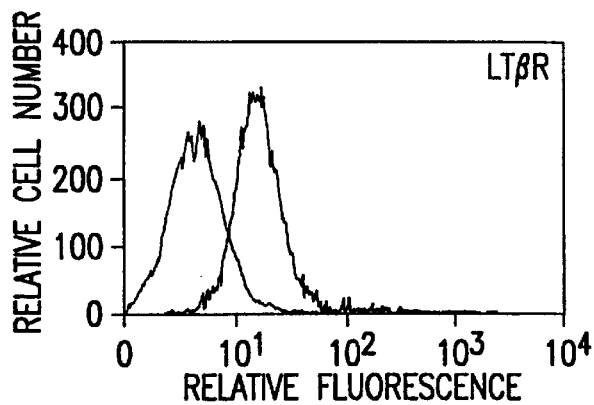
FIGS. 8A through 8H show cell surface expression of the LTβR or TR2 by the FACS analyses using LTβR (FIGS. 8A–D) or TR2(FIGS. 8E–H) mAb. MDA-MB-231(FIGS. 8A and 8E)), HT-29 (FIGS. 8B and 8F), MC-3(FIGS. 8C and 8G), and U93T (FIGS. 8D and 8H).
Figure 8B:
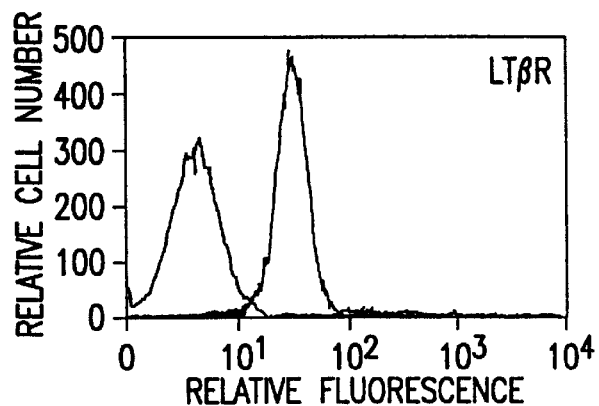
Figure 8C:
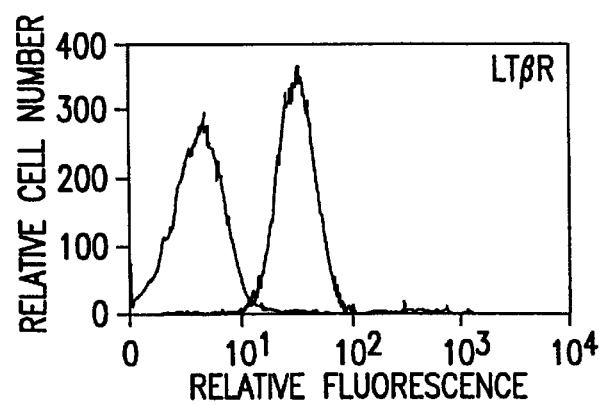
Figure 8D:
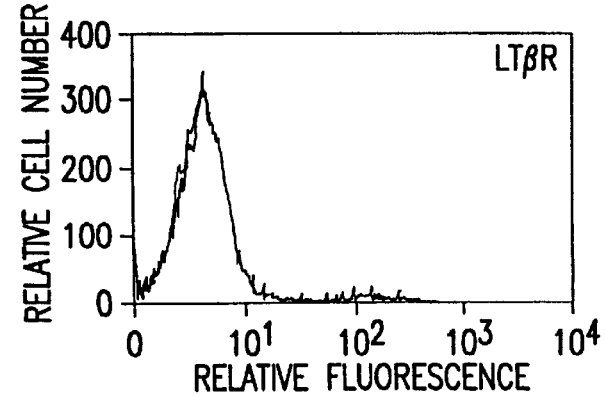
Figure 8E:
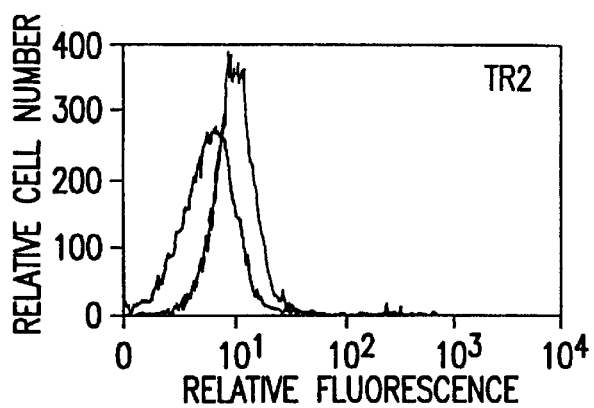
Figure 8F:
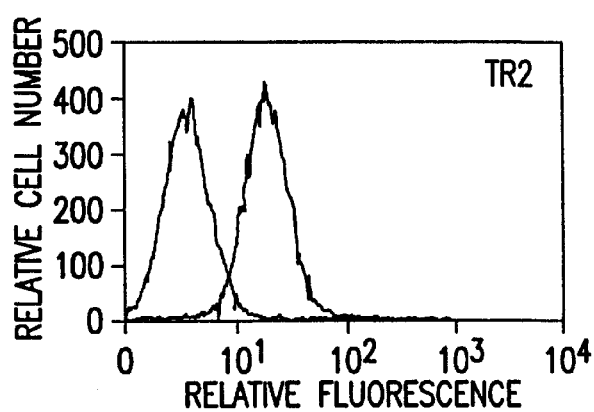
Figure 8G:
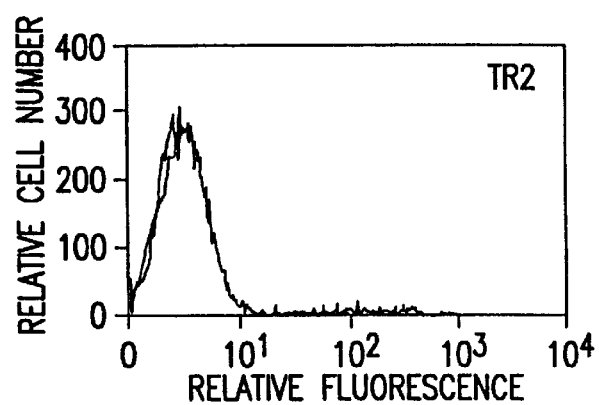
Figure 8H:
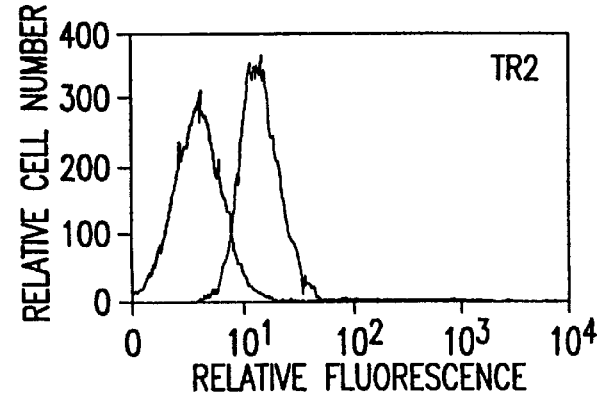

Cell surface expression of the LTβR and TR2 in a series of human cancer cells was examined using monoclonal antibodies against the LTβR or TR2 by FACS analysis. As shown in FIGS. 8A through 8H, high levels of both receptors were found on the MDA-MB-231, and HT-29 cells, whereas MC3-1 cells do not express TR2 and Jurkat cells do not express LTβR. FIG. 8L summarizes surface expression of both receptors in all the cell lines examined. Cell lines that express only one of the receptors, such as Jurkat or MC3-1 are resistant to the cytotoxicity of AIM II. Taken together, these data suggest that AIM 11-mediated growth inhibition in tumor cells may require both LTβR and TR2 receptors, while cells expressing only one of the receptors is not sufficient to mediate cell killing.

Figure 8I:
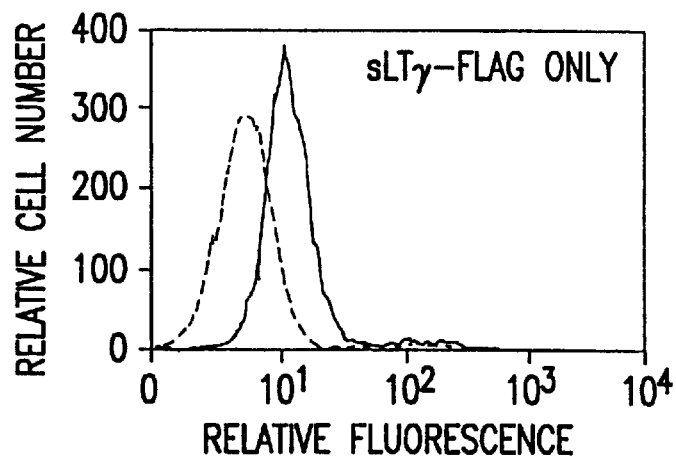
FIGS. 8I through 8J show FACS binding analyses of soluble AIM II protein alone (FIG. 8I) and blocking of a soluble AIM II protein binding by preincubation with the LTβR-Fc fusion protein (FIG. 8J) or TR2-Fc fusion protein (FIG. 8K) in MDA-MB-231 cells.
Figure 8J:
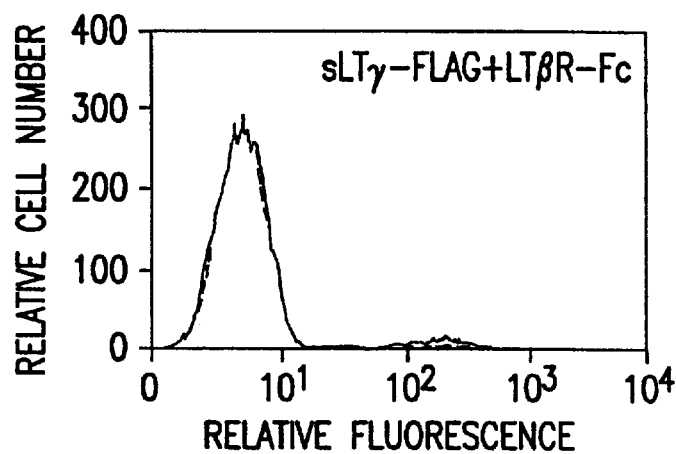
Figure 8K:
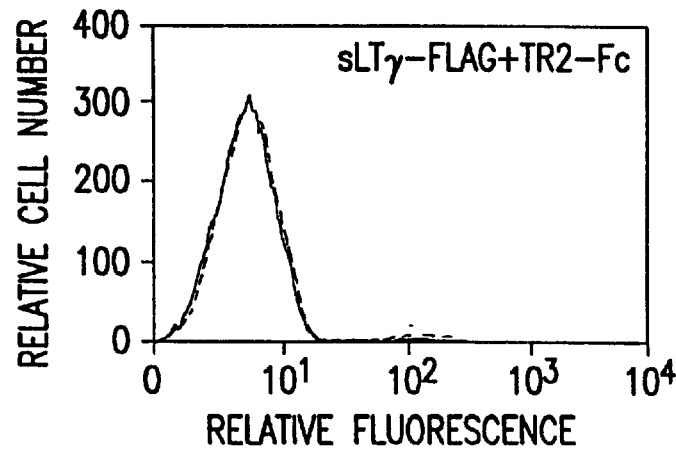
FIG. 8L summarizes the surface expression of LTβR and TR2 in various cell lines.
FIG. 8M shows the effects of LTβR-Fc or TR2-Fc fusion protein to block the sAIM II-mediated cytotoxicity in HT-29 cells. Cells were plated into 96-well plates and sAIM II (10 ng/ml) was added in the presence of 5 U/ml of IFNγ with various amounts of sLTβR-Fc (open circle with LTβR-Fc alone, filled circle LTβR-Fc, and IFNγ) or TR2-Fc fusion protein (open triangle with TR-2Fc alone, filled triangle TR2-Fc with sLTγ and IFNγ). Cells were incubated for five days and the viability of cells was determined by XTT assays.

To further demonstrate that the AIM II is a relevant ligand for both LTβR and TR2 receptors and the importance of both receptors in AIM II mediated tumor cell growth inhibition, the Flag-tagged AIM II protein was incubated with MDA-MB-231 or HT-29 cells, then FACS analyses were carried out using anti-Flag mAb. As shown in FIGS. 8I through 8K, there is a positive shift in binding of MDA-MB-231 or HT-29 cells with Flag-tagged soluble AIM II protein. The specificity of binding was further confirmed by preincubation of LTβR-Fc or TR2-Fc fusion protein with a soluble AIM II-flag protein in the same cells, which effectively blocked binding of both receptors (FIGS. 8I through 8K).

Figure 8M:
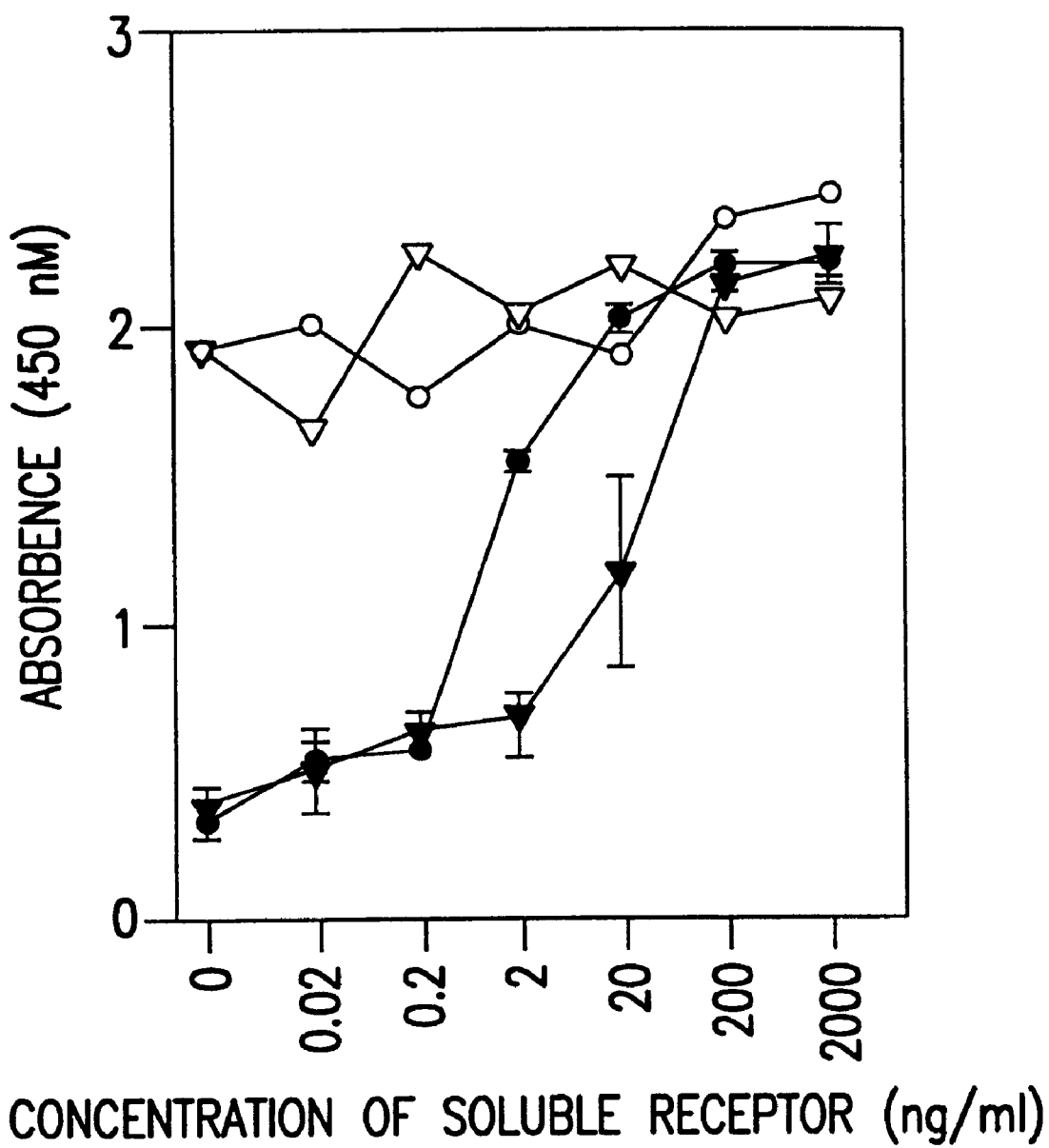

The importance of the involvement of both LTβR and TR2 in the AIM II-mediated cytotoxicity toward tumor cells was further supported by the data obtained from the in vitro growth assays: sAIM II-mediated cytotoxicity of HT-29 was abolished by the addition of LTβR-Fc or TR2-Fc fusion protein in a dose-depended manner whereas the LTβR-Fc or TR2-Fc fusion protein itself showed no effect on cell growth (FIG. 8M). In addition, in a similar assay, sAIM II was unable to bind to other members of TNFR, such as TNFRI, Fas, DR3 or DR14.

In addition, co-culture of MDA-MB-231/Wt or HT-29 cells with MDA-MB-231/AIM II cells resulted in killing of the MDA-MB-231/Wt or wild type HT-29 cells. However, conditioned media collected from the co-cultured MDA-MB-231/AIM II or MC-38/AIM II cells showed no inhibitory effect on the in vitro proliferation of HT-29 cells. The results indicated that the natural AIM II protein may not be cleaved and secreted into the medium. Thus, the membrane-bound AIM II is functional in cells which express appropriate surface receptors such as MDA-MB-231 or HT-29. Taken together, this data suggests that the AIM II-mediated growth inhibition of tumor cells may require both LTβR and TR2 receptors, while cells expressing only one of the receptors is not sufficient to mediate cell killing.

G. Effects of AIM II on the Lymphocytes

AIM II was originally identified from an activated T-cell cDNA library but does not induce apoptosis in lymphocyte cell lines. Using RT-PCR analyses, all lymphopoietic cells examined showed no expression of LTβR, but TR2 was positive in all these cells, especially in activated Jurkat cells or PBLs. This is consistent with previous reports that peripheral lymphocytes do not express the LTβR, while TR2 expression was associated with T-cell activation.

To investigate whether the membrane-bound AIM II exerts different activities on the lymphocytes, co-culture experiments of TIL1200 cells with MDA-MB-231/AIM II cells was carried out. TIL1200 is a CD8$^+$(995) tumor infiltrating lymphocyte line expressing a high level of Fas. The membrane-bound AIM II did not induce apoptosis of TIL1200, whereas the addition of Fas antibody triggered 90% of TIL1200 undergone apoptosis. Similar results were obtained with fresh TIL cells or Jurkat cells.

Figure 9:
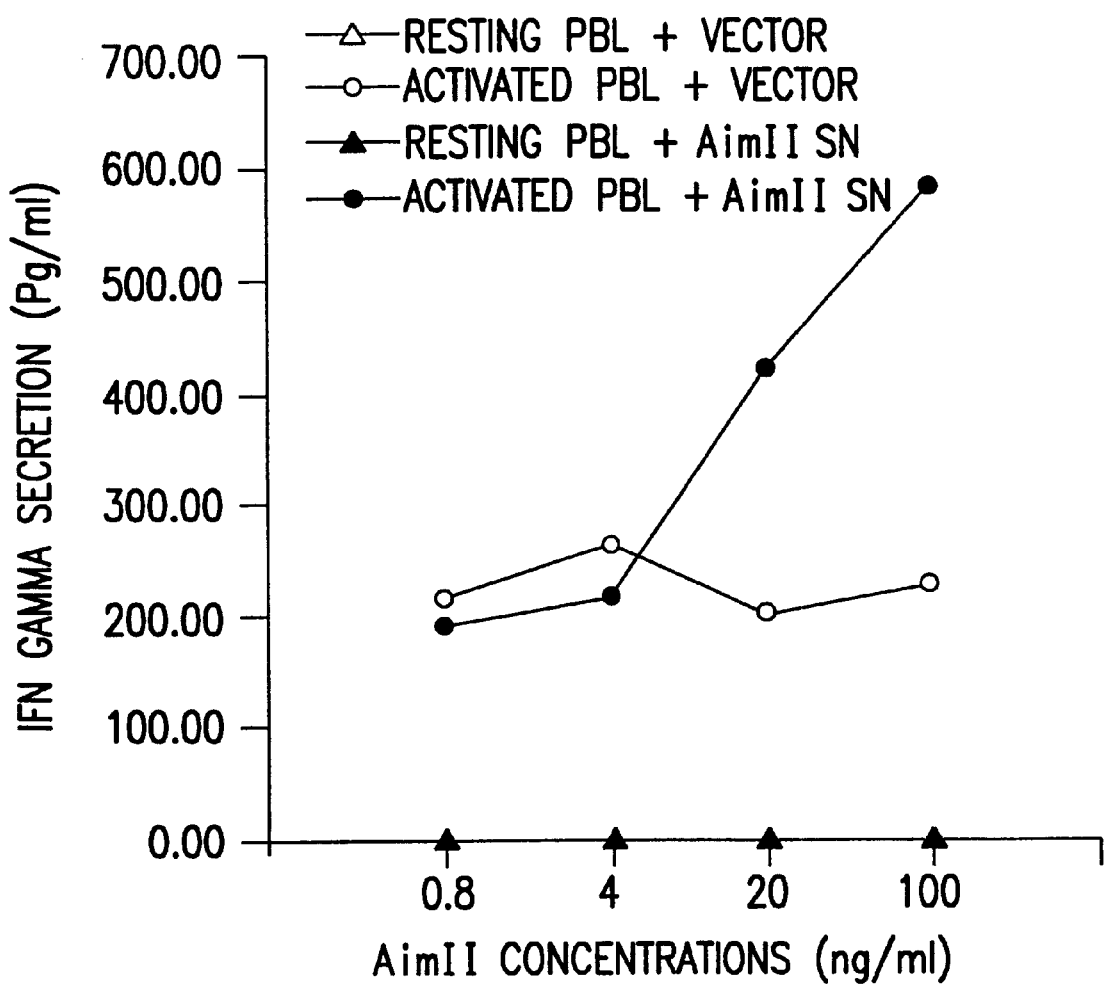
FIG. 9 shows secretion of IFN-γ by sAIM II treated human PBL cells. Human PBLs (5×$10^5$ cells per well in the 96 well plate) were treated with or without anti-CD3 mAb and IL-2(20 U/ml) in the presence or absent of sAIM II for 5 days. The supernatants were then collected from the following groups of cells: PBLs in the presence (filled circle) or absence (open circle) or sAIM II, or the resting PBLs with (filled triangle) or without (open triangle) sAIM II. Human IFNγ concentration were determined by ELISA.

Furthermore, several lymphoid cell lines and PBLs were screened for their responsiveness to the soluble AIM II protein. No cytotoxicity of AIM II was shown in Jurkat cells (either resting or CD3 mAb activated), K562 cells, or TIL1200 (tumor infiltrating lymphocytes), PBMC (fresh or IL-2/CD3 mAb activated) (FIG. 8L). In contrast, treatment of PBLs with sAIM II, resulted in activation of TR2 expressing T cells as demonstrated by release of IFNγ (FIG. 9).

Discussion

In the foregoing experiments, the biological functions of AIM II and its possible mechanisms of action as a novel ligands of LTβR and TR2 have been characterized. The results demonstrate that the AIM II protein exhibits potent cytotoxicity primarily in transformed tumor cells both in vitro and in vivo, while at the same time, activating lymphocytes. The biological activities of AIM II in vitro and in vivo clearly distinguish AIM II from other known members of the TNF/FasL family in several ways including binding to two distinct signaling pathways: LTβR and TR2. Since the ability of AIM II expression to inhibit tumor growth was demonstrated in both xenographic (immunodeficient) and syngeneic (immunocompetent) models, the results suggest that the T-cell mediated tumor specific response may not be an essential factor for the primary tumor rejection in this study.

Activation of the TNF receptors family can directly induce cell proliferation, or differentiation or death. The foregoing experiments show that AIM II expression resulted in growth inhibition and apoptosis in the human breast carcinoma cell line MDA-MB-231 in conjunction with serum starvation, or addition of IFNγ. Induction of apoptosis appears to be the primary cause for the growth inhibition in vitro as shown in Annexin-V FACS analysis and DNA fragmentation. The morphology and growth pattern of MDA-MB-231/LT-γ cells suggest involvement of some loss of cells adhesion. Browning et al. have shown that Fas activation led to rapid cell death (12–24 h), TNF effects requires 24 h and LTcx102 heterotrimers were slowest (2–3 days) in induction of apoptosis for HT29 cells. Lysis of the LTγR and TR2 expressing MDA-MB-231 and HT-29 cells in response to the treatment with the soluble AIM II protein showed similar slow effect, i.e. at least 3–5 days. Substantial cell lysis does not occur even after 3–4 days for some cell lines. The dynamics of action of AIM II are more similar to LTα1β2 heterotrimers.

AIM II was originally identified from a human activated T cell library by screening of sequence homology with cysteine-rich motif of the TNF/Fas ligand and receptor superfamily. Like other TNF-related ligands, AIM II is a type-II transmembrane protein with C-terminus on the exterior cell surface, a single transmembrane domain, and a short cytoplasmic tail. As predicted, transduction of a full-length cDNA of AIM II gene resulted in cell surface expression of a protein which binds to two receptors as demonstrated in FACS analyses. A soluble AIM II protein is sufficient to bind to both receptors and trigger cytotoxic effects on the target cells. However in the transwell co-culture experiment, where two type of cells shared the culture medium but are physically separated, cytotoxicity from the AIM II expressing MDA-MB-231 cells towards the wild type MDA-MB-231 or HT-29 cells was not observed. In the direct co-culture assay, membrane-bound AIM II effectively mediated killing from close contact. Thus, it seems that natural AIM II protein may not be a secreted protein. Fluorescence in situ hybridization (FISH) localized AIM II gene to human chromosome 16, band p11.2. The AIM II position is in close proximity with Core binding protein, sulfotransferase, syntaxin 1B, retinoblastoma-binding protein 6, zinc finger protein 44, cell adhesion regulator and Wilms tumor-3 gene. Genes encoding other known TNF ligands such as TNF, LTα, and LTβ are tightly linked on human chromosome 6 within the major histocompatibility complex (MHC) sandwiched between the class lil and HLA-B locus.

Both LTβR and TR2 lack the death domain. Thus, the demonstration of AIM II binding to both LTβR and TR2 is intriguing. Although LTβR and TR2 could activate common signaling pathways via association with TNFR-associated factors (TRAFs), AIM II-LTβR and AIM II-TR2 interactions may trigger the distinct biological events. As shown in this Example, expression of AIM II leads to the death of cells expressing both LTβR and TR2 while activate lymphocytes which expressing only the TR2 receptor. Signaling through the LTβR activates a TRAF3-dependent pathway. In contrast, AIM II-TR2 interaction probably elicits stimulatory responses of host immune system through TRAFs (TRAF 1, TRAF2, TRAF3 and TRAF5). This AIM II dual signaling hypothesis is further supported by the distinct tissue and cell expression patterns of LTβR and TR2. LTβR is prominent in tumor and other epithelial cells, but is absent on the T and B cells. In contrast, TR2 is abundantly expressed in comparable levels in resting and activated T cells, B cells and monocytes and granulocyte. Hence, AIM II probably plays critical roles such as induction of apoptosis and immune activation and, therefore, may have an therapeutic application for cancer.

The LTβR was originally described as a transcribed sequence encoded on human chromosome 12p, a member of the TNFR superfamily. The LTβR is implicated as a critical element in controlling lymph node development and cellular immune reactions. It has been showed that LTβR is expressed in a variety of tissues and cell lines including tumor lines. Unlike other members of the TNFR family, LTβR is not expressed by T nor B lymphocytes. Activation of LTβR by using recombinant LTα1β2 heterotrimers or by cross-linking with immobilized antibodies, induces the death of adenocarcinoma cell lines and production of chemokine IL-8 and RANTES, even though LTβR does not contain the death domain in its cytoplasmic region.

TR2 is expressed in multiple human tissues and shows a constitutive and relatively high expression in hemopoietic lineage cells including resting and activated CD4+ and CD8+ T cells, B cells, monocytes and neutrophils. The TR2 cytoplasmic tail does not contain the death domain seen in the Fas and TNFR-I intracellular domains, and appears to be more related to those of CD40 and 4–1BB. Signals through 4–1 BB and CD40 have been shown to be co-stimulatory to T cells and B cells, respectively. A TR2-Fc fusion protein inhibited a mixed lymphocyte reaction-mediated proliferation, in contrast to FasL and TNF, which trigger apoptosis. All the hemopoietic derived cells tested expresses the TR2 receptor but are resistant to AIM II mediated killing observed in the tumor cells. This indicates that TR2 alone does not mediate death signal. However, since all cancer cells examined expressed both LTβR and TR2, it remains to be elucidated whether both AIM II-LTβR and AIM II-TR2 signaling contributes equally for the AIM II mediated cytotoxicity in tumor cells. We also can not exclude the possibility that AIM II interacts with other known or unknown death receptors such as DR3, DR4 and DR5, although soluble AIM II does not bind to DR3, DR4 and DR5 in an in vitro binding assay.

The dose-limiting toxicity of TNF and cytotoxicity of FasL for T-cells limits their clinical application. Treatment with AIM II could be alternatively attractive approach since AIM II trigger the stimulatory signal rather than the death signal to the host immune cells which expressing the TR2 but lacking the LTβR. AIM II has the ability to selectively induce death of tumor cells probably through LTβR and TR2 and at the same time can trigger secretion of IFNγ from lymphocytes apparently through the TR2 signaling pathway. This model thus demonstrates that AIM II is not only an attractive candidate for the future development an anti-cancer agent, but more importantly, it provides an novel system, distinct from the previously defined TNF or Fas system, for the further understanding of the signaling pathway of members of TNF ligand-receptor interactions.

Methods

Molecular Cloning of AIM II Full Length Gene.

A database containing more than one million ESTs (expression sequence tags) obtained from over 500 different cDNA libraries has been generated through the combined efforts of Human Genome Science Inc. and The Institute for Genomic Research using high throughput automated DNA sequence analysis of randomly selected human cDNA clones. Sequence homology comparisons of each EST were performed against the GenBank database using the blastn and blastn algorithms, ESTs having homology to previously identified sequences (probability equal or less than 0.01) were given a tentative name based on the name of the sequence to which it was homologous. A specific homology and motif search using the conserved amino acid sequence, GLYLIYSQVLF (SEQ ID NO:46), of the TNF/Fas ligand family against this human EST database revealed several EST having>50% homology. One clone containing GYYY-IYSKVQL (SEQ ID NO:47) from human activated T cell library was selected. This EST was sequenced on both strands to the 3' end. Its homology was confirmed. The initial clone lacks the 5' portion of the gene in comparison to other members of TNF family. To obtain the full length sequence, a nested PCR reaction was carried out using two gene specific oligonucleotides and two vector-specific primers. An additional 72 nucleotides at the 5' end was obtained. The full length sequence was then cloned into the vector pCM-Vsport 2.0 (Life Technologies Inc., Rockville, Md.).

Northern Blot Analysis.

Human multiple tissue Northern blots (Clontech, MTN blots, #7759-1 and #7760-1) were probed with a $^{32}$P-labelled AIM II full length cDNA according to the vendor's instructions. The blots were hybridized overnight in Hybrisol solution (Oncor), preheated to 42° C. before use, followed by two subsequent washes in 2×SSC/0.1% SDS and 0.2×SSC/0.1% SDS at 42° C. and visualized using a PhosphoImager™ (Molecular Dynamics Co.).

In situ Hybridization and FISH Detection.

To determine the precise chromosomal location of the AIM II gene, single-copy gene fluorescence in situ hybridization (FISH) to normal human metaphase chromosome spreads was attempted (Lawrence et al., 1988). A 2 Kb cDNA was nick-translated using Digoxigenin-11-dUTP (Boehringer Mannheim) and FISH was carried out as detailed in Johnson et al., 1991b. Individual chromosomes were counterstained with DAPI and color digital images, containing both DAPI and gene signal detected with Rhodamine, were recorded using a triple-band pass filter set (Chroma Technology, Inc., Brattleburo, Vt.) in combination with a cooled charge coupled-device camera (Photometrics, Inc., Tucson, Ariz.) and variable excitation wave length filters (Johnson et al., 1991a). Images were analyzed using the ISEE software package (Inovision Corp., Durham, N.C.).

Cells and Reagents

The human breast carcinoma MDA-MB-231, subclone 2LMP, obtained from in vivo passage of MDA-MB-231 cells in athymic nude mice, was used in all the experiments. MC-38 is a 1,2-dimethylhydrazine induced murine colon adenocarcinoma which is of H-2b origin. Human T lymphoma line Jurkat and CHO lines were obtained from the American Type Culture Collection (ATCC, Rockville, Md.). A human melanoma antigen gp100 reactive CD8+ T-cell line TIL1200 was kindly provided by Dr. Yutaka Kawakami (National Cancer Institute, Bethesda, Md.). All tumor cell lines were grown and maintained in RPMI1640 medium containing 10% FCS, except MDA-MB-231, which used Dulbecco's modified Eagle's medium as basal medium. HLA-A2 restricted TIL 1200 was grown in Aim-V medium containing 10% human serum and 1000 U of IL-2. The apoptosis inducing anti-Fas Mab CH-11 was obtained from Upstate Biotechnology. Interfreon was obtained from Biosource International (Calif.).

Production of Soluble AIM II.

The sequence encoding amino acids 74–240 of AIM II, i.e., the putative extracellular domain, was subcloned into the vector pFLAG.CMV-1 in frame with sequences encoding the preprotrypsin signal peptide and the FLAG peptide tag. The resulting construct, pFLAG-sAIM II, was transfected into 293T cells to generate recombinant sAIM II. Culture media from cells transfected pFLAG.CMV-1 or pFLAG-sAIM II were passed through anti-FLAG mAb (Eastman Kodak Co.) affinity columns. The column eluents were fractionated by SDS-PAGE and sAIM II was detected by western blot analysis, using the anti-FLAG mAb and ECL detection reagents (Amersham International).

Generation of Recombinant Receptor-Fc Fusion Proteins

A cDNA encoding extracellular domain of human LTβR was amplified from a HepG2 cells by RT-PCR technique. The sequences of oligonucleotide primers are as following: Forward 5° CGGGATCCATGCTCCTGCCTTGGGCCAC 3' (SEQ ID NO:48); and Reverse: 5' GCGGATC-CTGGGGGCAGTGGCTCTAATGG 3' (SEQ ID NO:49) and contained BamHI restriction sites on each end to facilitate the cloning of PCR product into the pSK+ vector (Stratagene). The amplified sequence was subjected to BamHI digestion and ligated to BamHI cut pSK+ vector for sequencing. The fidelity of amplified cDNA fragment was confirmed by dideoxy DNA sequencing. To obtain human LTβR-Fc fusion protein, extracellular domain of LTβR was excised from pSK+ vector with BamHI restriction endonuclease and ligated to BglII cut pUC19-IgG1-Fc vector to allow in frame ligation. To generate recombinant baculovirus, fusion gene was firstly excised with HpaI/HindIII from pUC19-IgG-Fc vector, followed by ligation with SmaI cut pBacPAK9 vector (Clontech Co.) after fill-in, then co-transfected with linearized BacPAK6 DNA (Clontech Co.) into Sf9 cells. To obtain recombinant soluble LTβR fusion protein, five days culture supernatants from recombinant virus infected insect Sf21 cells was filtered and trapped onto protein A Sepharose beads, the bound sLTβR protein was then eluted with glycine buffer (pH 3.0) and followed by dialysis in PBS. Production of TR2-Fc fusion protein has been described.

Generation of LTβR and TR2 Antibodies

Balb/cJ mice (The Jackson Laboratory, Bar Harbor, Me.) were immunized with LTβR-Fc fusion proteins in Freund's adjuvant. Mice were boosted three times then the spleen cells were fused with the murine myeloma NS-1 cells in the presence of 50% polyethylene glycol in HEPES (PEG 1500, Boehringer Mannheim), followed by culture in RPMI1640/HAT and RPMI1640/HT selective media (Boehringer Co.). Supernatant from positive wells were tested for the ability to bind LTβR-Fc fusion protein, but not human IgGI by ELISA. Hybridomas producing antibodies against LTβR-Fc fusion protein were cloned by limiting dilution three times. To produce large amount of mAbs, $10^7$ hybridoma cells were injected into pristane treated peritoneal cavity of Balb/c mice, and mAbs was subsequently purified from ascites by affinity chromatography. Similarly, using TR2-GST fusion protein, monoclonal antibodies against TR2 were produced and screened by ELISA assay.

in vitro Growth Assays

Cells (5,000 cells per well) were plated in triplicate in 24-multiwell tissue culture plates with IMEM in the presence of either 10% FBS or 1% FBS. The number of live cells were determined by trypan blue exclusion method at day 3, day 5 or day 7. Cells were refed with fresh medium every two days during this time course.

A soluble tetrazolium/formazan (XTT) assay for cell growth in a 96-well plate was performed. Cells (2,000–4,000 cells/well) were grown in IMEM medium with 10% FBS or 1% FBS. After four to five days culture, XTT (1.0 mg/ml plus PMS at 1.53 mg/ml) was added to each well and incubated for four hours at 37° C. Absorbance at 450 nm was measured with the Dynatech Model MR700.

FACS Analysis

Cells were collected by trypsinization or aspiration, and centrifuged at 1500–2000 rpm for 5 min. The cell pellets were resuspended and washed in 5 ml ice-cold PBS twice. And then, the cells were incubated with Flag-tagged AIM II protein or Abs at 10 μg/ml in the binding buffer (HBSS containing 10% BSA, 20 mM HEPES, pH 7.2, 0.02% NaN$_3$, and 25 μg/ml normal rat Ig) for 30 min at 4° C. Cells were then washed and stained with phycoerythrin (PE) conjugated to goat anti-mouse IgG at 20 μg/ml as described. To compete for cell surface binding, soluble LTβR-Fc fusion protein, TR2-Fc at 10 μg/ml was preincubated with AIM II for 30 min before adding to cells. Fluorescence was analyzed by a FACscan flow cytometer (Becton Dickinson, Mountain View, Calif.).

For apoptosis assay, cell pellets were resuspended in 1× binding buffer (10 mM HEPES pH 7.4, 0.15 M NaCl, 5 mM KCl, 1 mM MgCl$_2$, 1.8 mM CaCl$_2$) containing 1:100 dilution of Annexin V-FITC (Trevigen, Gaithersburg, Md.) and 50 μg/ml of propidium iodide and incubated at 4° C. for 15 min. The fluorescence of Annexin V-FITC and propidium iodide of individual cells were analyzed by flow cytometry (Coulter).

Retroviral Transduction of Tumor Cells

A retroviral vector was used to stably transduce tumor cells with AIM II gene. To construct a plasmid encoding the AIM II, a 1.9 kb NotI/SalI fragment containing the AIM II cDNA was inserted into a parental plasmid pG1 SamEN. This retroviral backbone was derived from the Moloney murine leukemia virus and the AIM II gene was under the transcription control of the long-terminal repeat from the Moline murine leukemia virus. Generation of the retroviral packaging line was described previously (Markowitz et al.). Briefly, 30 μg of pG1SamEN-AIM II DNA were used to transfect a mixture of $2\times10^5$ PA317 amphotropic packaging line and $3\times10^5$ GP+E86 ecotropic packaging line. After 2 week of selection, high-titer G418-resistant PA317 clones were then selected to recreate the packaging line PA-AIM II and used for gene transfer into tumor cells. A control retrovirus producing line PA-neo was also used. These packaging lines were grown for 20 h and the retroviral supernatants were harvested, added to a 75% confluent flask of wild type MDA-MB-231 or MC-38 respectively. Following transduction with a recombinant retrovirus encoding the human AIM II, AIM II expressing MDA-MB-231 or MC-38 cells were selected with the neomycin analogue G418 and designated MDA-MB-231/AIM II or MC-38/AIM II respectively. AIM II expression in these tumor cells was confirmed by Northern blot analyses. All stable transfectants including MDA-MB-231/AIM II, vector control line MDA-MB-231/neo, MC-38/AIM II and the vector control line MC-38/neo were grown and maintained in the presence of G418 at 1.5 mg/ml and 0.375 mg/ml, respectively.

Coculture Assays of Jurkat Cells

The MDA-MB-231 cells were plated in 6-well tissue culture plates and allowed to grow to confluence. Following removal of media and washing of the monolayers with 1×PBS, $1\times10^6$ Jurkat cells (nonadherant) were plated in 1 ml of RPMI medium over amonolayer or an empty wells. Wells with MDA-MB-231 cells alone (without overlaying Jurkat cells) were maintained as additional control. After 24 or 48 hours of culture, the nonadherant phase of the mixed culture was collected from the 6-well plated after gentle rocking of the plate and assayed for viability using trypan blue exclusion. For detection of apoptosis, 20,000 cells were measured per sample using Annexin V-FITC FACScan flow cytometer.

Lymphokine Release Assay

The lymphokine release assays were performed to detect human PBL reactivity with AIM II as previously described. (Zhai et al.) Briefly, human PBL cells were incubated for 5 days in the presence of anti -CD3 mAb (0.1 μg/ml) and rIL-2 20 U/ml plus AIM II protein at various concentrations, the supernatants were collected and the secretion of IFNγ were determined using ELISA kits purchased from R&D Systems (Minneapolis, Minn.).

Tumorigenicity Studies

Female athymic Ncr-nu nude mice, 6 week old, were obtained from the Frederick Cancer Research and Development Center, National Institute of Health (Frederick, Md.) and Charles River Laboratories (Raleigh, N.C.). Female C57BL/6 mice, 6–7 wk old, were purchased from Harlan Sprague Dawley (Indianapolis, Ind.). MDA-MB-231 cells ($1\times10^6$) were injected on day 0 into the mammary fat pad of the female athymic nudemice and similarly, MC-38 cells were injected s.c. into the flank region of C58BL/6 mice. Mice were then ear tagged and randomized. Tumor size was assessed by measuring perpendicular diameters with a caliper twice weekly in a blinded fashion. Each treatment group consisted often animals and experiments were repeated three times. Tumor histological examination was carried out with H/E staining.

Example 6

Detection of AIM II Expression by BIAcore Analysis

CHO cells were transfected with either an AIM II-Flag tag expression vector or an BAP-Flag (negative control). Three days after transfection, AIM II expression was determined using the BIAcore instrument (BIAcore, Inc.) which permits real-time measurements of protein binding events to immobilized AIM II receptor, lymphotoxin-β receptor (BIAcore sensorgram detects binding by changes in refractive index at the surface of the flow cell). A lymphotoxin-β receptor-Fc fusion protein was covalently immobilized to the BIAcore flow cell via amine groups using N-ethyl-N'-(dimethylaminopropyl)carbodiimide/N-hydroxysuccinimide chemistry. Various dilutions of AIM II-Flag and the negative control (BAP-Flag) conditioned serum-free media were applied to the lymphotoxin-β-receptor-derivatized flow cell at 5 µl/min for a total volume of 50 µl. The amount of bound protein was determined after washing the flow cell with HBS buffer (10 mM HEPES, pH 7.4, 150 mM NaCl, 3.4 mM EDTA, 0.005% Surfactant P20). The flow cell surface was regenerated by displacing bound protein by washing with 20 µl of 10 mM HCl.

The specific binding to the lymphotoxin-β-receptor was detected at up to 10-fold dilution of the conditioned media from AIM II-Flag cultures, whereas, no significant binding was observed for the negative control (BAP-Flag) conditioned media. This demonstrates that AIM II-Flag binding is specific to lymphotoxin-β-receptor and not to the Fc portion of the fusion protein. Moreover, specific receptor binding by AIM II-Flag protein indicates that it exhibits a native structure as secreted by the cells. Thus, this BIAcore-based assay can be used to detect expression of AIM II from conditioned media and other biological fluids. Further, by using known amounts of pure AIM II protein this assay can be developed into a quantitative assay for determining AIM II concentrations.

Example 7

Activation-induced Apoptosis Assay

Activation-induced apoptosis is assayed using SupT-13 T leukemia cells and is measured by cell cycle analysis. The assay is performed as follows. SupT-13 cells are maintained in RPMI containing 10% FCS in logarithmic growth (about $1 \times 10^6$). Sup-T13 cells are seeded in wells of a 24 well plate at $0.5 \times 10^6$/ml, 1 ml/well. AIM II protein (0.01, 0.1, 1, 10, 100, 1000 ng/ml) or buffer control is added to the wells and the cells are incubated at 37° C. for 24 hours. The wells of another 24 well plate were prepared with or without anti-CD3 antibody by incubating purified BC3 mAb at a concentration of 10 µg/ml in sterile-filtered 0.05M bicarbonate buffer, pH 9.5 or buffer alone in wells at 0.5 ml/well. The plate is incubated at 4° C. overnight. The wells of antibody coated plates are washed 3 times with sterile PBS, at 4° C. The AIM II treated Sup-T13 cells are transferred to the antibody coated wells and incubated for 18 hr., at 37° C. Apoptosis is measured by cell cycle analysis using propidium iodide and flow cytometry. Proliferation of treated cells is measured by taking a total of 300 µl of each treatment well and delivering in to triplicate wells (100 µl/well) of 96 well plates. To each well add 20 µl/well $^3$H thymidine (0.5 µCi/20 µl, 2 Ci/mM) and incubate 18 hr., at 37° C. Harvest and count $^3$H-thymidine uptake by the cells. This measurement is used to confirm an effect on apoptosis if observed by other methods. The positive control for the assay is Anti-CD3 crosslinking alone. In addition, profound and reproducible apoptosis in this line using anti-fas monoclonal antibody (500 ng/ml in soluble form-IgM mAb) has been demonstrated. The negative control for the assay is medium or buffer alone. Also, crosslinking with another anti-CD3 mAB (OKT3) has been shown to have no effect.

If an effect is observed by cell cycle analysis the cells will be further stained for the TUNEL assay for flow cytometry or with Annexin V, techniques well known to those skilled in the art.

Example 8

CD3-induced Proliferation Assay

A CD3-induced proliferation assay is performed on PBMCs and is measured by the uptake of $^3$H-thymidine. The assay is performed as follows. Ninety-six well plates are coated with 100 µl/well of mAb to CD3(HIT3a, Pharmingen) or isotype-matched control mAb (B33.1) overnight at 4° C. (1 µg/ml in 0.05M bicarbonate buffer, pH 9.5), then washed three times with PBS. PBMC are isolated by F/H gradient centrifugation from human peripheral blood and added to quadruplicate wells ($5 \times 10^4$/well) of mAb coated plates in RPMI containing 10% FCS and P/S in the presence of varying concentrations of AIM II protein (total volume 200 µl). Relevant protein buffer and medium alone are controls. After 48 hr. culture at 37° C., plates are spun for 2 min. at 1000 rpm and 100 µl of supernatant is removed and stored −20° C. for measurement of IL-2(or other cytokines) if effect on proliferation is observed. Wells are supplemented with 100 µl of medium containing 0.5 µCi of $^3$H-thymidine and cultured at 37° C. for 18–24 hr. Wells are harvested and incorporation of $^3$H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative control for CD3-induced proliferation and medium or buffer are used as negative controls for the effects of AIM II proteins.

Example 9

Effect of AIM II on the Expression of MHC Class II, Costimulatory and Adhesion Molecules and Cell Differentiation of Monocyte-Derived Human Dendritic Cells Dendritic cells are generated by the expansion of proliferating precursors found in the peripheral blood: adherent PBMC or elutriated monocytic fractions are cultured for 7–10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF-α, causes a rapid change in surface phenotype (increased expression of MHC class I and II, costimulatory and adhesion molecules, downregulation of FcγRII, upregulation of CD83). These changes correlate with increased antigen-presenting capacity and with functional maturation of the dendritic cells.

FACS analysis of surface antigens is performed as follows. Cells are treated 1–3 days with various concentrations of AIM-II (0.1, 1, 10, 100, 1000 ng/ml) or LPS as positive control, washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Effect on the Production of Cytokines

Cytokines generated by dendritic cells, in particular IL-12, are important in the initiation of T-cell dependent immune responses. IL-12 strongly influences the development of Th1 helper T-cell immune response, and induces cytotoxic T and NK cell function. An ELISA will be used to measure the IL-12 release as follows. Dendritic cells ($10^6$/ml) are treated with AIM-II (0.1, 1, 10, 100, 1000 ng/ml) for 24 hours. LPS (100 ng/ml) is added to the cell culture as positive control. Supernatants from the cell cultures are then collected and analyzed for IL-12 content using commercial ELISA kit. The standard protocols provided with the kits are used.

Effect on the Expression of MHC Class II, Costimulatory and Adhesion Molecules

Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis will be used to examine the surface antigens as follows. Monocytes are treated 1–5 days with various concentrations of AIM-II (0.1, 1, 10, 100, 1000 ng/ml) or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Effect on Monocyte Survival

Human peripheral blood monocytes progressively lose viability when cultured in absence of serum or other stimuli. Their death results from internally regulated processes (apoptosis). Addition to the culture of activating factors, such as TNF-α, dramatically improves cell survival and prevents DNA fragmentation. Propidium iodide staining will be used to measure apoptosis as follows. Monocytes ($10^7$/ml) are cultured in suspension in polypropylene tubes in DMEM for two days in presence or absence of TNF-α (100 ng/ml, positive control) or AIM-II (0.1, 1, 10, 100, 1000 ng/ml). Cell viability is assessed by propidium iodide (PI) staining. Cells are suspended at a concentration of $2\times10^6$/ml in PBS containing PI at a final concentration of 5 μg/ml, and then incubated at room temperature for 5 minutes before FACScan analysis. PI uptake has been demonstrated to correlate with DNA fragmentation in this experimental paradigm.

Effect on Cytokine Release

An important function of monocytes/macrophages is their regulatory activity on other cellular populations of the immune system through the release of cytokines after stimulation. An ELISA to measure the IL-1β release is performed as follows. Human monocytes are added at $10^6$/ml in 48-well plates and various concentrations of AIM-II are added (0.1, 1, 10, 100, 1000 ng/ml) in presence or absence of 100 ng/ml LPS. After 24 hour incubation, the supernatants are collected and assayed for the presence of cytokines by ELISA kits. The standard protocols provided with the kits are used.

Example 10

Affinity Purification of Soluble AIM II for N-terminal Sequence Analysis

Previous data indicated that a BIAcore chip derivatized with the lymphotoxin beta receptor (LTβR)-Fc fusion protein was able to specifically bind AIM II (a.a. 74–240)-Flag fusion protein (See Example 5, section E and FIG. 7A). The LTβR BIAcore chip was then used to detect expression of soluble AIM II protein from conditioned media of non-Flag tagged AIM II stable transfectants in order to determine which cell line(s) should be used for further purification for N-terminal sequence analysis.

CHO cells were transfected with an expression construct (pC4 vector) consisting of the extracellular region of AIM II (amino acids 60–240) fused to the ck-beta 8 signal peptide. Clones were selected for high expression by growth in media containing methotrexate. The clones with the highest amount of binding to LTβR BIAcore chip were further amplified. Conditioned media (20 mL) from CHO 11, a high level AIM II producing clone, was obtained. A second AIM II construct encoding the complete full length cDNA was transfected into murine MCA-38 carcinoma cells and subject to selection with G418. Conditioned media was obtained from these transfected MCA-38 cells.

Conditioned media from the stable transfectants, CHO 11 or MCA-38 cells, were filtered, centrifuged at 10,000×g and then passed over an MCIF-Fc affinity column (control column) followed by the LTβR-Fc affinity column (0.2 mL bed volume). The columns were washed with several bed column volumes HEPES buffered saline containing 0.005% Surfactant P-20. Bound protein was eluted with 10 mM HCl (3×0.5 mL fractions) and immediately neutralized with TRIS buffer. The fractions eluted from the LTβR column retained binding to LTβR BIAcore chip, whereas, fractions eluted from the control MCIF-Fc column were negative for binding. The eluted fractions were dried in Spedvac then resuspended in 20 μL water. An aliquot of the eluted protein was analyzed by reducing SDS-PAGE gels and detected by silver staining. A band of approximately ~25 kDa and ~21 kDa was detected specifically bound to the LTβR column from CHO-11 and MCA-38 cell lines. The remaining eluted material was subject to SDS-PAGE and blotted onto PVDF membrane for N-terminal sequence analysis.

The N-terminus of the AIM II molecule purified from MCA-38 cells started at residue 83 within the predicted extracellular region of the molecule (Table 3). The results of the AIM II from CHO-11 also confirmed that this protein correspond to AIM II protein; the N-terminus contained two sequences starting three residues apart which start within the ck-beta 8 signal peptide followed by the extracellular region of AIM II starting at residue 60 (Table 3). Thus, the natural processed form of AIM II should correspond to residues 83–240 and have a molecular mass of 17,284 daltons. The apparent electrophoretic mobility of ~21 kDa is consistent with glycosylation as evident by presence of several electrophoretic species. Similarly, the ~25 kDa apparent molecular mass of the CHO-11 expressed ck-beta8/AIM II fusion protein was larger than that predicted from its sequence (20,361). Again this might also be due to glycosylation of the protein (there is one N-glycosylation site at residue 104 of full length AIM II).

TABLE 3

N-terminus of AIM2 purified from MCA-38 or CHO-11 clone conditioned media.

```
N-terminus MCA-38'                                    LIQER.(SEQ ID NO:58)
N-terminus CHO 11¹(40%)    .QAGS................................(SEQ ID NO:59).
N-terminus CHO-11¹(40%)    ..GSQLH..............................(SEQ ID NO:60).
ck-beta-8-AIM2 sequence²   SQAGSQLHWRLGEMVTRLPDGPAGSWEQLIQERN   (SEQ ID NO:61)
```

¹= Affinity purified AIM II from MCA-38 or CHO-11 conditioned media.
²= Amino acid sequence at junction of ck-beta-8 and extracellular region of AIM II. Double underlined sequence corresponds to ck beta 8 signal sequence (SQA), and in the case of the GS residues sequence introduced during cloning. AIM II sequence starts at the 6th residue, Q.
Values in parenthesis represent percentage of each sequence found in AIM II sample.

underlined sequence corresponds to ck beta 8 signal sequence (SQA), and in the case of the GS residues sequence introduced during cloning. AIM II sequence starts at the 6th residue, Q. Values in parenthesis represent percentage of each sequence found in AIM II sample.

Figure 12:
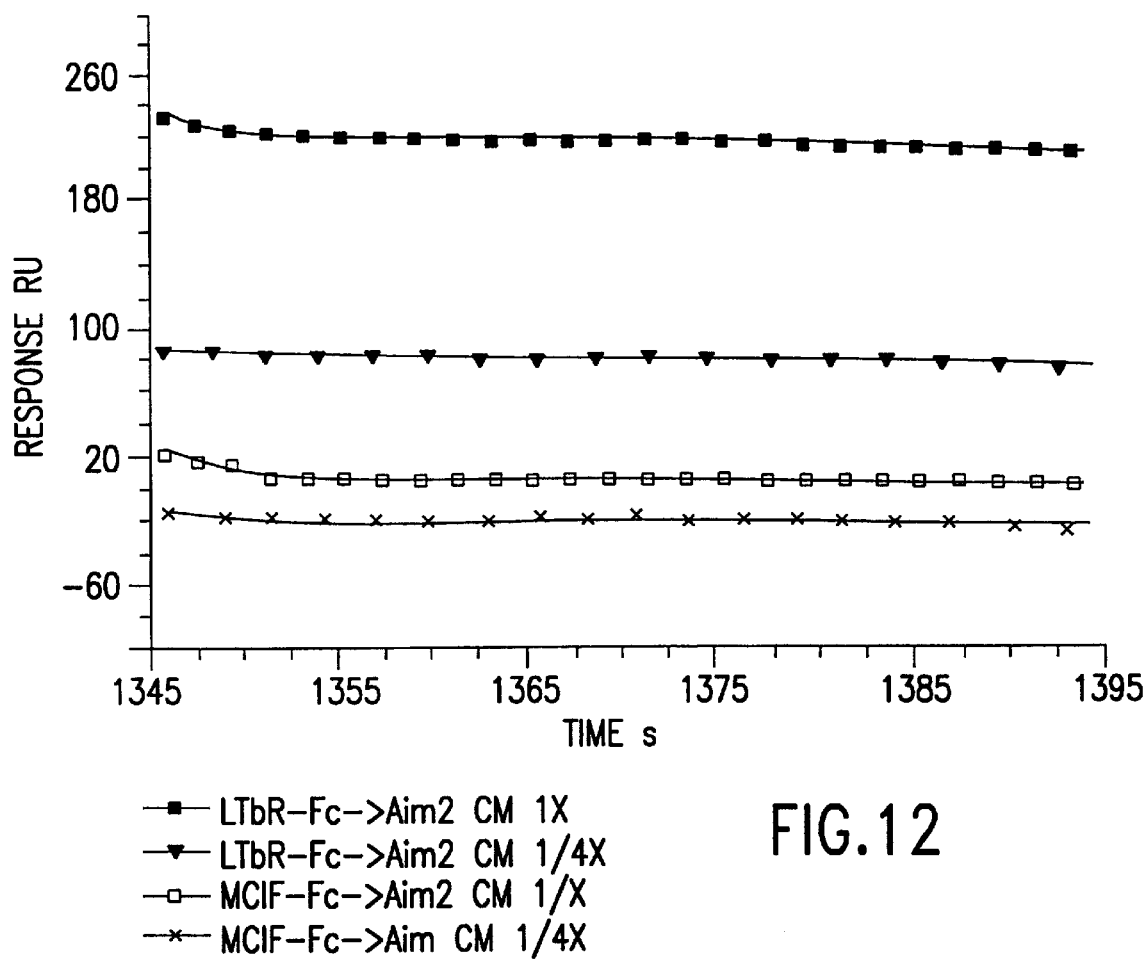
FIG. 12 shows a sensorgram of specificity of binding of MCA-38 AIM II conditioned media to LTβR-FC versus MCIF-Fc immobilized on BIAcore chip. Conditioned media was analyzed on a BIAcore instrument flowcell derivatized with lymphotoxin beta receptor Fc fusion protein. The conditioned media (100 μL) was flown over the chip at 5 μL/min and washed with HBS buffer also at 5 μL/min. The shown data represents the net bound (off-rate) region of the plot after binding of AIM II to immobilized receptor and is measured in relative mass units (RU) versus time. The binding conditions were performed at high receptor chip densities under diffusion-limited conditions. Legend: LTβR-Fc and MCIF-Fc refer to binding data from LTβR-Fc or MCIF-Fc immobilized BIAcore chip surfaces, respectively.

The Sensorgram of specificity of binding of MCA-38 AIM II conditioned media to LTβR-Fc versus MCIF-Fc immobilized on BIAcore chip is shown in FIG. 12. The conditioned media was analyzed on a BIAcore instrument flowcell derivatized with lymphotoxin beta receptor Fc fusion protein. The conditioned media (100 μL) was flown over the chip at 5 μL/min and washed with HBS buffer also at 5 μL/min. The shown data represents the net bound (off-rate) region of the plot after binding of AIM II to immobilized receptor and is measured in relative mass units (RU) versus time. The binding conditions were performed at high receptor chip densities under diffusion-limited conditions. Legend: LTβR-Fc and MCIF-Fc refer to binding data from LTβR-Fc or MCIF-Fc immobilized BIAcore chip surfaces, respectively.

Figure 13:
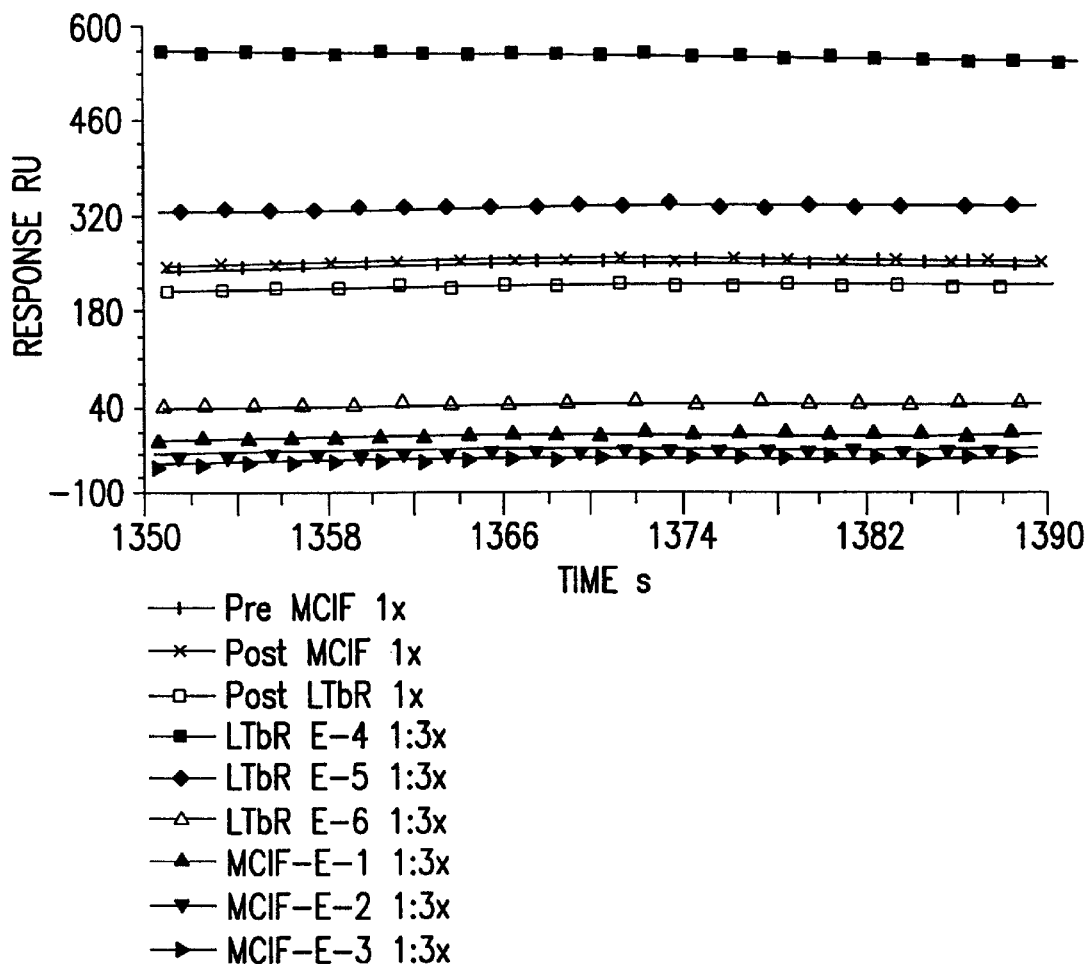
FIG. 13 shows the determination of the LTβR binding by AIM II eluted from LTβR-FC column. Binding conditions were as described in FIG. 11. Legend: LTβR and MCIF refer to binding data from LTβR-FC or MCIF-Fc immobilized BlAcore chip surfaces, respectively. Undiluted Conditioned media from MCA38 cells was analyzed before (pre) and after passage through MCIF-Fc (post-MCIF) and LTβR-Fc (post-LTβR) affinity columns. Fractions (1 mL) eluted from the LTβR (E4-6) and MCIF-Fc (E1-3) affinity columns were diluted 3-fold and tested for binding to LTβR BIAcore chip.

Determination of the LTβR binding by AIM II eluted from LTβR-Fc column is shown in FIG. 13. LTβR and MCIF refer to binding data from LTβR-Fc or MCIF-Fc immobilized BIAcore chip surfaces, respectively. Undiluted Conditioned media from MCA38 cells was analyzed before (pre) and after passage through MCIF-Fc (post-MCIF) and LTβR-Fc (post-LTβR) affinity columns. Fractions (1 mL) eluted from the LTβR (E4–6) and MCIF-Fc (E1–3) affinity columns were diluted 3-fold and tested for binding to LTβR BIAcore chip.

Example 11

Effect of AIM II in Treating Adjuvant-Induced Arthritis in Rats

An analysis of the use of AIM II to treat rheumatoid arthritis (RA) is performed through the use of an adjuvant-induced arthritis (AIA) model in rats. AIA is a well-characterized and reproducible animal model of rheumatoid arthritis which is well-known to one of ordinary skill in the art (Pearson, *Ann. Rheum. Dis.* 15: 379(1956); Pearson et al., *Arthritis Rheum.* 2: 440(1959)). AIM II is expected to inhibit the increase in angiogenesis or the increase in endothelial cell proliferation required to sustain the invading pannus in bone and cartilage observed in this animal model of RA. Lewis and BB rats (available from Charles River Lab, Raleigh, N.C. and the University of Massachusetts Medical Center, Worcester, Mass.) are used as the common and responsive strains for adjuvant-induced arthritis in these experiments.

Initiation of the arthritic condition is induced by the intradermal injection of 0.1 ml adjuvant (5 mg/ml) into the base of the tail. Groups of 5 to 6 rats receive either 0.1 to 1.0 mg/kg AIM II or vehicle intra-articularly 20 days after the injection of adjuvant. At this time point acute inflammation reaches a maximal level and chronic pannus formation will have just begun. The effect of AIM II on pannus formation is analyzed radiologically once each week after day 15 following adjuvant challenge essentially as described by Taurog and colleagues (*J. Exp. Med.* 162: 962(1985)). Briefly, rats are anesthetized with ether or chloral hydrate and positioned so that both hind limbs are X-rayed together. The X-ray films are examined blindly using a scoring system of 0–3 for periosteal reaction, bony erosions, joint space narrowing and destruction. When there is a significant amount of joint damage in vehicle-treated rats, the animals are sacrificed. At this point, the paws are evaluated histologically for the relative degree of tissue damage and for the therapeutic effect AIM II has elicited on these joints.

Finally, AIM II- and vehicle-treated animals undergo a clinical evaluation twice per week to assess hind paw volume using a plethysmometer system and body weight.

Example 12

Effect of AIM II in Treating Collagen-Induced Arthritis in Mice

An analysis of the use of AIM II to treat rheumatoid arthritis (RA) may be performed through the use of a collagen-induced autoimmune arthritis (CIA) model in mice. CIA is another well-characterized and reproducible animal model of rheumatoid arthritis which is well-known to one of ordinary skill in the art (Courtenay et al., *Nature* 283: 666(1980); Wooley et al, *J. Exp. Med.* 154: 688 (1981); Holmdahl et al., *Immunol. Reviews* 118: 193(1990)). AIM II is expected to induce apoptosis and inhibit the synovial cell proliferation required to form the invading pannus in bone and cartilage observed in both rheumatoid arthritis and this autoimmune animal model of RA.

DBA/1 Lac J mice, available from Jackson Lab (Bar Harbor, Me.) are used as the most universally susceptible strain for collagen-induced arthritis in these experiments.

Initiation of the arthritic condition is induced by the intradermal injection of 0.1 ml of 1 mg/ml of bovine type II collagen in Complete Freund's Adjuvant into the base of the tail. Three weeks later, the animal are injected with 40 μg of LPS to accelerate the development of arthritis. Groups of 10 mice will receive either 0.1–1 mg/kg AIM II or vehicle intradermally or intra-articularly 7–15 days after the injection of LPS. At this time point, acute inflammation is expected to reached a maximal level and chronic pannus formation will have just begun. The effect of AIM II on arthritis is monitored and analyzed clinically using the following score: 0=normal, 0.5=swollen digits, 1=entire paw swollen, 2=deformity and 3=ankylosis. When it is determined that a significant amount of ankylosis has occurred in the paws of vehicle-treated rats, the animals will be sacrificed and the paws are evaluated histologically for the relative degree of pannus formation, cartilage and bone destruction and for what effect AIM II has elicited on these joints.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

SEQUENCE LISTING

<160> NUMBER OF SEQ ID NOS: 61

<210> SEQ ID NO 1
<211> LENGTH: 1169
<212> TYPE: DNA
<213> ORGANISM: Homo sapiens
<220> FEATURE:
<221> NAME/KEY: CDS
<222> LOCATION: (49)..(768)
<223> OTHER INFORMATION: DNA (cDNA)

<400> SEQUENCE: 1

```
gaggttgaag gacccaggcg tgtcagccct gctccagaga ccttgggc atg gag gag      57
                                                     Met Glu Glu
                                                      1 agt gtc gta cgg ccc tca gtg ttt gtg gtg gat gga cag acc gac atc     105
Ser Val Val Arg Pro Ser Val Phe Val Val Asp Gly Gln Thr Asp Ile
     5                  10                  15 cca ttc acg agg ctg gga cga agc cac cgg aga cag tcg tgc agt gtg     153
Pro Phe Thr Arg Leu Gly Arg Ser His Arg Arg Gln Ser Cys Ser Val
 20                  25                  30                  35 gcc cgg gtg ggt ctg ggt ctc ttg ctg ttg ctg atg ggg gct ggg ctg     201
Ala Arg Val Gly Leu Gly Leu Leu Leu Leu Leu Met Gly Ala Gly Leu
                 40                  45                  50 gcc gtc caa ggc tgg ttc ctc cag ctg cac tgg cgt cta gga gag         249
Ala Val Gln Gly Trp Phe Leu Leu Gln Leu His Trp Arg Leu Gly Glu
             55                  60                  65 atg gtc acc cgc ctg cct gac gga cct gca ggc tcc tgg gag cag ctg     297
Met Val Thr Arg Leu Pro Asp Gly Pro Ala Gly Ser Trp Glu Gln Leu
         70                  75                  80 ata caa gag cga agg tct cac gag gtc aac cca gca gcg cat ctc aca     345
Ile Gln Glu Arg Arg Ser His Glu Val Asn Pro Ala Ala His Leu Thr
 85                  90                  95 ggg gcc aac tcc agc ttg acc ggc agc ggg ggg ccg ctg tta tgg gag     393
Gly Ala Asn Ser Ser Leu Thr Gly Ser Gly Gly Pro Leu Leu Trp Glu
100                 105                 110                 115 act cag ctg ggc ctg gcc ttc ctg agg ggc ctc agc tac cac gat ggg     441
Thr Gln Leu Gly Leu Ala Phe Leu Arg Gly Leu Ser Tyr His Asp Gly
                 120                 125                 130 gcc ctt gtg gtc acc aaa gct ggc tac tac tac atc tac tcc aag gtg     489
Ala Leu Val Val Thr Lys Ala Gly Tyr Tyr Tyr Ile Tyr Ser Lys Val
             135                 140                 145 cag ctg ggc ggt gtg ggc tgc ccg ctg ggc ctg gcc agc acc atc acc     537
Gln Leu Gly Gly Val Gly Cys Pro Leu Gly Leu Ala Ser Thr Ile Thr
         150                 155                 160 cac ggc ctc tac aag cgc aca ccc cgc tac ccc gag gag ctg gag ctg     585
His Gly Leu Tyr Lys Arg Thr Pro Arg Tyr Pro Glu Glu Leu Glu Leu
165                 170                 175 ttg gtc agc cag cag tca ccc tgc gga cgg gcc acc agc agc tcc cgg     633
```

| | | | | | | | | | | | | | |
|---|---|---|---|---|---|---|---|---|---|---|---|---|---|
|Leu|Val|Ser|Gln|Gln|Ser|Pro|Cys|Gly|Arg|Ala|Thr|Ser|Ser|Arg
|180| | | | |185| | | | |190| | | |195

```
gtc tgg tgg gac agc agc ttc ctg ggt ggt gtg gta cac ctg gag gct    681
Val Trp Trp Asp Ser Ser Phe Leu Gly Gly Val Val His Leu Glu Ala
            200                 205                 210 ggg gag gag gtg gtc gtc cgt gtg ctg gat gaa cgc ctg gtt cga ctg    729
Gly Glu Glu Val Val Val Arg Val Leu Asp Glu Arg Leu Val Arg Leu
            215                 220                 225 cgt gat ggt acc cgg tct tac ttc ggg gct ttc atg gtg tgaaggaagg    778
Arg Asp Gly Thr Arg Ser Tyr Phe Gly Ala Phe Met Val
            230                 235                 240 agcgtggtgc attggacatg ggtctgacac gtggagaact cagagggtgc ctcaggggaa    838
agaaaactca cgaagcagag gctgggcgtg gtggctctcg cctgtaatcc cagcactttg    898
ggaggccaag gcaggcggat cacctgaggt caggagttcg agaccagcct ggctaacatg    958
gcaaaacccc atctctacta aaaatacaaa aattagccgg acgtggtggt gcctgcctgt   1018
aatccagcta ctcaggaggc tgaggcagga taattttgct taaacccggg aggcggaggt   1078
tgcagtgagc cgagatcaca ccactgcact ccaacctggg aaacgcagtg agactgtgcc   1138
tcaaaaaaaa aaaaaaaaaa aaaaaaaaa a                                  1169
```

<210> SEQ ID NO 2
<211> LENGTH: 240
<212> TYPE: PRT
<213> ORGANISM: Homo sapiens

<400> SEQUENCE: 2

```
Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Glu Val Val Val Arg Val Leu Asp Glu Arg Leu
    210                 215                 220
```

-continued

```
Val Arg Leu Arg Asp Gly Thr Arg Ser Tyr Phe Gly Ala Phe Met Val
225                 230                 235                 240
```

<210> SEQ ID NO 3
<211> LENGTH: 455
<212> TYPE: PRT
<213> ORGANISM: Homo sapiens

<400> SEQUENCE: 3

```
Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365
```

```
Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Thr Pro Arg Arg Glu Ala
                405                 410                 415

Thr Leu Glu Leu Leu Gly Arg Val Leu Arg Asp Met Asp Leu Leu Gly
                420                 425                 430

Cys Leu Glu Asp Ile Glu Glu Ala Leu Cys Gly Pro Ala Ala Leu Pro
                435                 440                 445

Pro Ala Pro Ser Leu Leu Arg
    450                 455

<210> SEQ ID NO 4
<211> LENGTH: 205
<212> TYPE: PRT
<213> ORGANISM: Homo sapiens

<400> SEQUENCE: 4

Met Thr Pro Pro Glu Arg Leu Phe Leu Pro Arg Val Cys Gly Thr Thr
1               5                   10                  15

Leu His Leu Leu Leu Gly Leu Leu Val Leu Leu Pro Gly Ala
                20                  25                  30

Gln Gly Leu Pro Gly Val Gly Leu Thr Pro Ser Ala Ala Gln Thr Ala
            35                  40                  45

Arg Gln His Pro Lys Met His Leu Ala His Ser Thr Leu Lys Pro Ala
    50                  55                  60

Ala His Leu Ile Gly Asp Pro Ser Lys Gln Asn Ser Leu Leu Trp Arg
65                  70                  75                  80

Ala Asn Thr Asp Arg Ala Phe Leu Gln Asp Gly Phe Ser Leu Ser Asn
                85                  90                  95

Asn Ser Leu Leu Val Pro Thr Ser Gly Ile Tyr Phe Val Tyr Ser Gln
            100                 105                 110

Val Val Phe Ser Gly Lys Ala Tyr Ser Pro Lys Ala Thr Ser Ser Pro
        115                 120                 125

Leu Tyr Leu Ala His Glu Val Gln Leu Phe Ser Ser Gln Tyr Pro Phe
    130                 135                 140

His Val Pro Leu Leu Ser Ser Gln Lys Met Val Tyr Pro Gly Leu Gln
145                 150                 155                 160

Glu Pro Trp Leu His Ser Met Tyr His Gly Ala Ala Phe Gln Leu Thr
                165                 170                 175

Gln Gly Asp Gln Leu Ser Thr His Thr Asp Gly Ile Pro His Leu Val
            180                 185                 190

Leu Ser Pro Ser Thr Val Phe Phe Gly Ala Phe Ala Leu
        195                 200                 205

<210> SEQ ID NO 5
<211> LENGTH: 205
<212> TYPE: PRT
<213> ORGANISM: Homo sapiens

<400> SEQUENCE: 5

Met Thr Pro Pro Glu Arg Leu Phe Leu Pro Arg Val Cys Gly Thr Thr
1               5                   10                  15

Leu His Leu Leu Leu Leu Gly Leu Leu Val Leu Leu Pro Gly Ala
                20                  25                  30
```

```
Gln Gly Leu Pro Gly Val Gly Leu Thr Pro Ser Ala Ala Gln Thr Ala
            35                  40                  45
Arg Gln His Pro Lys Met His Leu Ala His Ser Thr Leu Lys Pro Ala
 50                  55                  60
Ala His Leu Ile Gly Asp Pro Ser Lys Gln Asn Ser Leu Leu Trp Arg
 65                  70                  75                  80
Ala Asn Thr Asp Arg Ala Phe Leu Gln Asp Gly Phe Ser Leu Ser Asn
                 85                  90                  95
Asn Ser Leu Leu Val Pro Thr Ser Gly Ile Tyr Phe Val Tyr Ser Gln
            100                 105                 110
Val Val Phe Ser Gly Lys Ala Tyr Ser Pro Lys Ala Thr Ser Ser Pro
            115                 120                 125
Leu Tyr Leu Ala His Glu Val Gln Leu Phe Ser Ser Gln Tyr Pro Phe
            130                 135                 140
His Val Pro Leu Leu Ser Ser Gln Lys Met Val Tyr Pro Gly Leu Gln
145                 150                 155                 160
Glu Pro Trp Leu His Ser Met Tyr His Gly Ala Ala Phe Gln Leu Thr
                165                 170                 175
Gln Gly Asp Gln Leu Ser Thr His Thr Asp Gly Ile Pro His Leu Val
            180                 185                 190
Leu Ser Pro Ser Thr Val Phe Phe Gly Ala Phe Ala Leu
            195                 200                 205

<210> SEQ ID NO 6
<211> LENGTH: 281
<212> TYPE: PRT
<213> ORGANISM: Homo sapiens

<400> SEQUENCE: 6

Met Gln Gln Pro Phe Asn Tyr Pro Tyr Pro Gln Ile Tyr Trp Val Asp
 1               5                  10                  15
Ser Ser Ala Ser Ser Pro Trp Ala Pro Pro Gly Thr Val Leu Pro Cys
            20                  25                  30
Pro Thr Ser Val Pro Arg Arg Pro Gly Gln Arg Arg Pro Pro Pro Pro
            35                  40                  45
Pro Pro Pro Pro Pro Leu Pro Pro Pro Pro Pro Pro Pro Pro Leu Pro
 50                  55                  60
Pro Leu Pro Leu Pro Pro Leu Lys Lys Arg Gly Asn His Ser Thr Gly
 65                  70                  75                  80
Leu Cys Leu Leu Val Met Phe Phe Met Val Leu Val Ala Leu Val Gly
                 85                  90                  95
Leu Gly Leu Gly Met Phe Gln Leu Phe His Leu Gln Lys Glu Leu Ala
            100                 105                 110
Glu Leu Arg Glu Ser Thr Ser Gln Met His Thr Ala Ser Ser Leu Glu
            115                 120                 125
Lys Gln Ile Gly His Pro Ser Pro Pro Pro Glu Lys Lys Glu Leu Arg
            130                 135                 140
Lys Val Ala His Leu Thr Gly Lys Ser Asn Ser Arg Ser Met Pro Leu
145                 150                 155                 160
Glu Trp Glu Asp Thr Tyr Gly Ile Val Leu Leu Ser Gly Val Lys Tyr
                165                 170                 175
Lys Lys Gly Gly Leu Val Ile Asn Glu Thr Gly Leu Tyr Phe Val Tyr
            180                 185                 190
Ser Lys Val Tyr Phe Arg Gly Gln Ser Cys Asn Asn Leu Pro Leu Ser
```

```
                195                 200                 205
His Lys Val Tyr Met Arg Asn Ser Lys Tyr Pro Gln Asp Leu Val Met
            210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
                275                 280

<210> SEQ ID NO 7
<211> LENGTH: 24
<212> TYPE: DNA
<213> ORGANISM: Artificial Sequence
<220> FEATURE:
<223> OTHER INFORMATION: Oligonucleotide

<400> SEQUENCE: 7
gcgggatccg gagagatggt cacc                                          24

<210> SEQ ID NO 8
<211> LENGTH: 27
<212> TYPE: DNA
<213> ORGANISM: Artificial Sequence
<220> FEATURE:
<223> OTHER INFORMATION: Oligonucleotide

<400> SEQUENCE: 8
cgcaagcttc cttcacacca tgaaagc                                       27

<210> SEQ ID NO 9
<211> LENGTH: 32
<212> TYPE: DNA
<213> ORGANISM: Artificial Sequence
<220> FEATURE:
<223> OTHER INFORMATION: Oligonucleotide

<400> SEQUENCE: 9
gaccggatcc atggaggaga gtgtcgtacg gc                                 32

<210> SEQ ID NO 10
<211> LENGTH: 27
<212> TYPE: DNA
<213> ORGANISM: Artificial Sequence
<220> FEATURE:
<223> OTHER INFORMATION: Oligonucleotide

<400> SEQUENCE: 10
cgcaagcttc cttcacacca tgaaagc                                       27

<210> SEQ ID NO 11
<211> LENGTH: 40
<212> TYPE: DNA
<213> ORGANISM: Artificial Sequence
<220> FEATURE:
<223> OTHER INFORMATION: Oligonucleotide

<400> SEQUENCE: 11
gctccaggat ccgccatcat ggaggagagt gtcgtacggc                         40

<210> SEQ ID NO 12
```

```
<211> LENGTH: 37
<212> TYPE: DNA
<213> ORGANISM: Artificial Sequence
<220> FEATURE:
<223> OTHER INFORMATION: Oligonucleotide

<400> SEQUENCE: 12
gacgcggtac cgtccaatgc accacgctcc ttccttc                              37

<210> SEQ ID NO 13
<211> LENGTH: 40
<212> TYPE: DNA
<213> ORGANISM: Artificial Sequence
<220> FEATURE:
<223> OTHER INFORMATION: Oligonucleotide

<400> SEQUENCE: 13
gagctcggat ccgccatcat ggaggagagt gtcgtacggc                           40

<210> SEQ ID NO 14
<211> LENGTH: 71
<212> TYPE: DNA
<213> ORGANISM: Artificial Sequence
<220> FEATURE:
<223> OTHER INFORMATION: Oligonucleotide

<400> SEQUENCE: 14
gatgttctag aaagcgtagt ctgggacgtc gtatgggtac accatgaaag ccccgaagta    60
agaccgggta c                                                          71

<210> SEQ ID NO 15
<211> LENGTH: 40
<212> TYPE: DNA
<213> ORGANISM: Artificial Sequence
<220> FEATURE:
<223> OTHER INFORMATION: Oligonucleotide

<400> SEQUENCE: 15
gctccaggat ccgccatcat ggaggagagt gtcgtacggc                           40

<210> SEQ ID NO 16
<211> LENGTH: 37
<212> TYPE: DNA
<213> ORGANISM: Artificial Sequence
<220> FEATURE:
<223> OTHER INFORMATION: Oligonucleotide

<400> SEQUENCE: 16
gacgcggtac cgtccaatgc accacgctcc ttccttc                              37

<210> SEQ ID NO 17
<211> LENGTH: 32
<212> TYPE: DNA
<213> ORGANISM: Artificial Sequence
<220> FEATURE:
<223> OTHER INFORMATION: Oligonucleotide

<400> SEQUENCE: 17
gacgcccatg gaggaggaga gtgtcgtacg gc                                   32

<210> SEQ ID NO 18
<211> LENGTH: 33
<212> TYPE: DNA
<213> ORGANISM: Artificial Sequence
<220> FEATURE:
<223> OTHER INFORMATION: Oligonucleotide
```

-continued

<400> SEQUENCE: 18
gaccggatcc caccatgaaa gccccgaagt aag                         33

<210> SEQ ID NO 19
<211> LENGTH: 27
<212> TYPE: DNA
<213> ORGANISM: Artificial Sequence
<220> FEATURE:
<223> OTHER INFORMATION: Oligonucleotide

<400> SEQUENCE: 19
cgcaagcttc cttcacacca tgaaagc                               27

<210> SEQ ID NO 20
<211> LENGTH: 503
<212> TYPE: DNA
<213> ORGANISM: Homo sapiens
<220> FEATURE:
<221> NAME/KEY: unsure
<222> LOCATION: (17)..(17)
<223> OTHER INFORMATION: n may be any nucleotide
<220> FEATURE:
<221> NAME/KEY: unsure
<222> LOCATION: (60)..(60)
<223> OTHER INFORMATION: n may be any nucleotide
<220> FEATURE:
<221> NAME/KEY: unsure
<222> LOCATION: (64)..(64)
<223> OTHER INFORMATION: n may be any nucleotide
<220> FEATURE:
<221> NAME/KEY: unsure
<222> LOCATION: (95)..(95)
<223> OTHER INFORMATION: n may be any nucleotide
<220> FEATURE:
<221> NAME/KEY: unsure
<222> LOCATION: (103)..(103)
<223> OTHER INFORMATION: n may be any nucleotide
<220> FEATURE:
<221> NAME/KEY: unsure
<222> LOCATION: (168)..(168)
<223> OTHER INFORMATION: n may be any nucleotide
<220> FEATURE:
<221> NAME/KEY: unsure
<222> LOCATION: (262)..(262)
<223> OTHER INFORMATION: n may be any nucleotide
<220> FEATURE:
<221> NAME/KEY: unsure
<222> LOCATION: (267)..(267)
<223> OTHER INFORMATION: n may be any nucleotide
<220> FEATURE:
<221> NAME/KEY: unsure
<222> LOCATION: (281)..(281)
<223> OTHER INFORMATION: n may be any nucleotide
<220> FEATURE:
<221> NAME/KEY: unsure
<222> LOCATION: (285)..(285)
<223> OTHER INFORMATION: n may be any nucleotide
<220> FEATURE:
<221> NAME/KEY: unsure
<222> LOCATION: (300)..(300)
<223> OTHER INFORMATION: n may be any nucleotide
<220> FEATURE:
<221> NAME/KEY: unsure
<222> LOCATION: (306)..(306)
<223> OTHER INFORMATION: n may be any nucleotide
<220> FEATURE:
<221> NAME/KEY: unsure
<222> LOCATION: (311)..(311)
<223> OTHER INFORMATION: n may be any nucleotide
<220> FEATURE:
<221> NAME/KEY: unsure
<222> LOCATION: (331)..(331)
<223> OTHER INFORMATION: n may be any nucleotide
<220> FEATURE:

```
<221> NAME/KEY: unsure
<222> LOCATION: (342)..(342)
<223> OTHER INFORMATION: n may be any nucleotide
<220> FEATURE:
<221> NAME/KEY: unsure
<222> LOCATION: (347)..(347)
<223> OTHER INFORMATION: n may be any nucleotide
<220> FEATURE:
<221> NAME/KEY: unsure
<222> LOCATION: (374)..(374)
<223> OTHER INFORMATION: n may be any nucleotide
<220> FEATURE:
<221> NAME/KEY: unsure
<222> LOCATION: (383)..(383)
<223> OTHER INFORMATION: n may be any nucleotide
<220> FEATURE:
<221> NAME/KEY: unsure
<222> LOCATION: (387)..(387)
<223> OTHER INFORMATION: n may be any nucleotide
<220> FEATURE:
<221> NAME/KEY: unsure
<222> LOCATION: (393)..(394)
<223> OTHER INFORMATION: n may be any nucleotide
<220> FEATURE:
<221> NAME/KEY: unsure
<222> LOCATION: (396)..(396)
<223> OTHER INFORMATION: n may be any nucleotide
<220> FEATURE:
<221> NAME/KEY: unsure
<222> LOCATION: (400)..(401)
<223> OTHER INFORMATION: n may be any nucleotide
<220> FEATURE:
<221> NAME/KEY: unsure
<222> LOCATION: (434)..(434)
<223> OTHER INFORMATION: n may be any nucleotide
<220> FEATURE:
<221> NAME/KEY: unsure
<222> LOCATION: (440)..(440)
<223> OTHER INFORMATION: n may be any nucleotide
<220> FEATURE:
<221> NAME/KEY: unsure
<222> LOCATION: (443)..(443)
<223> OTHER INFORMATION: n may be any nucleotide
<220> FEATURE:
<221> NAME/KEY: unsure
<222> LOCATION: (458)..(458)
<223> OTHER INFORMATION: n may be any nucleotide
<220> FEATURE:
<221> NAME/KEY: unsure
<222> LOCATION: (461)..(461)
<223> OTHER INFORMATION: n may be any nucleotide
<220> FEATURE:
<221> NAME/KEY: unsure
<222> LOCATION: (478)..(478)
<223> OTHER INFORMATION: n may be any nucleotide
<220> FEATURE:
<221> NAME/KEY: unsure
<222> LOCATION: (483)..(483)
<223> OTHER INFORMATION: n may be any nucleotide
<220> FEATURE:
<221> NAME/KEY: unsure
<222> LOCATION: (486)..(486)
<223> OTHER INFORMATION: n may be any nucleotide
<220> FEATURE:
<221> NAME/KEY: unsure
<222> LOCATION: (494)..(494)
<223> OTHER INFORMATION: n may be any nucleotide
<220> FEATURE:
<221> NAME/KEY: unsure
<222> LOCATION: (496)..(496)
<223> OTHER INFORMATION: n may be any nucleotide
<220> FEATURE:
<221> NAME/KEY: unsure
<222> LOCATION: (501)..(501)
<223> OTHER INFORMATION: n may be any nucleotide

<400> SEQUENCE: 20
aattccccgg gaccggntgg gtctgggtct cttgctgttg ctgatggggg ccgggctggn    60
```

| | |
|---|---|
| cgtncaaggc tggttcctcc tgcagctgca ctgngtctaa ggngagatgg tcacccgcct | 120 |
| gcctgaacgg acctgcaggc tcctgggagc agctgataca agagcgangt ctcacgaggt | 180 |
| caacccagca gcgcatctca caggggccaa ctccagcttg accggcagcg ggggccgct | 240 |
| tttatgggag actcagctgg gnctggnctt cctgaggggt ntcanctacc acgatggggn | 300 |
| cccttntggt naccaaagtt gggtactact nacaacttat tncaagnggc agttgggcgg | 360 |
| tgttgggttg cccnctgggg ctngggnaaa aannanaaan naagggcttt taaaaagggg | 420 |
| aaaaccggtt aacncgaggn agntggagtt tttggttnaa ncatgattaa acctgggnag | 480 |
| ggncanaaaa aatncnggtg ntt | 503 |

<210> SEQ ID NO 21
<211> LENGTH: 26
<212> TYPE: DNA
<213> ORGANISM: Artificial Sequence
<220> FEATURE:
<223> OTHER INFORMATION: Oligonucleotide

<400> SEQUENCE: 21
gggggatcca tggtcacccg cctgcc                26

<210> SEQ ID NO 22
<211> LENGTH: 25
<212> TYPE: DNA
<213> ORGANISM: Artificial Sequence
<220> FEATURE:
<223> OTHER INFORMATION: Oligonucleotide

<400> SEQUENCE: 22
gggaagcttc accatgaaag ccccg                 25

<210> SEQ ID NO 23
<211> LENGTH: 26
<212> TYPE: DNA
<213> ORGANISM: Artificial Sequence
<220> FEATURE:
<223> OTHER INFORMATION: Oligonucleotide

<400> SEQUENCE: 23
gggccatgga tggtcacccg cctgcc                26

<210> SEQ ID NO 24
<211> LENGTH: 27
<212> TYPE: DNA
<213> ORGANISM: Artificial Sequence
<220> FEATURE:
<223> OTHER INFORMATION: Oligonucleotide

<400> SEQUENCE: 24
gggccatggg ccaactccag cttgacc               27

<210> SEQ ID NO 25
<211> LENGTH: 31
<212> TYPE: DNA
<213> ORGANISM: Artificial Sequence
<220> FEATURE:
<223> OTHER INFORMATION: Oligonucleotide

<400> SEQUENCE: 25
gggggatccc gcagctgcac tggcgtctag g           31

<210> SEQ ID NO 26

```
<211> LENGTH: 25
<212> TYPE: DNA
<213> ORGANISM: Artificial Sequence
<220> FEATURE:
<223> OTHER INFORMATION: Oligonucleotide

<400> SEQUENCE: 26
gggtctagac accatgaaag ccccg                                       25

<210> SEQ ID NO 27
<211> LENGTH: 29
<212> TYPE: DNA
<213> ORGANISM: Artificial Sequence
<220> FEATURE:
<223> OTHER INFORMATION: Oligonucleotide

<400> SEQUENCE: 27
cgcggatccc tcctgggagc agctgatac                                   29

<210> SEQ ID NO 28
<211> LENGTH: 28
<212> TYPE: DNA
<213> ORGANISM: Artificial Sequence
<220> FEATURE:
<223> OTHER INFORMATION: Oligonucleotide

<400> SEQUENCE: 28
gggggatcct gacaccatga aagccccg                                    28

<210> SEQ ID NO 29
<211> LENGTH: 24
<212> TYPE: DNA
<213> ORGANISM: Artificial Sequence
<220> FEATURE:
<223> OTHER INFORMATION: Oligonucleotide

<400> SEQUENCE: 29
cgcggatcct cacaccatga aagc                                        24

<210> SEQ ID NO 30
<211> LENGTH: 25
<212> TYPE: DNA
<213> ORGANISM: Artificial Sequence
<220> FEATURE:
<223> OTHER INFORMATION: Oligonucleotide

<400> SEQUENCE: 30
gggggatccc accatgaaag ccccg                                       25

<210> SEQ ID NO 31
<211> LENGTH: 733
<212> TYPE: DNA
<213> ORGANISM: Artificial Sequence
<220> FEATURE:
<223> OTHER INFORMATION: Fc immunoglobulin fragment

<400> SEQUENCE: 31
gggatccgga gcccaaatct tctgacaaaa ctcacacatg cccaccgtgc ccagcacctg   60
aattcgaggg tgcaccgtca gtcttcctct tccccccaaa acccaaggac acccctcatga  120 tctcccggac tcctgaggtc acatgcgtgg tggtggacgt aagccacgaa gaccctgagg  180
tcaagttcaa ctggtacgtg gacggcgtgg aggtgcataa tgccaagaca aagccgcggg  240
aggagcagta caacagcacg taccgtgtgg tcagcgtcct caccgtcctg caccaggact  300
ggctgaatgg caaggagtac aagtgcaagg tctccaacaa agccctccca accccatcg   360
```

```
agaaaaccat ctccaaagcc aaagggcagc cccgagaacc acaggtgtac accctgcccc      420
catcccggga tgagctgacc aagaaccagg tcagcctgac ctgcctggtc aaaggcttct      480
atccaagcga catcgccgtg gagtgggaga gcaatgggca gccggagaac aactacaaga      540
ccacgcctcc cgtgctggac tccgacggct ccttcttcct ctacagcaag ctcaccgtgg      600
acaagagcag gtggcagcag gggaacgtct tctcatgctc cgtgatgcat gaggctctgc      660
acaaccacta cacgcagaag agcctctccc tgtctccggg taaatgagtg cgacggccgc      720
gactctagag gat                                                         733

<210> SEQ ID NO 32
<211> LENGTH: 36
<212> TYPE: DNA
<213> ORGANISM: Artificial Sequence
<220> FEATURE:
<223> OTHER INFORMATION: Oligonucleotide

<400> SEQUENCE: 32
ggggtcgacg ccatcatgga ggagagtgtc gtacgg                                 36

<210> SEQ ID NO 33
<211> LENGTH: 34
<212> TYPE: DNA
<213> ORGANISM: Artificial Sequence
<220> FEATURE:
<223> OTHER INFORMATION: Oligonucleotide

<400> SEQUENCE: 33
ggggcggccg cgccttcaca ccatgaaagc cccg                                   34

<210> SEQ ID NO 34
<211> LENGTH: 38
<212> TYPE: DNA
<213> ORGANISM: Artificial Sequence
<220> FEATURE:
<223> OTHER INFORMATION: Oligonucleotide

<400> SEQUENCE: 34
ggggcggccg cgccatcatg gaggagagtg tcgtacgg                               38

<210> SEQ ID NO 35
<211> LENGTH: 32
<212> TYPE: DNA
<213> ORGANISM: Artificial Sequence
<220> FEATURE:
<223> OTHER INFORMATION: Oligonucleotide

<400> SEQUENCE: 35
ggggtcgacg ccttcacacc atgaaagccc cg                                     32

<210> SEQ ID NO 36
<211> LENGTH: 93
<212> TYPE: DNA
<213> ORGANISM: Artificial Sequence
<220> FEATURE:
<223> OTHER INFORMATION: Oligonucleotide

<400> SEQUENCE: 36
ggggcggccg cgccatcatg aaggtctccg tggctgccct ctcctgcctc atgcttgtta      60
ctgcccttgg atcgcaggca gctgcactgg cgt                                   93

<210> SEQ ID NO 37
```

<211> LENGTH: 28
<212> TYPE: DNA
<213> ORGANISM: Artificial Sequence
<220> FEATURE:
<223> OTHER INFORMATION: Oligonucleotide

<400> SEQUENCE: 37 gggggtcgact cacaccatga aagcccccg                                    28

<210> SEQ ID NO 38
<211> LENGTH: 1017
<212> TYPE: DNA
<213> ORGANISM: Homo sapiens
<220> FEATURE:
<221> NAME/KEY: CDS
<222> LOCATION: (1)..(624)
<223> OTHER INFORMATION: cDNA

<400> SEQUENCE: 38

| | | | | | | | | | | | | | | | | |
|---|---|---|---|---|---|---|---|---|---|---|---|---|---|---|---|---|
| att | ccc | cgg | gcc | cgg | gtg | ggt | ctg | ggt | ctc | ttg | ctg | ttg | ctg | atg | ggg | 48 |
| Ile | Pro | Arg | Ala | Arg | Val | Gly | Leu | Gly | Leu | Leu | Leu | Leu | Leu | Met | Gly | |
| 1 | | | 5 | | | | 10 | | | | | 15 | | | | |
| gcc | ggg | ctg | gcc | gtc | caa | ggc | tgg | ttc | ctc | ctg | cag | ctg | cac | tgg | cgt | 96 |
| Ala | Gly | Leu | Ala | Val | Gln | Gly | Trp | Phe | Leu | Leu | Gln | Leu | His | Trp | Arg | |
| | | | 20 | | | | | 25 | | | | | 30 | | | |
| cta | gga | gag | atg | gtc | acc | cgc | ctg | cct | gac | gga | cct | gca | ggc | tcc | tgg | 144 |
| Leu | Gly | Glu | Met | Val | Thr | Arg | Leu | Pro | Asp | Gly | Pro | Ala | Gly | Ser | Trp | |
| | | 35 | | | | | 40 | | | | | 45 | | | | |
| gag | cag | ctg | ata | caa | gag | cga | agg | tct | cac | gag | gtc | aac | cca | gca | gcg | 192 |
| Glu | Gln | Leu | Ile | Gln | Glu | Arg | Arg | Ser | His | Glu | Val | Asn | Pro | Ala | Ala | |
| 50 | | | | | 55 | | | | | 60 | | | | | | |
| cat | ctc | aca | ggg | gcc | aac | tcc | agc | ttg | acc | ggc | agc | ggg | ggg | ccg | ctg | 240 |
| His | Leu | Thr | Gly | Ala | Asn | Ser | Ser | Leu | Thr | Gly | Ser | Gly | Gly | Pro | Leu | |
| 65 | | | | | 70 | | | | | 75 | | | | | 80 | |
| tta | tgg | gag | act | cag | ctg | ggc | ctg | gcc | ttc | ctg | agg | ggc | ctc | agc | tac | 288 |
| Leu | Trp | Glu | Thr | Gln | Leu | Gly | Leu | Ala | Phe | Leu | Arg | Gly | Leu | Ser | Tyr | |
| | | | | 85 | | | | | 90 | | | | | 95 | | |
| cac | gat | ggg | gcc | ctt | gtg | gtc | acc | aaa | gct | ggc | tac | tac | tac | atc | tac | 336 |
| His | Asp | Gly | Ala | Leu | Val | Val | Thr | Lys | Ala | Gly | Tyr | Tyr | Tyr | Ile | Tyr | |
| | | | 100 | | | | | 105 | | | | | 110 | | | |
| tcc | aag | gtg | cag | ctg | ggc | ggt | gtg | ggc | tgc | ccg | ctg | ggc | ctg | gcc | agc | 384 |
| Ser | Lys | Val | Gln | Leu | Gly | Gly | Val | Gly | Cys | Pro | Leu | Gly | Leu | Ala | Ser | |
| | | | 115 | | | | | 120 | | | | | 125 | | | |
| acc | atc | acc | cac | ggc | ctc | tac | aag | cgc | aca | ccc | cgc | tac | ccc | gag | gag | 432 |
| Thr | Ile | Thr | His | Gly | Leu | Tyr | Lys | Arg | Thr | Pro | Arg | Tyr | Pro | Glu | Glu | |
| | | 130 | | | | | 135 | | | | | 140 | | | | |
| ctg | gag | ctg | ttg | gtc | agc | cag | cag | tca | ccc | tgc | gga | cgg | gcc | acc | agc | 480 |
| Leu | Glu | Leu | Leu | Val | Ser | Gln | Gln | Ser | Pro | Cys | Gly | Arg | Ala | Thr | Ser | |
| 145 | | | | | 150 | | | | | 155 | | | | | 160 | |
| agc | tcc | cgg | gtc | tgg | tgg | gac | agc | agc | ttc | ctg | ggt | ggt | gtg | gta | cac | 528 |
| Ser | Ser | Arg | Val | Trp | Trp | Asp | Ser | Ser | Phe | Leu | Gly | Gly | Val | Val | His | |
| | | | | 165 | | | | | 170 | | | | | 175 | | |
| ctg | gag | gct | ggg | gag | gag | gtg | gtc | gtc | cgt | gtg | ctg | gat | gaa | cgc | ctg | 576 |
| Leu | Glu | Ala | Gly | Glu | Glu | Val | Val | Val | Arg | Val | Leu | Asp | Glu | Arg | Leu | |
| | | | 180 | | | | | 185 | | | | | 190 | | | |
| gtt | cga | ctg | cgt | gat | ggt | acc | cgg | tct | tac | ttc | ggg | gct | ttc | atg | gtg | 624 |
| Val | Arg | Leu | Arg | Asp | Gly | Thr | Arg | Ser | Tyr | Phe | Gly | Ala | Phe | Met | Val | |
| | | 195 | | | | | 200 | | | | | 205 | | | | | tgaaggaagg agcgtggtgc attggacatg ggtctgacac gtggagaact cagagggtgc    684 ctcaggggaa agaaaactca cgaagcagag gctgggcgtg gtggctctcg cctgtaatcc    744 cagcactttg ggaggccaag gcaggcggat cacctgaggt caggagttcg agaccagcct    804

```
ggctaacatg gcaaaacccc atctctacta aaaatacaaa aattagccgg acgtggtggt      864
gcctgcctgt aatccagcta ctcaggaggc tgaggcagga taattttgct taaacccggg      924
aggcggaggt tgcagtgagc cgagatcaca ccactgcact ccaacctggg aaacgcagtg      984
agactgtgcc tcaaaaaaaa caaaaaaaaa aaa                                  1017
```

```
<210> SEQ ID NO 39
<211> LENGTH: 208
<212> TYPE: PRT
<213> ORGANISM: Homo sapiens

<400> SEQUENCE: 39

Ile Pro Arg Ala Arg Val Gly Leu Gly Leu Leu Leu Leu Met Gly
1               5                   10                  15

Ala Gly Leu Ala Val Gln Gly Trp Phe Leu Leu Gln Leu His Trp Arg
            20                  25                  30

Leu Gly Glu Met Val Thr Arg Leu Pro Asp Gly Pro Ala Gly Ser Trp
        35                  40                  45

Glu Gln Leu Ile Gln Glu Arg Arg Ser His Glu Val Asn Pro Ala Ala
    50                  55                  60

His Leu Thr Gly Ala Asn Ser Ser Leu Thr Gly Ser Gly Pro Leu
65                  70                  75                  80

Leu Trp Glu Thr Gln Leu Gly Leu Ala Phe Leu Arg Gly Leu Ser Tyr
                85                  90                  95

His Asp Gly Ala Leu Val Val Thr Lys Ala Gly Tyr Tyr Ile Tyr
            100                 105                 110

Ser Lys Val Gln Leu Gly Gly Val Gly Cys Pro Leu Gly Leu Ala Ser
        115                 120                 125

Thr Ile Thr His Gly Leu Tyr Lys Arg Thr Pro Arg Tyr Pro Glu Glu
    130                 135                 140

Leu Glu Leu Leu Val Ser Gln Gln Ser Pro Cys Gly Arg Ala Thr Ser
145                 150                 155                 160

Ser Ser Arg Val Trp Trp Asp Ser Ser Phe Leu Gly Gly Val Val His
                165                 170                 175

Leu Glu Ala Gly Glu Glu Val Val Arg Val Leu Asp Glu Arg Leu
            180                 185                 190

Val Arg Leu Arg Asp Gly Thr Arg Ser Tyr Phe Gly Ala Phe Met Val
        195                 200                 205
```

```
<210> SEQ ID NO 40
<211> LENGTH: 43
<212> TYPE: DNA
<213> ORGANISM: Artificial Sequence
<220> FEATURE:
<223> OTHER INFORMATION: Oligonucleotide

<400> SEQUENCE: 40
gacagtggat ccgccaccat ggtcacccgc ctgcctgacg gac                        43
```

```
<210> SEQ ID NO 41
<211> LENGTH: 25
<212> TYPE: DNA
<213> ORGANISM: Artificial Sequence
<220> FEATURE:
<223> OTHER INFORMATION: Oligonucleotide

<400> SEQUENCE: 41
cgcggatcct gggagcagct gatac                                            25
```

<210> SEQ ID NO 42
<211> LENGTH: 25
<212> TYPE: DNA
<213> ORGANISM: Artificial Sequence
<220> FEATURE:
<223> OTHER INFORMATION: Oligonucleotide

<400> SEQUENCE: 42
cgccatatga cccgcctgcc tgacg                                    25

<210> SEQ ID NO 43
<211> LENGTH: 28
<212> TYPE: DNA
<213> ORGANISM: Artificial Sequence
<220> FEATURE:
<223> OTHER INFORMATION: Oligonucleotide

<400> SEQUENCE: 43
cgccatatga gctgggagca gctgatac                                 28

<210> SEQ ID NO 44
<211> LENGTH: 28
<212> TYPE: DNA
<213> ORGANISM: Artificial Sequence
<220> FEATURE:
<223> OTHER INFORMATION: Oligonucleotide

<400> SEQUENCE: 44
cgccatatga gcagcttgac cggcagcg                                 28

<210> SEQ ID NO 45
<211> LENGTH: 28
<212> TYPE: DNA
<213> ORGANISM: Artificial Sequence
<220> FEATURE:
<223> OTHER INFORMATION: Oligonucleotide

<400> SEQUENCE: 45
cgcggtacct tacaccatga aagccccg                                 28

<210> SEQ ID NO 46
<211> LENGTH: 11
<212> TYPE: PRT
<213> ORGANISM: Artificial Sequence
<220> FEATURE:
<223> OTHER INFORMATION: TNF/Fas Ligand Family Motif

<400> SEQUENCE: 46

Gly Leu Tyr Leu Ile Tyr Ser Gln Val Leu Phe
1               5                   10

<210> SEQ ID NO 47
<211> LENGTH: 11
<212> TYPE: PRT
<213> ORGANISM: Artificial Sequence
<220> FEATURE:
<223> OTHER INFORMATION: TNF/FAS Ligand Family Motif

<400> SEQUENCE: 47

Gly Tyr Tyr Tyr Ile Tyr Ser Lys Val Gln Leu
1               5                   10

<210> SEQ ID NO 48
<211> LENGTH: 28
<212> TYPE: DNA

```
<213> ORGANISM: Artificial Sequence
<220> FEATURE:
<223> OTHER INFORMATION: Oligonucleotide

<400> SEQUENCE: 48
cgggatccat gctcctgcct tgggccac                                              28

<210> SEQ ID NO 49
<211> LENGTH: 29
<212> TYPE: DNA
<213> ORGANISM: Artificial Sequence
<220> FEATURE:
<223> OTHER INFORMATION: Oligonucleotide

<400> SEQUENCE: 49
gcggatcctg ggggcagtgg ctctaatgg                                             29

<210> SEQ ID NO 50
<211> LENGTH: 3974
<212> TYPE: DNA
<213> ORGANISM: Artificial Sequence
<220> FEATURE:
<223> OTHER INFORMATION: pHE4-5 expression vector

<400> SEQUENCE: 50
ggtacctaag tgagtagggc gtccgatcga cggacgcctt ttttttgaat tcgtaatcat    60
ggtcatagct gtttcctgtg tgaaattgtt atccgctcac aattccacac aacatacgag   120
ccggaagcat aaagtgtaaa gcctggggtg cctaatgagt gagctaactc acattaattg   180
cgttgcgctc actgcccgct ttccagtcgg gaaacctgtc gtgccagctg cattaatgaa   240
tcggccaacg cgcggggaga ggcggtttgc gtattgggcg ctcttccgct tcctcgctca   300
ctgactcgct gcgctcggtc gttcggctgc ggcgagcggt atcagctcac tcaaaggcgg   360
taatacggtt atccacagaa tcaggggata acgcaggaaa gaacatgtga gcaaaaggcc   420
agcaaaaggc caggaaccgt aaaaaggccg cgttgctggc gtttttccat aggctccgcc   480
cccctgacga gcatcacaaa aatcgacgct caagtcagag gtggcgaaac ccgacaggac   540
tataaagata ccaggcgttt ccccctggaa gctccctcgt gcgctctcct gttccgaccc   600
tgccgcttac cggatacctg tccgcctttc tcccttcggg aagcgtggcg ctttctcata   660
gctcacgctg taggtatctc agttcggtgt aggtcgttcg ctccaagctg ggctgtgtgc   720
acgaaccccc cgttcagccc gaccgctgcg ccttatccgg taactatcgt cttgagtcca   780
acccggtaag acacgactta tcgccactgg cagcagccac tggtaacagg attagcagag   840
cgaggtatgt aggcggtgct acagagttct tgaagtggtg gcctaactac ggctacacta   900
gaagaacagt atttggtatc tgcgctctgc tgaagccagt taccttcgga aaaagagttg   960
gtagctcttg atccggcaaa caaaccaccg ctggtagcgg tggttttttt gtttgcaagc  1020
agcagattac gcgcagaaaa aaaggatctc aagaagatcc tttgatcttt tctacggggt  1080
ctgacgctca gtggaacgaa aactcacgtt aagggatttt ggtcatgaga ttatcgtcga  1140
caattcgcgc gcgaaggcga agcggcatgc atttacgttg acaccatcga atggtgcaaa  1200
acctttcgcg gtatggcatg atagcgcccg gaagagagtc aattcagggt ggtgaatgtg  1260
aaaccagtaa cgttatacga tgtcgcagag tatgccggtg tctcttatca gaccgtttcc  1320
cgcgtggtga accaggccag ccacgtttct gcgaaaacgc gggaaaaagt ggaagcggcg  1380
atggcggagc tgaattacat tcccaaccgc gtggcacaac aactggcggg caaacagtcg  1440
ttgctgattg gcgttgccac ctccagtctg gccctgcacg cgccgtcgca aattgtcgcg  1500
```

-continued

```
gcgattaaat ctcgcgccga tcaactgggt gccagcgtgg tggtgtcgat ggtagaacga    1560
agcggcgtcg aagcctgtaa agcggcggtg cacaatcttc tcgcgcaacg cgtcagtggg    1620
ctgatcatta actatccgct ggatgaccag gatgccattg ctgtggaagc tgcctgcact    1680
aatgttccgg cgttatttct tgatgtctct gaccagacac ccatcaacag tattattttc    1740
tcccatgaag acggtacgcg actgggcgtg gagcatctgg tcgcattggg tcaccagcaa    1800
atcgcgctgt tagcgggccc attaagttct gtctcggcgc gtctgcgtct ggctggctgg    1860
cataaatatc tcactcgcaa tcaaattcag ccgatagcgg aacgggaagg cgactggagt    1920
gccatgtccg gttttcaaca aaccatgcaa atgctgaatg agggcatcgt tcccactgcg    1980
atgctggttg ccaacgatca gatggcgctg gcgcaatgc gcgccattac cgagtccggg    2040
ctgcgcgttg gtgcggatat ctcggtagtg ggatacgacg ataccgaaga cagctcatgt    2100
tatatcccgc cgttaaccac catcaaacag gattttcgcc tgctggggca aaccagcgtg    2160
gaccgcttgc tgcaactctc tcagggccag gcggtgaagg gcaatcagct gttgcccgtc    2220
tcactggtga aagaaaaac caccctggcg cccaatacgc aaaccgcctc tccccgcgcg    2280
ttggccgatt cattaatgca gctggcacga caggtttccc gactggaaag cgggcagtga    2340
gcgcaacgca attaatgtaa gttagcgcga attgtcgacc aaagcggcca tcgtgcctcc    2400
ccactcctgc agttcggggg catggatgcg cggatagccg ctgctggttt cctggatgcc    2460
gacggatttg cactgccggt agaactccga gaggtcgtcc agcctcaggc agcagctgaa    2520
ccaactcgcg aggggatcga gcccggggtg ggcgaagaac tccagcatga gatccccgcg    2580
ctggaggatc atccagccgg cgtcccggaa aacgattccg aagcccaacc tttcatagaa    2640
ggcggcggtg gaatcgaaat ctcgtgatgg caggttgggc gtcgcttggt cggtcatttc    2700
gaacccagga gtcccgctca gaagaactcg tcaagaaggc gatagaaggc gatgcgctgc    2760
gaatcgggag cggcgatacc gtaaagcacg aggaagcggt cagcccattc gccgccaagc    2820
tcttcagcaa tatcacgggt agccaacgct atgtcctgat agcggtccgc cacacccagc    2880
cggccacagt cgatgaatcc agaaaagcgg ccattttcca ccatgatatt cggcaagcag    2940
gcatcgccat gggtcacgac gagatcctcg ccgtcgggca tgcgcgcctt gagcctggcg    3000
aacagttcgg ctggcgcgag cccctgatgc tcttcgtcca gatcatcctg atcgacaaga    3060
ccggcttcca tccgagtacg tgctcgctcg atgcgatgtt tcgcttggtg gtcgaatggg    3120
caggtagccg gatcaagcgt atgcagccgc cgcattgcat cagccatgat ggatactttc    3180
tcggcaggag caaggtgaga tgacaggaga tcctgccccg gcacttcgcc caatagcagc    3240
cagtcccttc ccgcttcagt gacaacgtcg agcacagctg cgcaaggaac gcccgtcgtg    3300
gccagccacg atagccgcgc tgcctcgtcc tgcagttcat tcagggcacc ggacaggtcg    3360
gtcttgacaa aaagaaccgg gcgcccctgc gctgacagcc ggaacacggc ggcatcagag    3420
cagccgattg tctgttgtgc ccagtcatag ccgaatagcc tctccaccca agcggccgga    3480
gaacctgcgt gcaatccatc ttgttcaatc atgcgaaacg atcctcatcc tgtctcttga    3540
tcagatcttg atccctgcg ccatcagatc cttggcggca agaaagccat ccagtttact    3600
ttgcagggct tcccaacctt accagagggc gccccagctg gcaattccgg ttcgcttgct    3660
gtccataaaa ccgcccagtc tagctatcgc catgtaagcc cactgcaagc tacctgcttt    3720
ctctttgcgc ttgcgttttc ccttgtccag atagcccagt agctgacatt catccggggt    3780
cagcaccgtt tctgcggact ggctttctac gtgttccgct tcctttagca gcccttgcgc    3840
```

```
cctgagtgct tgcggcagcg tgaagcttaa aaaactgcaa aaaatagttt gacttgtgag      3900
cggataacaa ttaagatgta cccaattgtg agcggataac aatttcacac attaaagagg      3960
agaaattaca tatg                                                       3974
```

<210> SEQ ID NO 51
<211> LENGTH: 112
<212> TYPE: DNA
<213> ORGANISM: Artificial Sequence
<220> FEATURE:
<223> OTHER INFORMATION: pHE promoter regulatory elements

<400> SEQUENCE: 51

```
aagcttaaaa aactgcaaaa aatagtttga cttgtgagcg gataacaatt aagatgtacc        60
caattgtgag cggataacaa tttcacacat taaagaggag aaattacata tg              112
```

<210> SEQ ID NO 52
<211> LENGTH: 25
<212> TYPE: DNA
<213> ORGANISM: Artificial Sequence
<220> FEATURE:
<223> OTHER INFORMATION: Oligonucleotide

<400> SEQUENCE: 52

```
cgcggatccc ggagagatgg tcacc                                             25
```

<210> SEQ ID NO 53
<211> LENGTH: 27
<212> TYPE: DNA
<213> ORGANISM: Artificial Sequence
<220> FEATURE:
<223> OTHER INFORMATION: Oligonucleotide

<400> SEQUENCE: 53

```
cgctctagac cttcacacca tgaaagc                                           27
```

<210> SEQ ID NO 54
<211> LENGTH: 27
<212> TYPE: DNA
<213> ORGANISM: Artificial Sequence
<220> FEATURE:
<223> OTHER INFORMATION: Oligonucleotide

<400> SEQUENCE: 54

```
cgcggatcca tgggtctggg tctcttg                                           27
```

<210> SEQ ID NO 55
<211> LENGTH: 51
<212> TYPE: DNA
<213> ORGANISM: Artificial Sequence
<220> FEATURE:
<223> OTHER INFORMATION: Oligonucleotide

<400> SEQUENCE: 55

```
cgctctagat caagcgtagt ctgggacgtc gtatggcacc atgaaagccc c                51
```

<210> SEQ ID NO 56
<211> LENGTH: 459
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (6)..(7)
<223> OTHER INFORMATION: May be any amino acid or a gap in the sequence

```
<220> FEATURE:
<221> NAME/KEY: VARIANT
<222> LOCATION: (15)..(16)
<223> OTHER INFORMATION: May be any amino acid or a gap in the sequence
<220> FEATURE:
<221> NAME/KEY: VARIANT
<222> LOCATION: (19)..(23)
<223> OTHER INFORMATION: May be any amino acid or a gap in the sequence
<220> FEATURE:
<221> NAME/KEY: VARIANT
<222> LOCATION: (25)..(30)
<223> OTHER INFORMATION: May be any amino acid or a gap in the sequence
<220> FEATURE:
<221> NAME/KEY: VARIANT
<222> LOCATION: (31)..(43)
<223> OTHER INFORMATION: May be any amino acid or a gap in the sequence
<220> FEATURE:
<221> NAME/KEY: VARIANT
<222> LOCATION: (50)..(51)
<223> OTHER INFORMATION: May be any amino acid or a gap in the sequence
<220> FEATURE:
<221> NAME/KEY: VARIANT
<222> LOCATION: (53)..(54)
<223> OTHER INFORMATION: May be any amino acid or a gap in the sequence
<220> FEATURE:
<221> NAME/KEY: VARIANT
<222> LOCATION: (57)..(58)
<223> OTHER INFORMATION: May be any amino acid or a gap in the sequence
<220> FEATURE:
<221> NAME/KEY: VARIANT
<222> LOCATION: (60)..(83)
<223> OTHER INFORMATION: May be any amino acid or a gap in the sequence
<220> FEATURE:
<221> NAME/KEY: VARIANT
<222> LOCATION: (87)..(107)
<223> OTHER INFORMATION: May be any amino acid or a gap in the sequence
<220> FEATURE:
<221> NAME/KEY: VARIANT
<222> LOCATION: (121)..(122)
<223> OTHER INFORMATION: May be any amino acid or a gap in the sequence
<220> FEATURE:
<221> NAME/KEY: VARIANT
<222> LOCATION: (127)..(135)
<223> OTHER INFORMATION: May be any amino acid or a gap in the sequence
<220> FEATURE:
<221> NAME/KEY: VARIANT
<222> LOCATION: (139)..(140)
<223> OTHER INFORMATION: May be any amino acid or a gap in the sequence
<220> FEATURE:
<221> NAME/KEY: VARIANT
<222> LOCATION: (142)..(142)
<223> OTHER INFORMATION: May be any amino acid or a gap in the sequence
<220> FEATURE:
<221> NAME/KEY: VARIANT
<222> LOCATION: (145)..(145)
<223> OTHER INFORMATION: May be any amino acid or a gap in the sequence
<220> FEATURE:
<221> NAME/KEY: VARIANT
<222> LOCATION: (147)..(149)
<223> OTHER INFORMATION: May be any amino acid or a gap in the sequence
<220> FEATURE:
<221> NAME/KEY: VARIANT
<222> LOCATION: (151)..(151)
<223> OTHER INFORMATION: May be any amino acid or a gap in the sequence
<220> FEATURE:
<221> NAME/KEY: VARIANT
<222> LOCATION: (153)..(153)
<223> OTHER INFORMATION: May be any amino acid or a gap in the sequence
<220> FEATURE:
<221> NAME/KEY: VARIANT
<222> LOCATION: (155)..(174)
<223> OTHER INFORMATION: May be any amino acid or a gap in the sequence
<220> FEATURE:
<221> NAME/KEY: VARIANT
<222> LOCATION: (209)..(211)
<223> OTHER INFORMATION: May be any amino acid or a gap in the sequence
<220> FEATURE:
<221> NAME/KEY: VARIANT
<222> LOCATION: (214)..(214)
```

```
<223> OTHER INFORMATION: May be any amino acid or a gap in the sequence
<220> FEATURE:
<221> NAME/KEY: VARIANT
<222> LOCATION: (218)..(238)
<223> OTHER INFORMATION: May be any amino acid or a gap in the sequence
<220> FEATURE:
<221> NAME/KEY: VARIANT
<222> LOCATION: (248)..(266)
<223> OTHER INFORMATION: May be any amino acid or a gap in the sequence
<220> FEATURE:
<221> NAME/KEY: VARIANT
<222> LOCATION: (304)..(304)
<223> OTHER INFORMATION: May be any amino acid or a gap in the sequence
<220> FEATURE:
<221> NAME/KEY: VARIANT
<222> LOCATION: (336)..(338)
<223> OTHER INFORMATION: May be any amino acid or a gap in the sequence
<220> FEATURE:
<221> NAME/KEY: VARIANT
<222> LOCATION: (380)..(380)
<223> OTHER INFORMATION: May be any amino acid or a gap in the sequence
<220> FEATURE:
<221> NAME/KEY: VARIANT
<222> LOCATION: (384)..(402)
<223> OTHER INFORMATION: May be any amino acid or a gap in the sequence
<220> FEATURE:
<221> NAME/KEY: VARIANT
<222> LOCATION: (407)..(407)
<223> OTHER INFORMATION: May be any amino acid or a gap in the sequence
<220> FEATURE:
<221> NAME/KEY: VARIANT
<222> LOCATION: (409)..(459)
<223> OTHER INFORMATION: May be any amino acid or a gap in the sequence

<400> SEQUENCE: 56

Met Thr Pro Pro Glu Xaa Xaa Arg Leu Phe Leu Pro Arg Val Xaa Xaa
1               5                   10                  15

Val Asp Xaa Xaa Xaa Xaa Pro Xaa Xaa Xaa Gly Xaa Xaa Xaa
            20                  25                  30

Xaa Xaa Xaa Xaa Xaa Xaa Xaa Xaa Xaa Xaa Cys Gly Thr Thr Leu
        35                  40                  45

His Xaa Xaa Pro Xaa Xaa Arg Arg Xaa Xaa Cys Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Leu Leu Leu Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Gly Leu Gly Leu Leu
                100                 105                 110

Leu Val Leu Leu Pro Gly Ala Gln Xaa Xaa Gly Leu Pro Gly Xaa Xaa
            115                 120                 125

Xaa Xaa Xaa Xaa Xaa Xaa Xaa Val Gly Leu Xaa Xaa Phe Xaa Leu Phe
    130                 135                 140

Xaa Leu Xaa Xaa Xaa Leu Xaa Glu Xaa Val Xaa Xaa Xaa Xaa Xaa
145                 150                 155                 160

Xaa Xaa Xaa Xaa Xaa Xaa Xaa Xaa Xaa Xaa Xaa Xaa Xaa Arg Thr
                165                 170                 175

Pro Ser Ala Ala Gln Thr Ala Arg Gln His Pro Ser Met Glu Leu Ala
            180                 185                 190

Lys Ser Thr Leu Lys Pro Ala Ala His Leu Ile Gly Asp Pro Ser Ser
            195                 200                 205

Xaa Xaa Xaa Gln Asn Xaa Pro Leu Leu Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Trp Glu
```

```
                  225                 230                 235                 240

Ala Asn Leu Gly Arg Ala Phe Xaa Xaa Xaa Xaa Xaa Xaa Xaa Xaa
                            245                 250                 255

Xaa Xaa Xaa Xaa Xaa Xaa Xaa Xaa Xaa Leu Gln Asp Gly Phe Ser
                        260                 265                 270

Leu Ser Asn Gly Ser Leu Val Val Pro Thr Ser Gly Ile Tyr Phe Val
                    275                 280                 285

Tyr Ser Gln Val Val Phe Ser Gly Lys Ala Tyr Ser Pro Gly Ala Xaa
                290                 295                 300

Ser Ser Pro Leu Tyr Leu Ala His Glu Val Gln Leu Arg Ser Ser Gln
        305                 310                 315                 320

Tyr Pro Phe His Val Pro Leu Leu Ser Ser Gln Lys Met Val Tyr Xaa
                            325                 330                 335

Xaa Xaa Pro Gly Leu Gln Glu Pro Trp Leu Asp Ser Ser Tyr Leu Gly
                        340                 345                 350

Ala Ala Phe Gln Leu Thr Gln Gly Asp Gln Leu Ser Val His Val Asp
                    355                 360                 365

Gly Ile Pro Leu Leu Val Leu Ser Glu Ser Thr Xaa Val Phe Phe Xaa
                370                 375                 380

Xaa Xaa Xaa Xaa Xaa Xaa Xaa Xaa Xaa Xaa Xaa Xaa Xaa Xaa Xaa
        385                 390                 395                 400

Xaa Xaa Gly Ala Phe Ala Xaa Leu Xaa Xaa Xaa Xaa Xaa Xaa Xaa
                            405                 410                 415

Xaa Xaa Xaa Xaa Xaa Xaa Xaa Xaa Xaa Xaa Xaa Xaa Xaa Xaa Xaa
                        420                 425                 430

Xaa Xaa Xaa Xaa Xaa Xaa Xaa Xaa Xaa Xaa Xaa Xaa Xaa Xaa Xaa
                    435                 440                 445

Xaa Xaa Xaa Xaa Xaa Xaa Xaa Xaa Xaa Xaa Xaa
                450                 455

<210> SEQ ID NO 57
<211> LENGTH: 16
<212> TYPE: PRT
<213> ORGANISM: Artificial Sequence
<220> FEATURE:
<223> OTHER INFORMATION: FLAG peptide

<400> SEQUENCE: 57

Asp Tyr Lys Asp Asp Asp Asp Lys Leu Ala Ala Ala Asn Ser Asp Leu
1               5                   10                  15

<210> SEQ ID NO 58
<211> LENGTH: 5
<212> TYPE: PRT
<213> ORGANISM: Homo sapiens

<400> SEQUENCE: 58

Leu Ile Gln Glu Arg
1               5

<210> SEQ ID NO 59
<211> LENGTH: 5
<212> TYPE: PRT
<213> ORGANISM: Artificial Sequence
<220> FEATURE:
<223> OTHER INFORMATION: Portion of ck-beta8/AIM II fusion protein

<400> SEQUENCE: 59

Ser Gln Ala Gly Ser
1               5
```

-continued

```
1               5

<210> SEQ ID NO 60
<211> LENGTH: 5
<212> TYPE: PRT
<213> ORGANISM: Artificial Sequence
<220> FEATURE:
<223> OTHER INFORMATION: Portion of ck-beta8/AIM II fusion protein

<400> SEQUENCE: 60

Gly Ser Gln Leu His
1               5

<210> SEQ ID NO 61
<211> LENGTH: 34
<212> TYPE: PRT
<213> ORGANISM: Artificial Sequence
<220> FEATURE:
<223> OTHER INFORMATION: Portion of ck-beta8/AIM II fusion protein

<400> SEQUENCE: 61

Ser Gln Ala Gly Ser Gln Leu His Trp Arg Leu Gly Glu Met Val Thr
1               5                   10                  15

Arg Leu Pro Asp Gly Pro Ala Gly Ser Trp Glu Gln Leu Ile Gln Glu
            20                  25                  30

Arg Asn
```

What is claimed is:

1. An isolated polypeptide consisting of at least 30 contiguous amino acids of SEQ ID NO:39.

2. The polypeptide of claim 1, wherein a heterologous polypeptide is fused to said polypeptide.

3. The polypeptide of claim 1, which is produced by a host cell.

4. A composition comprising the polypeptide of claim 1 and a pharmaceutically acceptable carrier.

5. The polypeptide of claim 1, consisting of at least 50 contiguous amino acids of SEQ ID NO:39.

6. The polypeptide of claim 5, wherein a heterologous polypeptide is fused to said polypeptide.

7. The polypeptide of claim 5, which is produced by a host cell.

8. A composition comprising the polypeptide of claim 5 and a pharmaceutically acceptable carrier.

* * * * *